United States Patent
Su et al.

(10) Patent No.: US 8,552,028 B2
(45) Date of Patent: Oct. 8, 2013

(54) 8-PHENYLISOQUINOLINES AND PHARMACEUTICAL COMPOSITION USED IN TREATMENT FOR SEPSIS

(75) Inventors: Ming-Jai Su, Taipei (TW); Ling-Wei Hsin, Taipei (TW)

(73) Assignee: National Taiwan University, Taipei (TW)

( * ) Notice: Subject to any disclaimer, the term of this patent is extended or adjusted under 35 U.S.C. 154(b) by 46 days.

(21) Appl. No.: 13/225,508

(22) Filed: Sep. 5, 2011

(65) Prior Publication Data

US 2013/0059882 A1    Mar. 7, 2013

(51) Int. Cl.
C07D 217/04    (2006.01)
A61K 31/472    (2006.01)

(52) U.S. Cl.
USPC .......................................... 514/307; 546/149

(58) Field of Classification Search
None
See application file for complete search history.

(56) References Cited

PUBLICATIONS

Hara et al, Chemical & Pharmaceutical Bulletin (1983), 31(2), 730-2.*

* cited by examiner

*Primary Examiner* — Zinna Northington Davis

(57) ABSTRACT

A compound is provided. The compound includes a formula of:

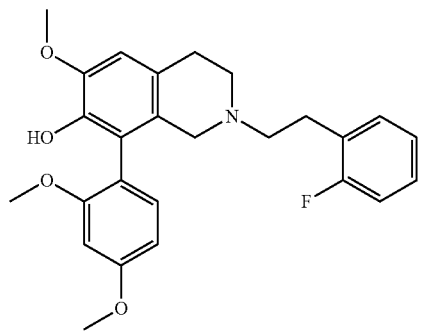

13 Claims, 10 Drawing Sheets

8-PHENYLISOQUINOLINES AND PHARMACEUTICAL COMPOSITION USED IN TREATMENT FOR SEPSIS

FIELD OF THE INVENTION

The present invention relates to a series of 8-phenylisoquinoline derivatives, and more particularly to a series of 8-phenylisoquinoline derivatives used in treatment for sepsis

BACKGROUND OF THE INVENTION

Sepsis syndrome is a serious whole-body inflammation disease caused by bacteria-released toxins into blood. This syndrome often causes blood coagulation of the patients, and they finally die of multiple organ dysfunction syndromes. According to several epidemiological studies, rates of hospitalization for severe sepsis range from 50 to 300 cases per 100,000 in USA, and the mortality of severe sepsis in ICU ranges from 18% to 55%. The medical cost per patient was estimated from US$26,450 to US$39,100.

In Taiwan, the rate of severe sepsis incidence is 359 per 100,000, and the mortality of severe sepsis is about 30%. The estimated cost for caring a sepsis patient is 866-6505 USD. So far, the main management of sepsis is symptoms relief and vital signs supports, such as using anti-inflammation drugs, antibiotics, blood-vessel constriction drugs and intravenous drips.

Currently, the only one FDA-proved therapeutic agent for reducing mortality of severe sepsis patients and treating sepsis is Drotrecogin alfa (Xigris®). Xigris® is a recombinant human activated protein C by recombinant genetic technology. The recombinant human activated protein C could inhibit the activity of the Factor Va and Factor VIIIa, inhibit the synthesis of the thrombin and inhibit the synthesis of plasminogen activator inhibitor-1 (PAI-1) to regulate the coagulation reaction and possess the features of anti-thrombus and fibrinolysis. However, according to several clinical researches, the benefit effects of Xigris® on reducing mortality of servere sepsis patients is still controversial, so new therapeutic agents for sepsis is still desired.

Serotonin (also called 5-hydroxytryptamine or 5-HT) is a neurotransmitter which could induce coagulation of platelets, contraction of coronary artery. $5\text{-HT}_{2A}$ receptor, which is one subtype of the 5-HT receptor family and a G-protein coupled receptor.

The present $5\text{-HT}_{2A}$ receptor antagonists include sarpogrelate and ketanserin. The method of treatment sepsis using $5\text{-HT}_{2A}$ receptor antagonists is still under research. In order to overcome the drawbacks in the prior art, a novel series of 8-phenylisoquinolines and pharmaceutical composition used in treatment for sepsis is provided.

SUMMARY OF THE INVENTION

In accordance with an aspect of the present invention, a compound is provided. The compound includes a formula of:

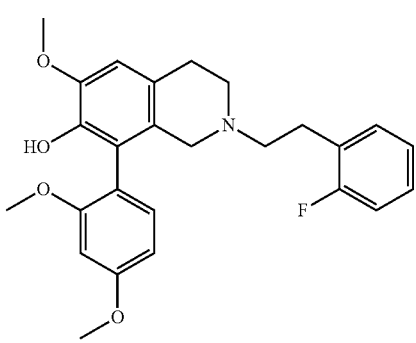 [SMILES: COc1ccc(-c2c(O)c(OC)cc3c2CN(CCc2ccccc2F)CC3)c(OC)c1]

In accordance with another aspect of the present invention, A compound or a pharmaceutically acceptable salt thereof is provided. The compound or a pharmaceutically acceptable salt thereof includes a formula of:

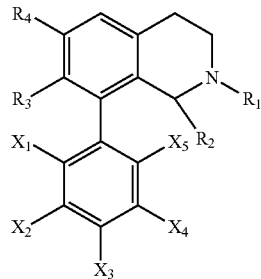

wherein $R_1$ is one selected from a group consisting of hydrogen, $C_{1-12}$ linear chain alkyl group, $C_{1-12}$ branched chain alkyl group, $(CH_2)_n(\text{Hete})R_{10}R_{11}R_{12}$ and $(CH_2)_n ArR_{10}R_{11}R_{12}$, wherein the n is an integer from 1 to 6, Hete is a heterocyclic group, and $R_{10}$, $R_{11}$ and $R_{12}$ are independently selected from a group consisting of hydrogen, halo group, nitro group, amino group, cyano group, acetyl group, $C_{1-6}$ linear chain saturated alkyl group, $C_{1-6}$ linear chain saturated alkoxy group and $C_{1-6}$ linear chain saturated haloalkyl group;

$R_2$ is one of a hydrogen and a $C_{1-6}$ linear chain saturated alkyl group;

$R_3$ is one of a hydroxyl group and a $C_{1-6}$ linear chain saturated alkoxy group;

$R_4$ is one of a hydroxyl group and a $C_{1-6}$ linear chain saturated alkoxy group; and $X_1$, $X_2$, $X_3$, $X_4$ and $X_5$ are independently selected from a group consisting of hydrogen, halo group, nitro group, amino group, cyano group, acetyl group, $C_{1-6}$ linear chain saturated alkyl group, $C_{1-6}$ branched chain saturated alkyl group, $C_{1-6}$ linear chain saturated alkoxy group, $C_{1-6}$ branched chain saturated alkoxy group, $C_{1-6}$ linear chain saturated alkylthio group, $C_{1-6}$ branched chain saturated alkylthio group, $C_{1-6}$ linear chain saturated haloalkyl group and $C_{1-6}$ branched chain saturated haloalkyl group.

In accordance with a further aspect of the present invention, a pharmaceutical composition is provided. The pharmaceutical composition is provided includes: a pharmaceutically acceptable carrier; and a therapeutically effective amount of a compound having a formula of:

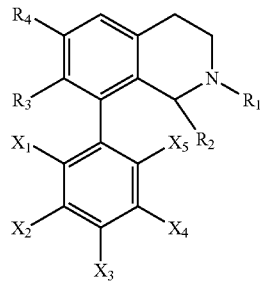

wherein $R_1$ is one selected from a group consisting of hydrogen, $C_{1-12}$ linear chain alkyl group, $C_{1-12}$ branched chain alkyl group, $(CH_2)_n(\text{Hete})R_{10}R_{11}R_{12}$ and $(CH_2)_n$ ArR$_{10}$R$_{11}$R$_{12}$, wherein the n is an integer from 1 to 6, Hete is a heterocyclic group, and R$_{10}$, R$_{11}$ and R$_{12}$ are independently selected from a group consisting of hydrogen, halo group, nitro group, amino group, cyano group, acetyl group, C$_{1-6}$ linear chain saturated alkyl group, C$_{1-6}$ linear chain saturated alkoxy group and C$_{1-6}$ linear chain saturated haloalkyl group;

R$_2$ is one of a hydrogen and a C$_{1-6}$ linear chain saturated alkyl group;

R$_3$ is one of a hydroxyl group and a C$_{1-6}$ linear chain saturated alkoxy group;

R$_4$ is one of a hydroxyl group and a C$_{1-6}$ linear chain saturated alkoxy group; and X$_1$, X$_2$, X$_3$, X$_4$ and X$_5$ are independently selected from a group consisting of hydrogen, halo group, nitro group, amino group, cyano group, acetyl group, C$_{1-6}$ linear chain saturated alkyl group, C$_{1-6}$ branched chain saturated alkyl group, C$_{1-6}$ linear chain saturated alkoxy group, C$_{1-6}$ branched chain saturated alkoxy group, C$_{1-6}$ linear chain saturated alkylthio group, C$_{1-6}$ branched chain saturated alkylthio group, C$_{1-6}$ linear chain saturated haloalkyl group and C$_{1-6}$ branched chain saturated haloalkyl group.

The excipient or "pharmaceutically acceptable carrier or excipient" or "bioavailable carrier or excipient" includes solvent, dispersant, coating, antimicrobial agent, antifungal agent to preserve or delay-absorbed agent and any other known compound to prepare formulation. In general, these carrier or excipient themselves do not have activity of treating disease. The derivatives disclosed in the present invention in combination with pharmaceutically acceptable carrier or excipient, preparing formulation do not cause adverse effect, allergy or other inappropriate reaction of animals or humans. Therefore, the derivatives disclosed in the present invention in combination with pharmaceutically acceptable carrier or excipient could be applied to human clinically. The formulation of the present invention compound could achieve therapeutic effect through intravenous injection, oral administration, inhalation or through local administration of nose, rectum, vagina or hypoglottis. The 0.1 mg to 100 mg of an active ingredient per day is administrated for different disease of patients.

The carrier is different with different formulation. The composition for sterile injection could be suspended in sterile intravenous injection diluents or solvents, such as 1,3-butanediol. The acceptable carrier could be mannitol or water. In addition, the oil fixed or synthesized monoglyceride/diglyceride suspension medium are commonly used solvents. Fatty acids, such as oleic acid, olive oil, castor oil, glyceride derivatives, especially the polyoxyethylenated form could be prepared for injection and natural pharmaceutically acceptable oil. These oil solution or suspension include long-chain alcohol diluents, dispersant, carboxymethyl cellulose or similar dispersant. Other surfactants for common use include Tween, Spans, other similar emulsifier, pharmaceutically acceptable solid for pharmaceutical manufacture industry, liquid, or other bioavailable enhancer for formulation development.

The composition for oral administration is adapted to oral acceptable formulation, wherein the types include capsule, lozenge, troche, emulsifier, liquid suspension, dispersant and solvent. The common carrier used for oral administration such as lozenge, for example, could be lactose, corn starch, lubricant, magnesium stearate as basic additives. The diluents used for capsule include lactose, dry corn starch. The preparation for liquid suspension or emulsifier formulation is to suspend or dissolve active ingredients with binding emulsifiers or oil interface of suspending agent. The sweetening agents, flavoring agent or coloring matter.

The aerosol sprayer for oral use or inhalation composition is prepared by known formulation technologies. For example, the composition is dissolved in physiological saline, added with benzyl alcohol, other suitable preservative or absorbefacient to enhance bioavailable properties. The composition of the present invention compound could also be prepared to suppository which is administrated through rectum or vagina.

The injections include hypodermic, peritoneal cavity, vein, muscle, joint cavity, intracranial, synovial fluid, intrathecal injection, aorta injection, thoracic injection, lesion injection or other suitable administration technologies.

The above aspects and advantages of the present invention will become apparent to those ordinarily skilled in the art after reviewing the following detailed descriptions and accompanying drawing.

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

The present invention provides a library of novel derivatives of 8-phenylisoquinoline. The synthesis includes the following 6 schemes.

Figure 1:
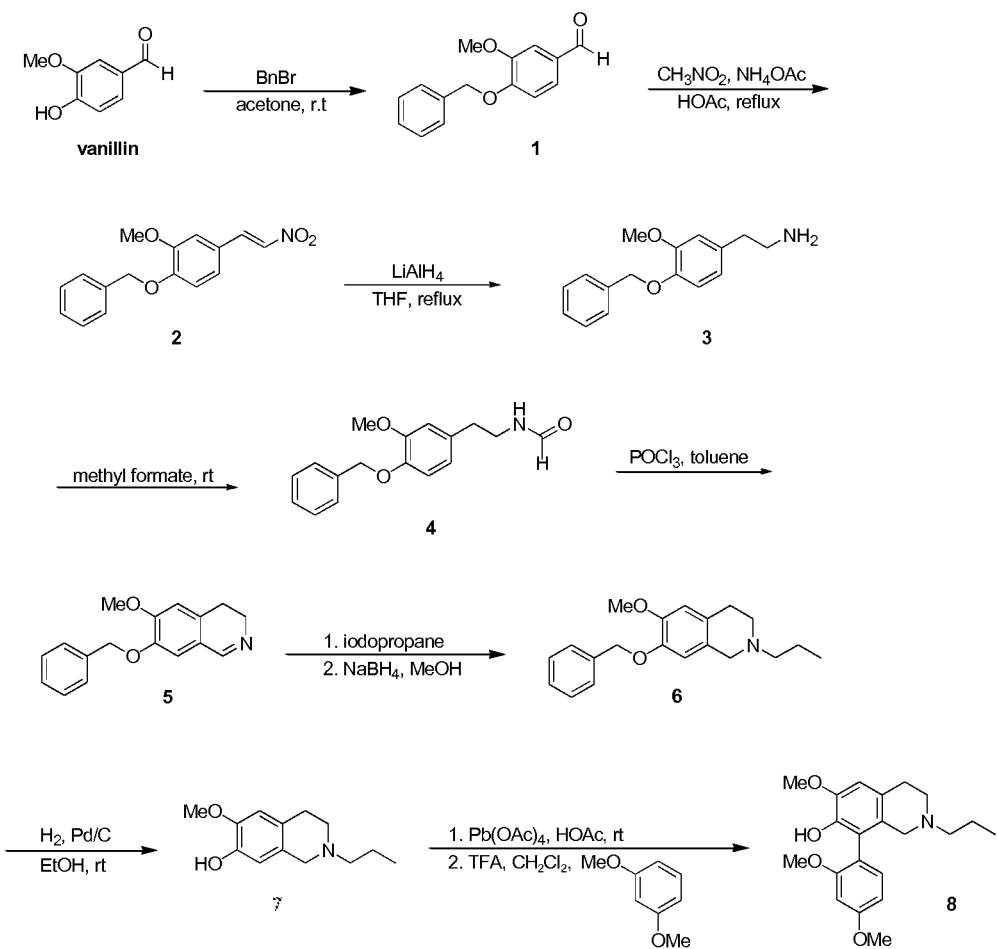
FIG. 1 shows the synthetic scheme 1 of novel derivatives of 8-phenylisoquinoline.

Scheme 1 (FIG. 1): Protection of the hydroxyl group in vanillin with benzyl bromide yielded aldehyde 1 is shown in Scheme 1. Henry reaction between aldehyde 1 and nitromethane gave nitrostyrene 2. Reduction of compound 2 with lithium aluminum hydride in tetrahydrofuran (THF) afforded amine 3. The reaction of amine 3 with an excess amount of methyl formate provided formamide 4. Cyclization of amide 4 using phosphorus oxychloride (POCl$_3$) via Bischler-Napieralski reaction obtained 3,4-dihydroisoquinoline 5. Alkylation of compound 5 with iodopropane followed by NaBH$_4$ reduction produced tetrahydroisoquinoline 6 in high yield. Catalytic hydrogenation over Pd/C removed the protective groups of 6 to afford 1,2,3,4-tetrahydroisoquinolin-7-ol 7 in quantitative yield. Treatment of compound 7 with Pb(OAc)$_4$ in acetic acid followed by acid-catalyzed aromatic substitution with 1,3-dimethoxybenzene using trifluoroacetic acid (TFA) furnished 8-phenyl-tetrahydroisoquinolin-7-ol 8.

Figure 2:
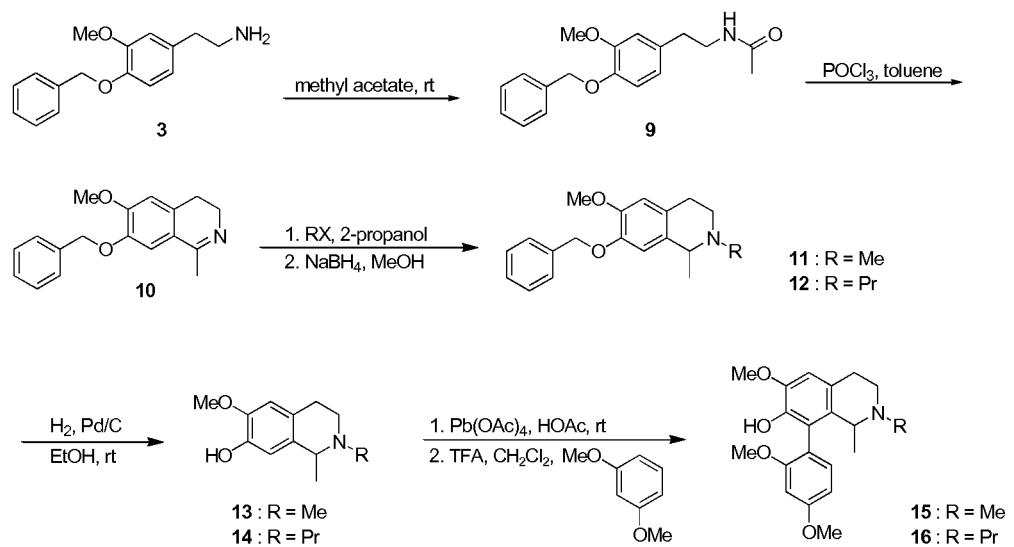
FIG. 2 shows the synthetic scheme 2 of novel derivatives of 8-phenylisoquinoline.

Scheme 2 (FIG. 2): The 1-methyl-substituted 8-phenyl-tetrahydroisoquinolin-7-ol derivatives were synthesized starting from amine 3. Treatment of 3 with an excess amount of methyl acetate yielded acetamide 9, which was then converted to 3,4-dihydroisoquinoline 10 using POCl$_3$. N-Alkylation of 10 with alkyl halides followed by NaBH$_4$ reduction obtained tetrahydroisoquinolines 11 and 12. The benzyl protecting groups of 11 and 12 were then removed by catalytic hydrogenation to provide phenols 13 and 14, respectively as shown in Scheme 2. Treatment of 13 and 14 with Pb(OAc)$_4$ in acetic acid followed by acid-catalyzed aromatic substitution with 1,3-dimethoxybenzene using TFA afforded 1-methyl-8-phenyl-tetrahydroisoquinolin-7-ols 15 and 16, respectively.

Figure 3:
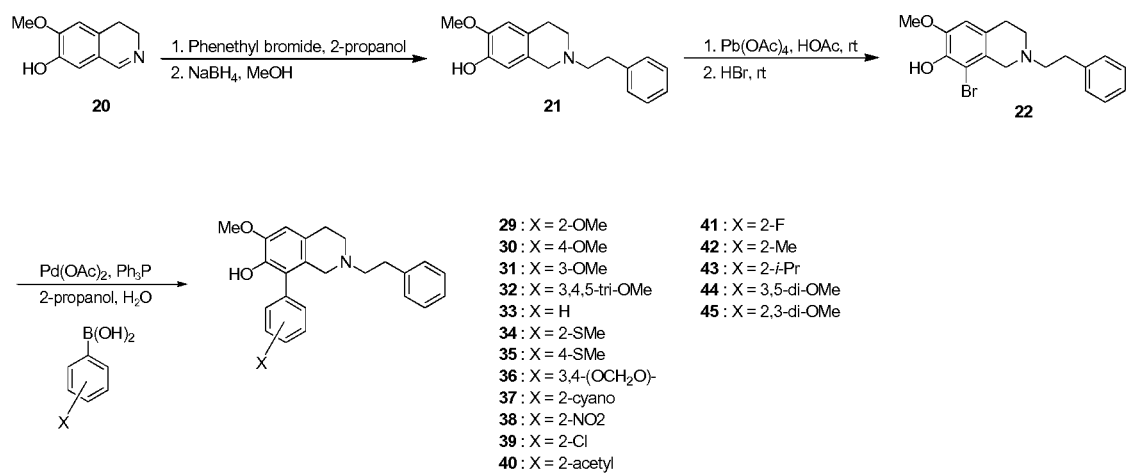
FIG. 3 shows the synthetic scheme 3 of novel derivatives of 8-phenylisoquinoline.

Scheme 3 (FIG. 3): The N-phenylethyl-substituted 8-phenyl-tetrahydroisoquinolin-7-ol derivatives were synthesized starting from the commercially available 7-hydroxy-6-methoxy-3,4-dihydroisoquinoline (20) as depicted in Scheme 3. N-alkylation of compound 20 with phenylethyl bromide followed by NaBH$_4$ reduction provided amine 21. Treatment of phenethylamine 21 with Pb(OAc)$_4$ followed by aromatic substitution with HBr produced 8-bromo-tetrahydroisoquinoline 22. The desired target compounds 29-45 were then synthesized from 22 with various substituted-arylboranes using Suzuki coupling reaction condition in moderate yields.

Figure 4:
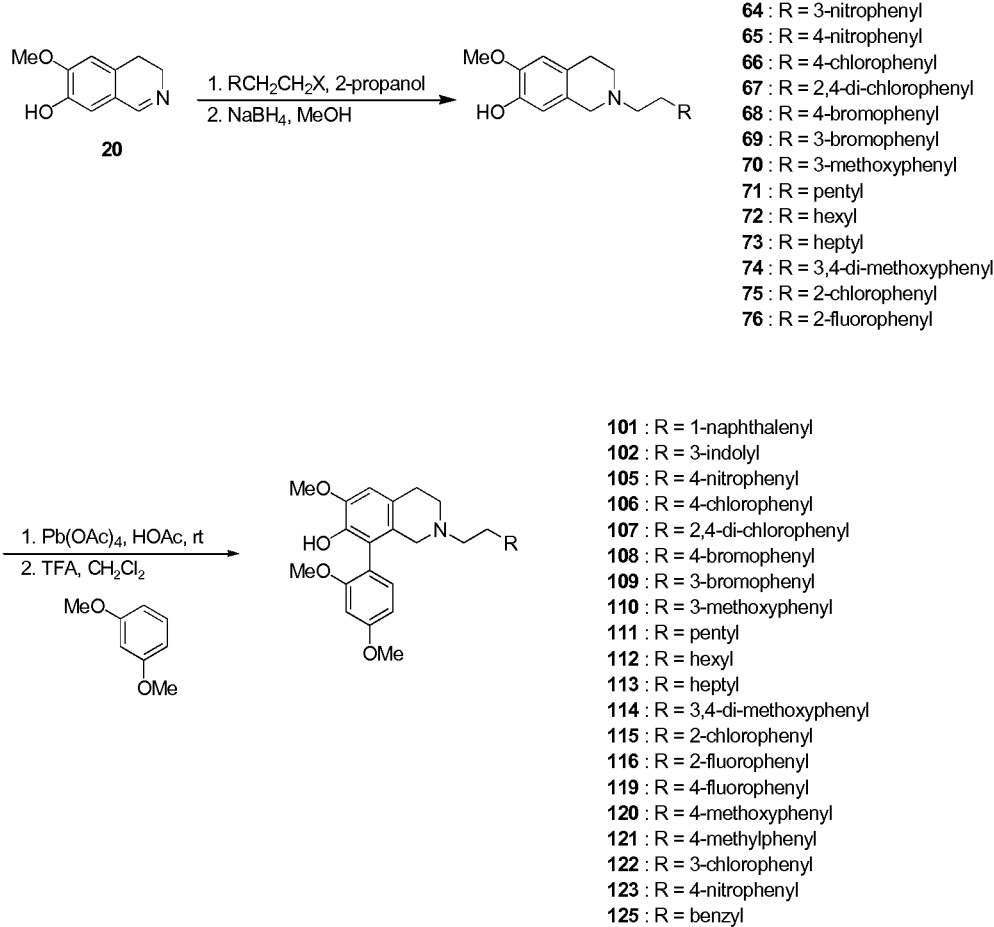
FIG. 4 shows the synthetic scheme 4 of novel derivatives of 8-phenylisoquinoline.

Scheme 4 (FIG. 4): The N-substituted 8-(2,4-dimethoxyphenyl)-tetrahydroisoquinolin-7-ols were also prepared starting from the commercially available compound 20 as shown in Scheme 4. Treatment of compound 20 with various halides followed by NaBH$_4$ reduction yielded N-substituted tetrahydroisoquinolin-7-ols 61-76. Oxidation of compounds 61-76 with Pb(OAc)$_4$ in acetic acid followed by TFA-catalyzed aromatic substitution with 1,3-dimethoxybenzene afforded the corresponding N-substituted 8-(2,4-dimethoxyphenyl)-6-methoxy-tetrahydroisoquinolin-7-ols 101-125, respectively.

Figure 5:
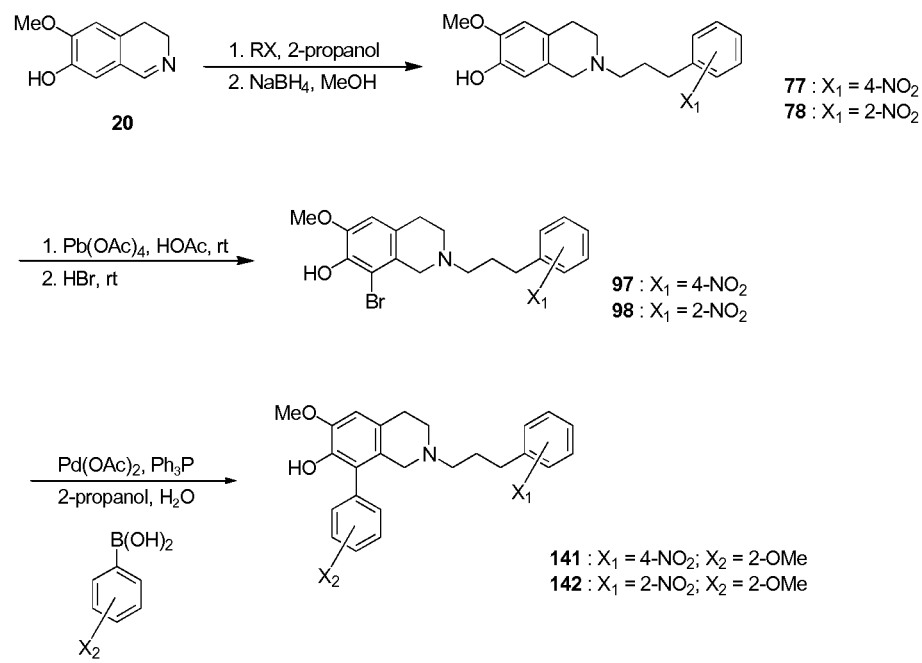
FIG. 5 shows the synthetic scheme 5 of novel derivatives of 8-phenylisoquinoline.

Scheme 5 (FIG. 5): Treatment of compound 20 with various 3-phenylpropyl bromides followed by NaBH$_4$ reduction provided the corresponding N-3-phenylpropyl-substituted tetrahydroisoquinolin-7-ol derivatives 77 and 78 as depicted in Scheme 5. Bromides 97 and 98 were obtained by treatment of compounds 77 and 78 with Pb(OAc)$_4$ followed by aromatic substitution with HBr, respectively. Aryl coupling reaction of compounds 97 and 98 under Suzuki reaction condition with various substituted-arylboranes afforded the N-3-phenylpropyl-substituted 6-methoxy-8-phenyl-tetrahydroisoquinolin-7-ols 141 and 142 in moderate yields, respectively.

Figure 6:
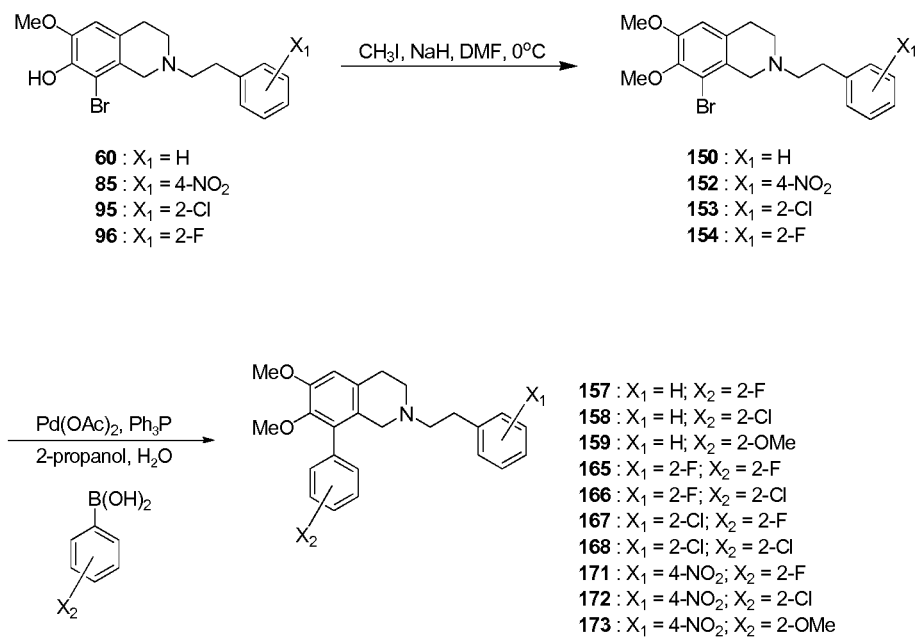
FIG. 6 shows the synthetic scheme 6 of novel derivatives of 8-phenylisoquinoline.

Scheme 6 (FIG. 6): The N-phenylethyl-substituted 6,7-dimethoxy-8-phenyl-tetrahydroisoquinoline derivatives 157-173 were prepared using N-phenylethyl-substituted 8-bromo-6-methoxy-tetrahydroisoquinolin-7-ols 60-96 as depicted in Scheme 6. O-Methylation of phenols 60-96 with methyl iodide in the presence of NaH gaves 6,7-dimethoxy-tetrahydroisoquinolines 150-154, respectively. Aryl coupling reaction of compounds 150-154 with various substituted-arylboranes under Suzuki reaction condition furnished 6,7-dimethoxy-8-phenyl-tetrahydroisoquinolines 157-173, respectively.

The specific synthesizing steps of the compounds from the above schemes 1-6 are as follows:

Compound 7: A mixture of compound 5 (500 mg, 1.87 mmol), C$_3$H$_7$Br (0.51 mL, 5.63 mmol), and 2-propanol (17 mL) was refluxed for 16 hours. The resulting solution was concentrated and MeOH (25 mL) was added to dissolve the residue. The solution was cooled in an ice-bath and then NaBH$_4$ (167 mg, 4.41 mmol) was added slowly under N$_2$. The mixture was stirred for another 10 minutes and then concentrated. The residue was treated with H$_2$O and CHCl$_3$ (35 mL), and then the organic layer was washed with brine, dried over MgSO$_4$, filtered, and evaporated. The crude residue was chromatographed (silica gel, EtOAc/n-hexane=1:2) to afford compound 6 as a pale yellow solid (442 mg, 1.42 mmol, 76%), which was used in the following reaction without further purification. A mixture of compound 6 (431 mg, 1.38 mmol) and 10% Pd/C (160 mg) in EtOAc (8.5 mL) was stirred under H$_2$ (1 atm) for 2 hours, and the catalyst was removed by filtration with the aid of Celite. The filtrate was concentrated and the crude residue was chromatographed (silica gel, MeOH/CH$_2$Cl$_2$=1:100) to obtain compound 7 as a pale solid (266 mg, 1.20 mmol, 87%).

Compound 21: A mixture of compound 20 (100 mg, 0.56 mmol), 2-phenylethyl bromide (311 mg, 1.68 mmol), and 2-propanol (3.5 mL) was refluxed for 15 hours. The resulting solution was concentrated and MeOH (5 mL) was added to dissolve the residue. The solution was cooled in an ice-bath and then NaBH$_4$ (49 mg, 1.29 mmol) was added slowly under N$_2$. The mixture was stirred for another 10 minutes and then concentrated. The residue was treated with H$_2$O (20 mL) and CHCl$_3$ (20 mL), and then the organic layer was washed with brine, dried over MgSO$_4$, filtered, and evaporated. The crude residue was chromatographed (silica gel, MeOH/CH$_2$Cl$_2$=1/100) to afford compound 21 as a white solid (146 mg, 0.52 mmol, 92%).

Compound 30: To a solution of C$_{18}$H$_{20}$BrNO$_2$ (50 mg, 0.14 mmol) in 2-propanol (2.0 mL) in a 10-mL thick walled Pyrex reaction vessel, 4-methoxyphenylboronic acid (26 mg, 0.19 mmol) was added. After stirring for 30 min, Pd(OAc)$_2$ (1.3 mg, 0.006 mmol), PPh$_3$ (4.7 mg, 0.02 mmol), 2 M Na$_2$CO$_{3(aq)}$ (0.09 mL, 0.17 mmol), and H$_2$O (0.1 mL) were added. Then the mixture was heated at 140° C. for 10 min in a microwave synthesizer, and H$_2$O (0.35 mL) was added before cooling to room temperature. The resulting solution was diluted with H$_2$O (5 mL) and extracted with EtOAc (5 mL). The organic layer was washed with 5% NaHCO$_{3(aq)}$ and brine. The organic solution was treated with Darco G-60 (100 mg) and stirred at room temperature for 30 min, and then dried over MgSO$_4$, filtered (the sintered glass funnel was charged with Celite to a depth of 1 cm and Florisil was spread evenly on the top of the Celite), and evaporated. The crude residue was chromatographed (silica gel, EtOAc/n-hexane=2/1) to afford an orange oil (40 mg, 0.10 mmol, 73%).

Compounds 29 and 31-40: Table 1 is a parameter table. "Parameter 1" is added into the reaction vessel for microwave-assisted heating and dissolved with "parameter 2" mL 2-propanol. The appearance of solution is "parameter 3" and the reagent "parameter 4" is added thereinto, and stirred for "parameter 5" minutes. The appearance of resulting solution is "parameter 6". The Pd(OAc)$_2$ "parameter 7", PPh$_3$ "parameter 8", 2 M Na$_2$CO$_3$(aq) "parameter 9" and "parameter 10" mL H$_2$O are added and heated "parameter 11". Before the temperature of the solution is decreased, "parameter 12" mL H$_2$O is added, stirred in the air until reaching room temperature, diluted with "parameter 13" mL EtOAc, and extracted with "parameter 14" mL H$_2$O. The organic layer is washed with 5% NaHCO$_3$(aq), washed with brine, added in "parameter 15" mg Darco G-60, stirred for "parameter 16" minutes, added in MgSO$_4$ for drying, stirred for "parameter 17" minutes, filtered by the sintered glass funnel covered with about 1 cm of Celite and a thin layer of Florisil, concentrated for drying and purified by flash column chromatography (silica gel, "parameter 18") to obtain "parameter 19".

TABLE 1

The parameter table for the synthesis of compounds 29 and 31-40

| | 29 | 31 | 32 | 33 | 34 | 35 |
|---|---|---|---|---|---|---|
| 1 | 2-methoxyphenylboronic acid (65 mg, 0.43 mmol) | $C_{18}H_{20}BrNO_2$ (100 mg, 0.28 mmol) | $C_{18}H_{20}BrNO_2$ (150 mg, 0.41 mmol) | phenylboronic acid (43 mg, 0.35 mmol) | 2-(methylthio)phenyl-boronic acid (59 mg, 0.35 mmol) | 4-(methylthio)phenyl-boronic acid (125 mg, 0.74 mmol) |
| 2 | 2.0 | 2.0 | 2.0 | 2.0 | 2.0 | 3.0 |
| 3 | transparent colorless | — | — | — | transparent light yellow | transparent colorless |
| 4 | $C_{18}H_{20}BrNO_2$ (100 mg, 0.28 mmol) | 3-methoxyphenyl-boronic acid (62 mg, 0.41 mmol) | 3,4,5-trimethoxy-benzeneboronic acid (106 mg, 0.50 mmol) | $C_{18}H_{20}BrNO_2$ (100 mg, 0.28 mmol) | $C_{18}H_{20}BrNO_2$ (100 mg, 0.28 mmol) | $C_{18}H_{20}BrNO_2$ (150 mg, 0.41 mmol) |
| 5 | 30 | 30 | 10 | 30 | 30 | 25 |
| 6 | turbid dirt yellow | turbid beige white | turbid beige white | turbid beige white | turbid orange yellow | turbid white |
| 7 | 2.5 mg, 0.011 mmol | 1.2 mg, 0.005 mmol | 1.9 mg, 0.008 mmol | 1.9 mg, 0.008 mmol | 2.2 mg, 0.01 mmol | 2.7 mg, 0.01 mmol |
| 8 | 5.6 mg, 0.021 mmol | 3.1 mg, 0.01 mmol | 5.2 mg, 0.02 mmol | 5.4 mg, 0.02 mmol | 7.0 mg, 0.027 mmol | 10 mg, 0.04 mmol |
| 9 | 0.18 mL, 0.34 mmol | 0.18 mL, 0.34 mmol | 0.27 mL, 0.50 mmol | 0.18 mL, 0.34 mmol | 0.17 mL, 0.34 mmol | 0.25 mL, 0.49 mmol |
| 10 | 0.2 | 0.2 | 0.3 | 0.2 | 0.2 | 0.3 |
| 11 | 120° C. for 20 minutes | 120° C. for 10 minutes | 120° C. for 10 minutes | 120° C. for 10 minutes | 140° C. for 20 minutes | 140° C. for 20 minutes |
| 12 | 0.7 | 0.7 | 1.0 | 0.7 | 0.7 | 1.1 |
| 13 | 10 | 5 | 10 | 10 | 20 | 20 |
| 14 | 10 | 0 | 0 | 0 | 10 | 20 |
| 15 | 100 | 100 | 150 | 117 | 106 | 180 |
| 16 | 5 | 30 | 5 | 15 | 20 | 10 |
| 17 | 10 | 30 | 10 | 10 | 10 | 10 |
| 18 | EA/n-hexane = 1/1 | EA/n-hexane = 1/1 | EA/n-hexane = 1/1 | EA/n-hexane = 1/3 | EA/n-hexane = 1/2 | EA/n-hexane = 1/2 |
| 19 | orange yellow oil products (106 mg, 0.27 mmol, 97%) | light yellow oil products (97 mg, 0.23 mmol, 83%) | light yellow oil products (102 mg, 0.23 mmol, 55%) | light yellow oil products (90 mg, 0.25 mmol, 89%) | orange oil products (66 mg, 0.16 mmol, 58%) | orange oil products (148 mg, 0.37 mmol, 89%) |

| | 36 | 37 | 38 | 39 | 40 |
|---|---|---|---|---|---|
| 1 | 3,4-(methylenedioxy)benzene boronic acid (86 mg, 0.52 mmol) | 2-cyanophenylboronic acid (74 mg, 0.50 mmol) | 2-nitrophenylboronic acid (124 mg, 0.74 mmol) | 2-chlorophenylboronic acid (77 mg, 0.49 mmol) | 2-acetylphenylboronic acid (80 mg, 0.49 mmol) |
| 2 | 3.0 | 3.0 | 3.0 | 3.0 | 3.0 |
| 3 | transparent light orange | transparent light yellow | transparent light yellow | transparent colorless | turbid white |
| 4 | $C_{18}H_{20}BrNO_2$ (150 mg, 0.41 mmol) | $C_{18}H_{20}BrNO_2$ (151 mg, 0.42 mmol) | $C_{18}H_{20}BrNO_2$ (152 mg, 0.42 mmol) | $C_{18}H_{20}BrNO_2$ (150 mg, 0.41 mmol) | $C_{18}H_{20}BrNO_2$ (149 mg, 0.41 mmol) |
| 5 | 30 | 35 | 30 | 25 | 30 |
| 6 | turbid beige white | turbid white | turbid light yellow | turbid beige white | turbid beige yellow |
| 7 | 3.0 mg, 0.01 mmol | 3.0 mg, 0.01 mmol | 4 mg, 0.018 mmol | 3.0 mg, 0.01 mmol | 3.0 mg, 0.012 mmol |
| 8 | 11 mg, 0.04 mmol | 10 mg, 0.037 mmol | 16 mg, 0.06 mmol | 11 mg, 0.042 mmol | 10 mg, 0.037 mmol |
| 9 | 0.25 mL, 0.49 mmol | 0.25 mL, 0.49 mmol | 0.37 mL, 0.74 mmol | 0.25 mL, 0.49 mmol | 0.25 mL, 0.50 mmol |
| 10 | 0.3 | 0.3 | 0.3 | 0.3 | 0.3 |
| 11 | 140° C. for 20 minutes | 140° C. for 20 minutes | 120° C. for 20 minutes | 140° C. for 20 minutes | 140° C. for 20 minutes |
| 12 | 1.1 | 1.1 | 1.1 | 1.1 | 1.1 |
| 13 | 20 | 20 | 20 | 20 | 20 |
| 14 | 20 | 20 | 20 | 20 | 20 |
| 15 | 197 | 195 | 176 | 160 | 150 |
| 16 | 10 | 10 | 10 | 10 | 10 |
| 17 | 10 | 10 | 10 | 10 | 10 |
| 18 | EA/n-hexane = 1/3 | EA/n-hexane = 1/3 | EA/n-hexane = 1/2 | EA/n-hexane = 1/2 | EA/n-hexane = 1/2 |
| 19 | white solid products (134 mg, 0.33 mmol, 81%) | light yellow oil products (33 mg, 0.09 mmol, 20%) | light yellow oil products (20 mg, 0.05 mmol, 12%) | light yellow oil products (105 mg, 0.27 mmol, 65%) | white solid products (40 mg, 0.10 mmol, 24%) |

Compound 44: To a solution of $C_{18}H_{20}BrNO_2$ (100 mg, 0.28 mmol) in 2-propanol (1.5 mL) in a 10-mL thick walled Pyrex reaction vessel, 3,5-dimethoxybenzeneboronic acid (62 mg, 0.34 mmol) was added. After stirring for 30 min, Pd(OAc)$_2$ (2.2 mg, 0.01 mmol), PPh$_3$ (8.0 mg, 0.03 mmol), 2 M Na$_2$CO$_{3(aq)}$ (0.17 mL, 0.34 mmol), and H$_2$O (0.7 mL) were added. Then the mixture was heated at 140° C. for 10 min in a microwave synthesizer, and H$_2$O (0.35 mL) was added before cooling to room temperature. The resulting solution was diluted with H$_2$O (10 mL) and extracted with EtOAc (10 mL). The organic layer was washed with 5% NaHCO$_{3(aq)}$ (10 mL) and brine. The organic solution was treated with Darco G-60 (100 mg) and stirred at room temperature for 30 min, and then dried over MgSO$_4$, filtered (the sintered glass funnel was charged with Celite to a depth of 1 cm and Florisil was spread evenly on the top of the Celite), and evaporated. The crude residue was chromatographed (silica gel, EtOAc/n-hexane=1/1) to afford a yellow oil (76 mg, 0.18 mmol, 65%).

Compound 45: To a solution of $C_{18}H_{20}BrNO_2$ (100 mg, 0.28 mmol) in 2-propanol (2.0 mL) in a 10-mL thick walled Pyrex reaction vessel, 2,3-dimethoxyphenylboronic acid (62 mg, 0.34 mmol) was added. After stirring for 30 min, Pd(OAc)$_2$ (2.0 mg, 0.009 mmol), PPh$_3$ (3.7 mg, 0.014 mmol), 2 M Na$_2$CO$_{3(aq)}$ (0.18 mL, 0.36 mmol), and H$_2$O (0.2 mL) were added. Then the mixture was heated at 120° C. for 10 min in a microwave synthesizer, and H$_2$O (0.7 mL) was added before cooling to room temperature. The resulting solution was diluted with H$_2$O (5 mL) and extracted with EtOAc (5 mL). The organic layer was washed with 5% NaHCO$_{3(aq)}$ (5 mL) and brine. The organic solution was treated with Darco G-60 (100 mg) and stirred at room temperature for 30 min, and then dried over MgSO$_4$, filtered (the sintered glass funnel was charged with Celite to a depth of 1 cm and Florisil was spread evenly on the top of the Celite), and evaporated. The crude residue was chromatographed (silica gel, EtOAc/n-hexane=1/1) to afford a yellow oil (82 mg, 0.20 mmol, 71%).

Compounds 60, 85 and 95-98: Table 2 is a parameter table. The starting material "parameter 1" is added into a reaction flask at room temperature under N$_2$, and "parameter 2" mL HOAc is added thereto. The Pb(OAc)$_4$ "parameter 3" is added, and then the solution is "parameter 4", poured into the conical flask and added with "parameter 5" mL Na$_2$CO$_3$ (sat) slowly. The pH of the aqueous layer is alkaline (pH="parameter 6"). The solids produced in neutralization is filtered. The filter cake is washed with CH$_2$Cl$_2$. The filtrate is extracted with "parameter 7" mL CH$_2$Cl$_2$. The organic layer is washed with brine, added with MgSO$_4$ for drying, stirred for 5 minutes, filtered with the sintered glass funnel and concentrated for drying to obtain "parameter 8" product. The crude product was used in the following reaction without further purification.

The solution which is added in HBr "parameter 9" in the room temperature air and the appearance of the solution is "parameter 10". After stirring for "parameter 11" hours, "parameter 12" mL Na$_2$CO$_3$ (sat) and "parameter 13" mL CH$_2$Cl$_2$ are added slowly to the solution. The pH of the aqueous layer is alkaline (pH="parameter 14"), and then the "parameter 15" mL CH$_2$Cl$_2$ and "parameter 16" mL H$_2$O are added for extraction. The organic layer is washed with brine, added with MgSO$_4$ for drying, stirred for 5 minutes, filtered with the sintered glass funnel and concentrated for drying to obtain crude product "parameter 17" mg. The "parameter 19" is afforded after flash column chromatography (silica gel, "parameter 18").

TABLE 2

The parameter table for the synthesis of compounds 60, 85 and 95-98

| | 60 | 85 | 95 | 96 | 97 | 98 |
|---|---|---|---|---|---|---|
| 1 | $C_{18}H_{21}NO_2$ (351 mg, 1.24 mmol) | $C_{18}H_{20}N_2O_4$ (503 mg, 1.53 mmol) | $C_{18}H_{20}ClNO_2$ (1000 mg, 3.15 mmol) | $C_{18}H_{20}FNO_2$ (1002 mg, 3.32 mmol) | $C_{19}H_{22}N_2O_4$ (320 mg, 0.93 mmol) | $C_{19}H_{22}N_2O_4$ (285 mg, 0.83 mmol) |
| 2 | 6.2 | 7.6 | 15.5 | 16.5 | 4.7 | 4.2 mL |
| 3 | 830 mg, 1.87 mmol | 1034 mg, 2.33 mmol | 2101 mg, 4.74 mmol | 2262 mg, 5.10 mmol | 636 mg, 1.43 mmol | 562 mg, 1.27 mmol |
| 4 | deep red coffee color | transparent red coffee color | transparent deep red brown | transparent burgundy red | red brown | tranparent red brown |
| 5 | 40 | 60 | 100 | 130 | 25 | 25 |
| 6 | 8-9 | 8-9 | 8-9 | 8-9 | 8-9 | 8-9 |
| 7 | 50 | 80 | 100 | 130 | 40 | 40 |
| 8 | deep orange red solid (282 mg, 0.83 mmol) | red brown solid (498 mg, 1.29 mmol) | red brown solid (1089 mg, 2.91 mmol) | red brown solid (1088 mg, 3.04 mmol) | deep orange red solid (303 mg, 0.76 mmol) | brown oil (263 mg, 0.66 mmol) |
| 9 | 6 mL, 48% wt | 10 mL, 48% wt | 15 mL, 48% wt | 15 mL, 48% wt | 5 mL, 48% wt | 5 mL, 48% wt |
| 10 | turbid yellow | turbid orange | turbid orange | turbid orange | turbid orange | turbid orange |
| 11 | 3 | 2 | 1.5 | 1.5 | 1 | 0.5 |
| 12 | 35 | 70 | 100 | 100 | 35 | 35 |
| 13 | 20 | 50 | 50 | 50 | 20 | 20 |
| 14 | 8-9 | 8-9 | 9-10 | 9-10 | 8-9 | 8-9 |
| 15 | 15 | 50 | 80 | 60 | 20 | 50 |
| 16 | 0 | 30 | 30 | 10 | 0 | 0 |
| 17 | 344 | 433 | 1013 | 973 | 225 | 195 |
| 18 | EA/n-hexane = 1/2 | EA/n-hexane = 1/1 | MeOH/CH$_2$Cl$_2$ = 1/100 | EA/n-hexane = 1/3 | MeOH/CH$_2$Cl$_2$ = 1/100 | MeOH/CH$_2$Cl$_2$ = 1/90 |
| 19 | beige white solid products (260 mg, 0.72 mmol, 58%) | yellow solid products (363 mg, 0.89 mmol, 59%) | white solid products (747 mg, 1.88 mmol, 60%) | white solid products (752 mg, 1.98 mmol, 60%) | orange yellow oil products (179 mg, 0.42 mmol, 46%) | orange yellow oil products (170 mg, 0.40 mmol, 49%) |

Compounds 63-67, 67-70 and 74-78: Table 3 is a parameter table. The starting material "parameter 1" is added into a flask at room temperature under N$_2$, and then the "parameter 2" mL IPA and "parameter 3" are added thereinto. The starting material is dissolved at "parameter 4" ° C. The appearances of reaction solution are "parameter 5" and "parameter 7" in about "parameter 6" minutes, and then the solution is heated at 110~120° C. for "parameter 8" hours and concentrated in room temperature. The "parameter 9" mL MeOH is added and the resulting mixture is stirred for "parameter 10" minutes. To the solution which is "parameter 11" in a ice-bath, is added NaBH$_4$(s) "parameter 12" slowly under N$_2$ and stirred for "parameter 13" minutes. The solution which is "parameter 14" is added with "parameter 15" mL H$_2$O and extracted with "parameter 16" mL CHCl$_3$. The organic layer is added with MgSO$_4$ for drying, stirred for "parameter 17" minutes, filtered, and concentrated to obtain "parameter 18". The "parameter 20" is afforded after flash column chromatography (silica gel, "parameter 19").

TABLE 3

The parameter table for the synthesis of compounds 63-67, 67-70 and 74-78

| | 63 | 64 | 65 | 66 | 67 | 69 |
|---|---|---|---|---|---|---|
| 1 | $C_{10}H_{11}NO_2$ (20, 300 mg, 1.69 mmol) | $C_{10}H_{11}NO_2$ (20, 300 mg, 1.69 mmol) | $C_{10}H_{11}NO_2$ (20, 1001 mg, 5.65 mmol) | $C_{10}H_{11}NO_2$ (20, 301 mg, 1.70 mmol) | $C_{10}H_{11}NO_2$ (20, 300 mg, 1.69 mmol) | $C_{10}H_{11}NO_2$ (20, 300 mg, 1.69 mmol) |
| 2 | 10 | 10 | 35 | 14 | 10 | 10 |
| 3 | $C_8H_8NO_2Br$ (1127 mg, 4.89 mmol) | $C_8H_8NO_2Br$ (866 mg, 3.76 mmol) | $C_8H_8NO_2Br$ (3810 mg, 16.56 mmol) | 4-chlorophenethyl bromide (1115 mg, 5.08 mmol) | $C_8H_7BrCl_2$ (1.00 g, 3.94 mmol) | $C_8H_8Br_2$ (1.00 g, 3.79 mmol) |
| 4 | 60 | 75 | — | 80 | 80 | 80 |
| 5 | transparent light yellow | transparent light yellow | — | transparent yellow | transparent yellow | transparent yellow |
| 6 | 30 | 10 | — | 120 | 120 | 90 |
| 7 | turbid yellow | turbid yellow | transparent orange yellow | turbid yellow | turbid yellow | turbid yellow |
| 8 | 18 | 16 | 17 | 24 | 25 | 19 |
| 9 | 15 | 15 | 35 | 15 | 15 | 15 |
| 10 | 10 | 10 | 10 | 10 | 10 | 10 |
| 11 | turbid yellow | turbid yellow | — | transparent yellow | transparent yellow | transparent yellow |
| 12 | 264 mg, 6.97 mmol | 206 mg, 3.39 mmol | 853 mg, 22.53 mmol | 576 mg, 15.2 mmol | 257 mg, 6.78 mmol | 270 mg, 7.14 mmol |
| 13 | 20 | 20 | 10 | 20 | 20 | 20 |
| 14 | turbid yellow | turbid orange | — | opaque orange | opaque orange | opaque orange |
| 15 | 30 | 0 | 0 | 30 | 30 | 30 |
| 16 | 30 | 30 | 100 | 30 | 30 | 30 |
| 17 | 5 | 5 | 5 | 5 | 5 | 5 |
| 18 | orange solid crude produts | orange solid crude produts | — | orange solid crude produts | orange solid crude produts | orange solid crude products |
| 19 | $MeOH/CH_2Cl_2$ = 1/60 | $MeOH/CH_2Cl_2$ = 1/60 | $MeOH/CH_2Cl_2$ = 1/80 | $MeOH/CH_2Cl_2$ = 1/90 | $MeOH/CH_2Cl_2$ = 1/100 | $MeOH/CH_2Cl_2$ = 1/100 |
| 20 | canary yellow solid products (439 mg, 1.34 mmol, 79%) | white solid products (541 mg, 1.65 mmol, 97%) | beige yellow solid products (1558 mg, 4.74 mmol, 84%) | white solid products (448 mg, 1.41 mmol, 81%) | yellow solid products (442 mg, 1.26 mmol, 74%) | white solid products (626 mg, 1.73 mmol, 102%) |

| | 70 | 74 | 75 | 76 | 77 | 78 |
|---|---|---|---|---|---|---|
| 1 | $C_{10}H_{11}NO_2$ (20, 301 mg, 1.70 mmol) | $C_{10}H_{11}NO_2$ (20, 301 mg, 1.69 mmol) | $C_{10}H_{11}NO_2$ (20, 1002 mg, 5.64 mmol) | $C_{10}H_{11}NO_2$ (20, 1000 mg, 5.64 mmol) | $C_{10}H_{11}NO_2$ (20, 300 mg, 1.69 mmol) | $C_{10}H_{11}NO_2$ (20, 300 mg, 1.69 mmol) |
| 2 | 10 | 10 | 35 | 35 | 10 | 10 |
| 3 | $C_{10}H_{13}O_2Br$ (1.0 g, 4.65 mmol) | $C_{10}H_{13}O_2Br$ (1.0 g, 4.08 mmol) | 2-chlorophenethyl bromide (3716 mg, 16.93 mmol) | 2-fluorophenethyl bromide (3438 mg, 16.93 mmol) | $C_9H_{10}BrNO_2$ (1215 mg, 4.98 mmol) | $C_9H_{10}BrNO_2$ (989 mg, 4.05 mmol) |
| 4 | 70 | 80 | 80 | 80 | 88 | 75 |
| 5 | transparent light yellow | transparent orange yellow | transparent yellow | transparent orange | transparent white | transparent white |
| 6 | 120 | 120 | — | — | 210 | 60 |
| 7 | turbid yellow | turbid yellow | — | — | turbid yellow | turbid yellow |
| 8 | 19 | 18 | 17 | 18 | 19.5 | 19.5 |
| 9 | 15 | 15 | 35 | 35 | 15 | 15 |
| 10 | — | — | 10 | 10 | 10 | 10 |
| 11 | transparent yellow | transparent orange yellow | turbid yellow | transparent light brown | turbid yellow | turbid yellow |
| 12 | 272 mg, 7.17 mmol | 270 mg, 7.13 mmol | 825 mg, 21.8 mmol | 836 mg, 22.1 mmol | 266 mg, 7.03 mmol | 271 mg, 7.16 mmol |
| 13 | 20 | 20 | 20 | 20 | 20 | 20 |
| 14 | transparent orange | transparent orange | opaque pinky orange | opaque pinky orange | transparent brown | transparent light orange |
| 15 | 30 | 30 | 100 | 100 | 30 | 30 |
| 16 | 30 | 30 | 100 | 100 | 30 | 30 |
| 17 | 5 | 5 | 5 | 5 | 5 | 5 |
| 18 | orange solid products | orange yellow solid products | light orange solid products | light orange solid products | orange oil products | orange oil products |
| 19 | $MeOH/CH_2Cl_2$ = 1/100 | $MeOH/CH_2Cl_2$ = 1/60 | $MeOH/CH_2Cl_2$ = 1/90 | $MeOH/CH_2Cl_2$ = 1/90 | $MeOH/CH_2Cl_2$ = 1/90 | $MeOH/CH_2Cl_2$ = 1/90 |
| 20 | white solid products | beige white solid products | white solid products (1601 mg, | white solid products | yellow oil products (503 mg, | yellow oil products |

TABLE 3-continued

The parameter table for the synthesis of compounds 63-67, 67-70 and 74-78

| (504 mg, 1.61 mmol, 95%) | 452 mg, 1.32 mmol, 78%) | 5.04 mmol, 89%) | (1501 mg, 4.98 mmol, 88%) | 1.47 mmol, 87%) | (492 mg, 1.44 mmol, 85%) |

Compound 68: A mixture of $C_{10}H_{11}NO_2$ (300 mg, 1.69 mmol), $C_8H_8Br_2$ (1.00 g, 3.79 mmol), and 2-propanol (10 mL) was heated to reflux for 23 h. The resulting solution was cooled to room temperature, and evaporated. The crude was dissolved in MeOH (15 mL), cooled to 0° C. in ice-bath, and then $NaBH_4$ (420 mg, 11.1 mmol) was added in portions under $N_2$. The mixture was stirred for another 20 min and then concentrated. The residue was treated with $CHCl_3$ (30 mL) and $H_2O$ (30 mL) and then the organic layer was dried over $MgSO_4$, filtered and evaporated. The purification is performed by the precipitation method. The crude product is dissolved with 5 mL of EtOAc, and then the product is precipitates with 10 mL of n-hexane to afford a beige solid (620 mg, 1.71 mmol).

Compound 121: To a solution of $C_{19}H_{23}NO_2$ (250 mg, 0.84 mmol) in HOAc (4.2 mL), $Pb(OAc)_4$ (579 mg, 1.31 mmol) was added and the mixture was stirred at room temperature under $N_2$ for 15 min. The reaction mixture was diluted with $CH_2Cl_2$ and $Na_2CO_{3(sat)}$ (20 mL) was added slowly. The solids formed in neutralization were removed by filtration and washed with $CH_2Cl_2$. The combined filtrate was extracted with $CH_2Cl_2$ (35 mL), and then the organic layer was washed with brine, dried over $MgSO_4$, filtered, and evaporated to afford a brown oil (480 mg, 1.35 mmol), which was used in the following reaction without further purification. To a solution of the crude oil in $CH_2Cl_2$ (17 mL), 1,3-dimethoxybenzene (0.17 mL, 1.3 mmol) and trifluoroacetic acid (0.84 mL) were added. The resulting mixture was stirred at room temperature for 30 min, and then $Na_2CO_{3(sat)}$ (20 mL) was added slowly. The resulting solution was extracted with $CH_2Cl_2$ (18 mL) and then the organic layer was washed brine, dried over $MgSO_4$, filtered, and evaporated. The crude residue was chromatographed (silica gel, $MeOH/CH_2Cl_2$=1/10) to afford a red-brown oil (214 mg, 0.49 mmol, 59%).

Compounds 105-110, 114-116, 120, 122, 123 and 125: Table 4 is a parameter table. The starting material "parameter 1" is added into the flask at room temperature under $N_2$ and dissolved with "parameter 2" mL HOAc. The solution which is "parameter 3" is added with $Pb(OAc)_4$ "parameter 4", and then the resulting solution which is "parameter 5" is stirred for "parameter 6" minutes, poured into the 125 mL conical flask, stirred and added slowly with "parameter 7" mL $Na_2CO_{3(sat)}$. The pH of the aqueous layer is alkaline (pH=8-9). The solid produced by neutralization is filtered and washed with $CH_2Cl_2$. The filtrate is extracted with "parameter 8" mL $CH_2Cl_2$. The organic layer is washed with brine, added with $MgSO_4$ for drying, stirred for 5 minutes, filtered, and concentrated to afford "parameter 9". The crude product is used in the following reaction without further purification.

The crude product is dissolved with "parameter 10" mL $CH_2Cl_2$ at room temperature under $N_2$. The solution which is "parameter 11" is added with 1,3-dimethoxybenzene "parameter 12" and trifluoroacetic acid "parameter 13". The color of the solution turns into "parameter 14". After the solution is stirred for "parameter 15" minutes, "parameter 16" mL $Na_2CO_{3(sat)}$ is added slowly. The pH of the aqueous layer is alkaline (pH=8-9), and "parameter 17" mL $CH_2Cl_2$ is added for extraction. The organic layer is washed with brine, added with $MgSO_4$ for drying, stirred for 5 minutes, filtered, and concentrated to obtain "parameter 18" mg crude product. The "parameter 20" is afforded after flash column chromatography (silica gel, "parameter 19").

TABLE 4

The parameter table for the synthesis of compounds 105-110, 114-116, 120, 122, 123 and 125

| | 105 | 106 | 107 | 108 | 109 |
|---|---|---|---|---|---|
| 1 | $C_{18}H_{20}N_2O_4$ (250 mg, 0.76 mmol) | $C_{18}H_{20}ClNO_2$ (160 mg, 0.50 mmol) | $C_{18}H_{19}Cl_2NO_2$ (250 mg, 0.71 mmol) | $C_{18}H_{20}BrNO_2$ (250 mg, 0.69 mmol) | $C_{18}H_{20}BrNO_2$ (250 mg, 0.69 mmol) |
| 2 | 3.8 | 2.5 | 3.6 | 3.5 | 3.6 |
| 3 | transparent light yellow | transparent light yellow | transparent light green | transparent light yellow | transparent light green |
| 4 | 509 mg, 1.15 mmol | 337 mg, 0.76 mmol | 473 mg, 1.07 mmol | 459 mg, 1.04 mmol | 470 mg, 1.06 mmol |
| 5 | transparent red brown | deep coffee color | red black | transparent coffee color | transparent coffee color |
| 6 | 15 | 60 | 27 | 15 | 15 |
| 7 | 25 | 20 | 25 | 40 | 25 |
| 8 | | 40 | 40 | 50 | 35 |
| 9 | red coffee color oil products (240 mg, 0.62 mmol) | coffee color oil products (218 mg, 0.58 mmol) | red coffe color oil products (291 mg, 0.71 mmol) | deep coffee color oil products (214 mg, 0.51 mmol) | red coffee color oil products (262 mg, 0.62 mmol) |
| 10 | 15 | 12 | 14 | 10 | 13 |
| 11 | transparent deep red brown | transparent red coffee color | transparent red coffee color | transparent red coffee color | transparent red coffee color |
| 12 | 0.14 mL, 1.1 mmol | 0.11 mL, 0.87 mmol | 0.14 mL, 1.06 mmol | 0.10 mL, 0.77 mmol | 0.12 mL, 0.93 mmol |
| 13 | 0.73 mL | 0.58 mL | 0.71 mL | 0.51 mL | 0.62 mL |

TABLE 4-continued

The parameter table for the synthesis of compounds
105-110, 114-116, 120, 122, 123 and 125

| | | | | | |
|---|---|---|---|---|---|
| 14 | transparent deep black tea color to transparent tea color | transparent red coffee brown to transparent light coffee color | transparent red coffee brown to transparent light coffee color | transparent red coffee brown to transparent light coffee color | transparent red coffee brown to transparent light coffee color |
| 15 | 30 | 60 | 30 | 30 | 70 |
| 16 | 25 | 10 | 20 | 30 | 15 |
| 17 | 20 | 23 | 26 | 30 | 27 |
| 18 | 480 | 327 | 490 | 325 | 342 |
| 19 | EA/n-hexane = 1/1 | MeOH/$CH_2Cl_2$/$NH_4OH$ = 1/100/0.1 | MeOH/$CH_2Cl_2$/$NH_4OH$ = 1/100/0.1 | MeOH/$CH_2Cl_2$/$NH_4OH$ = 1/100/0.1 | EtOAc/n-hexane = 1/2 |
| 20 | light orange yellow solid products (151 mg, 0.33 mmol, 43%) | coffee color oil products (130 mg, 0.29 mmol, 57%) | coffee color oil products (152 mg, 0.31 mmol, 44%) | red coffee color oil products (39 mg, 0.11 mmol, 11%) | light brown oil products (80 mg, 0.18 mmol, 26%) |

| | 110 | 114 | 115 | 116 | 120 |
|---|---|---|---|---|---|
| 1 | $C_{19}H_{23}NO_3$ (250 mg, 0.80 mmol) | $C_{19}H_{23}NO_2$ (250 mg, 0.73 mmol) | $C_{18}H_{20}ClNO_2$ (250 mg, 0.79 mmol) | $C_{18}H_{20}FNO_2$ (251 mg, 0.83 mmol) | $C_{19}H_{23}NO_3$ (250 mg, 0.798 mmol) |
| 2 | 4 | 3.7 | 4 | 4.2 | 4 |
| 3 | transparent light yellow | transparent light yellow | transparent light orange yellow | light orange yellow | light yellow |
| 4 | 569 mg, 1.28 mmol | 505 mg, 1.14 mmol | 570 mg, 1.29 mmol | 605 mg, 1.36 mmol | 532 mg, 1.20 mmol |
| 5 | transparent red coffee color | transparent red coffee color | translucent red coffee color | translucent red coffee color | deep coffee color |
| 6 | 15 | 15 | 15 | 15 | 15 |
| 7 | 25 | 30 | 25 | 25 | 25 |
| 8 | 40 | 35 | 35 | 35 | 35 |
| 9 | red coffee color oil products (243 mg, 0.65 mmol) | red coffee color oil products (253 mg, 0.63 mmol) | red coffee color oil products (300 mg, 0.80 mmol) | red coffee color oil products (285 mg, 0.79 mmol) | red coffee color oil products (290 mg, 0.781 mmol) |
| 10 | 13 | 13 | 16 | 16 | 16 |
| 11 | transparent red coffee color | coffee color | transparent red coffee color | transparent red coffee color | transparent red coffee color |
| 12 | 0.13 mL, 0.98 mmol | 0.13 mL, 0.95 mmol | 0.16 mL, 1.2 mmol | 0.16 mL, 1.2 mmol | 0.15 mL, 1.2 mmol |
| 13 | 0.65 mL | 0.63 mL | 0.79 mL | 0.79 mL | 0.78 mL |
| 14 | transparent red coffee color to transparent light coffee color | coffee color to light coffee color | transparent red coffee color to transparent light coffee color | transparent red coffee color to transparent light coffee color | transparent red coffee color to transparent coffee color |
| 15 | 30 | 30 | 30 | 30 | 30 |
| 16 | 20 | 20 | 25 | 20 | 25 |
| 17 | 22 | 22 | 19 | 19 | 19 |
| 18 | 450 | 433 | 480 | 417 | 560 |
| 19 | EA/n-hexane = 1/1 | MeOH/$CH_2Cl_2$ = 1/100 | EA/n-hexane = 1/2 | MeOH/$CH_2Cl_2$/$NH_4OH$ = 1/100/0.1 | MeOH/$CH_2Cl_2$/$NH_4OH$ = 1/100/0.1 |
| 20 | light brown oil products (217 mg, 0.48 mmol, 60%) | red coffee color oil products (129 mg, 0.26 mmol, 36%) | orange solid products (128 mg, 0.28 mmol, 36%) | light orange yellow solid products (126 mg, 0.29 mmol, 35%) | coffee color oil products (162 mg, 0.36 mmol, 45%) |

| | 122 | 123 | 125 |
|---|---|---|---|
| 1 | $C_{18}H_{20}ClNO_2$ (250 mg, 0.79 mmol) | $C_{19}H_{23}NO_3$ (250 mg, 0.80 mmol) | $C_{19}H_{23}NO_2$ (251 mg, 0.84 mmol) |
| 2 | 4.2 | 4 | 4.3 |
| 3 | transparent orange yellow | transparent orange yellow | transparent light orange yellow |
| 4 | 540 mg, 1.22 mmol | 578 mg, 1.30 mmol | 580 mg, 1.31 mmol |

TABLE 4-continued

The parameter table for the synthesis of compounds
105-110, 114-116, 120, 122, 123 and 125

|  |  |  |  |
|---|---|---|---|
| 5 | deep coffee color | deep coffee color | transparent red coffee color |
| 6 | 17 | 15 | 15 |
| 7 | 25 | 25 | 35 |
| 8 | 35 | 35 | 35 |
| 9 | red coffee color oil products (286 mg, 0.76 mmol) | deep red coffee color oil products (290 mg, 0.78 mmol) | red coffee color oil products (283 mg, 0.80 mmol) |
| 10 | 13 | 16 | 16 |
| 11 | transparent red coffee color | transparent deep red coffee color | transparent red coffee color |
| 12 | 0.15 mL, 1.1 mmol | 0.15 mL, 1.2 mmol | 0.16 mL, 1.2 mmol |
| 13 | 0.76 mL | 0.78 m | 0.8 mL |
| 14 | transparent red coffee color to transparent coffee color | transparent deep red coffee color to deep coffee color | transparent deep red coffee color to transparent light coffee color |
| 15 | 33 | 30 | 30 |
| 16 | 25 | 25 | 25 |
| 17 | 22 | 19 | 19 |
| 18 | 430 | 430 | 506 |
| 19 | EA/n-hexane = 1/1 | EA/n-hexane = 1/1 | MeOH/CH$_2$Cl$_2$ = 1/200 |
| 20 | orange yellow solid products (151 mg, 0.33 mmol, 42%) | light brown oil products (140 mg, 0.31 mmol, 39%) | light orange yellow solid products (135 mg, 0.31 mmol, 37%) |

Compounds 141 and 142: Table 5 is a parameter table. "Parameter 1" and 2-methoxyphenylboronic acid (46 mg, 0.30 mmol) are added into the reaction vessel for microwave-assisted heating and dissolved with 2-propanol (2 mL), and stirred for 30 minutes. Pd(OAc)$_2$ "parameter 2", PPh$_3$ "parameter 3", 2 M Na$_2$CO$_{3(aq)}$ (0.14 mL, 0.28 mmol), and H$_2$O (0.2 mL) are added and the mixture is heated at 120° C. for 20 minutes using microwave synthesizer. Before the temperature of the solution is decreased, the solution us added H$_2$O (0.7 mL), stirred in the air until reaching room temperature, diluted with 10 mL of EtOAc, and extracted with 10 mL of H$_2$O. The organic layer is washed with 5% NaHCO$_{3(aq)}$, washed with brine, added in "parameter 4" mg Darco G-60, stirred for 10 minutes, added in MgSO$_4$ for drying, stirred for 10 minutes, filtered by the sintered glass funnel covered with about 1 cm of Celite and a thin layer of Florisil, concentrated. The crude product is purified by flash column chromatography (silica gel, "parameter 5") to obtain a yellow oil "parameter 6". Free base "parameter 7" is dissolved in CH$_2$Cl$_2$, and then a solution of HCl in CH$_2$Cl$_2$ is added until pH=1. The resulting mixture is concentrated to obtain hydrochloride salt "parameter 8".

TABLE 5

The parameter table for the synthesis of compounds 141 and 142

|  | 141 | 142 |
|---|---|---|
| 1 | 103 mg, 0.24 mmol | 104 mg, 0.25 mmol |
| 2 | 1.4 mg, 0.006 mmol | 2.0 mg, 0.009 mmol |
| 3 | 6.5 mg, 0.024 mmol | 5.9 mg, 0.022 mmol |
| 4 | 112 | 117 |
| 5 | 1/4 | 2/1 |
| 6 | 88 mg, 0.20 mmol, 83% | 76 mg, 0.17 mmol, 72% |
| 7 | 83 mg, 0.20 mmol | 18 mg, 0.04 mmol |
| 8 | beige white solid products (100 mg, 0.20 mmol) | light yellow oil products (20 mg, 0.04 mmol) |

Compound 150: To a solution of C$_{18}$H$_{20}$BrNO$_2$ (100 mg, 0.28 mmol) in DMF (2 mL), trimethylphenyl-ammonium chloride ((CH$_3$)$_3$PhNCl, 102 mg, 0.59 mmol) and t-BuOK (67 mg, 0.60 mmol) were added. The suspension was heated to 60° C. under N$_2$ for 3.5 h, and then (CH$_3$)$_3$PhNCl (102 mg, 0.59 mmol) was added and heated to 70° C. for 4.5 h. After cooling to room temperature, the reaction mixture was treated with CHCl$_3$ (10 mL) and 5% NaOH$_{(aq)}$ (20 mL). The organic layer was washed with brine, dried over MgSO$_4$, filtered, and evaporated. The crude residue was chromatographed (silica gel, EtOAc/n-hexane=1/4) to afford a yellow solid (83 mg, 0.22 mmol, 79%).

Compound 152: To a solution of C$_{18}$H$_{19}$BrN$_2$O$_4$ (406 mg, 1.00 mmol) in DMF (9 mL), which was cooled to 0° C. and degassed, NaH (40 mg, 1.67 mmol) and CH$_3$I (0.06 mL, 0.98 mmol) in DMF (1 mL) were added. After stirring for 10 min, NH$_4$Cl (111 mg, 2.08 mmol) was added, and then the reaction mixture was treated with diethyl ether (100 mL) and H$_2$O (100 mL). The organic layer was washed with brine, dried over MgSO$_4$, filtered and evaporated. The crude residue was chromatographed (silica gel, EtOAc/n-hexane=1/2) to afford a yellow solid (123 mg, 0.29 mmol, 30%).

Compound 153: To a solution of $C_{18}H_{19}BrClNO_2$ (300 mg, 0.75 mmol) in DMF (6 mL), $(CH_3)_3PhNCl$ (542 mg, 3.16 mmol) and t-BuOK (333 mg, 2.97 mmol) were added. The suspension was heated to 60° C. under $N_2$ for 16 h, and then heated to 70° C. for 1 h. After cooling to room temperature, the reaction mixture was treated with $Et_2O$ (100 mL) and $H_2O$ (100 mL). The organic layer was washed with brine, dried over $MgSO_4$, filtered, and evaporated. The crude residue was chromatographed (silica gel, EtOAc/n-hexane=1/4) to afford a white solid (189 mg, 0.46 mmol, 61%).

Compound 154: To a solution of $C_{18}H_{19}BrFNO_2$ (400 mg, 1.05 mmol) in DMF (8 mL), $(CH_3)_3PhNCl$ (727 mg, 4.23 mmol) and t-BuOK (468 mg, 4.17 mmol) were added. The suspension was heated to 70° C. under $N_2$ for 16 h. After cooling to room temperature, the reaction mixture was treated with $Et_2O$ (100 mL) and $H_2O$ (100 mL). The organic layer was washed with brine, dried over $MgSO_4$, filtered, and evaporated. The crude residue was chromatographed (silica gel, EtOAc/n-hexane=1/4) to afford a white solid (247 mg, 0.63 mmol, 60%).

Compounds 157-159, 165-168 and 171-173: Table 6 is a parameter table. "Parameter 1" is added into the reaction vessel for microwave-assisted heating and dissolved with "parameter 2" mL 2-propanol. "Parameter 3" is added thereinto, and stirred for 30 minutes. $Pd(OAc)_2$ "parameter 4", $PPh_3$ "parameter 5", 2 M $Na_2CO_{3(aq)}$ "parameter 6" and "parameter 7" mL $H_2O$ are added and heated to 120° C. for 20 min using microwave synthesizer. Before the temperature of the solution is decreased, "parameter 8" mL $H_2O$ is added, and then cooled to room temperature, diluted with 10 mL EtOAc, and extracted with 10 mL $H_2O$. The organic layer is washed with 5% $NaHCO_{3(aq)}$ followed by brine, added in "parameter 9" mg Darco G-60, stirred for 10 min, filtered by the sintered glass funnel covered with about 1 cm of Celite and a thin layer of Florisil, concentrated, and purified by flash column chromatography (silica gel, "parameter 10") to obtain "parameter 11".

TABLE 6

The parameter table for the synthesis of compounds 157-159, 165-168 and 171-173

|    | 157 | 158 | 159 | 165 | 166 |
|----|-----|-----|-----|-----|-----|
| 1 | 2-fluorophenylboronic acid (58 mg, 0.41 mmol) | 2-chlorophenylboronic acid (55 mg, 0.35 mmol) | 2-methoxyphenylboronic acid (55 mg, 0.36 mmol) | 2-fluorophenylboronic acid (55 mg, 0.39 mmol) | 2-chlorophenylboronic acid (60 mg, 0.38 mmol) |
| 2 | 2 | 1.8 | 1.8 | 2 | 2 |
| 3 | $C_{19}H_{24}BrNO_2$ (102 mg, 0.27 mmol) | $C_{19}H_{24}BrNO_2$ (90 mg, 0.24 mmol) | $C_{19}H_{24}BrNO_2$ (89 mg, 0.24 mmol) | $C_{19}H_{21}BrFNO2$ (105 mg, 0.27 mmol) | $C_{19}H_{21}BrFNO_2$ (101 mg, 0.26 mmol) |
| 4 | 1.5 mg, 0.007 mmol | 1.6 mg, 0.007 mmol | 1.7 mg, 0.0076 mmol | 1.6 mg, 0.007 mmol | 1.4 mg, 0.006 mmol |
| 5 | 4.2 mg, 0.016 mmol | 8.0 mg, 0.03 mmol | 4.7 mg, 0.018 mmol | 6.0 mg, 0.023 mmol | 5.6 mg, 0.021 mmol |
| 6 | 0.20 mL, 0.40 mmol | 0.18 mL, 0.36 mmol | 0.18 mL, 0.36 mmol | 0.19 mL, 0.38 mmol | 0.19 mL, 0.38 mmol |
| 7 | 0.2 | 0.18 | 0.18 | 0.2 | 0.2 |
| 8 | 0.7 | 0.63 | 0.63 | 0.7 | 0.7 |
| 9 | 117 | 113 | 99 | 101 | 117 |
| 10 | 1/3 | 1/3 | 1/2 | 1/4 | 1/4 |
| 11 | beige yellow oil products (103 mg, 0.26 mmol, 97%) | light yellow oil products (58 mg, 0.14 mmol, 59%) | light yellow oil products (69 mg, 0.17 mmol, 71%) | yellow oil products (108 mg, 0.26 mmol, 99%) | light yellow oil products (50 mg, 0.12 mmol, 47%) |
| 12 | $C_{25}H_{26}FNO_2$ (103 mg, 0.26 mmol) | $C_{25}H_{26}ClNO_2$ (31 mg, 0.08 mmol) | $C_{26}H_{29}NO_3$ (69 mg, 0.17 mmol) | $C_{25}H_{25}F_2NO_2$ (108 mg, 0.26 mmol) | $C_{25}H_{25}ClFNO_2$ (50 mg, 0.12 mmol) |
| 13 | white solid products (113 mg, 0.26 mmol) | light yellow solid products (36 mg, 0.08 mmol) | light yellow solid products (66 mg, 0.15 mmol) | light yellow solid products (116 mg, 0.26 mmol) | beige white solid muriate products (55 mg, 0.12 mmol) |

|    | 167 | 168 | 171 | 172 | 173 |
|----|-----|-----|-----|-----|-----|
| 1 | 2-fluorophenylboronic acid (45 mg, 0.32 mmol) | 2-chlorophenylboronic acid (48 mg, 0.31 mmol) | 2-fluorophenylboronic acid (50 mg, 0.36 mmol) | 2-chlorophenylboronic acid (56 mg, 0.36 mmol) | 2-methoxyphenylboronic acid (56 mg, 0.37 mmol) |
| 2 | 1.8 | 1.7 | 2 | 2 | 2 |
| 3 | $C_{19}H_{21}BrClNO_2$ (90 mg, 0.22 mmol) | $C_{19}H_{21}BrClNO_2$ (84 mg, 0.20 mmol) | $C_{19}H_{22}BrN_2O_4$ (98 mg, 0.23 mmol) | $C_{19}H_{22}BrN_2O_4$ (100 mg, 0.24 mmol) | $C_{19}H_{22}BrN_2O_4$ (101 mg, 0.24 mmol) |
| 4 | 2.0 mg, 0.009 mmol | 1.0 mg, 0.004 mmol | 1.7 mg, 0.0076 mmol | 1.8 mg, 0.0072 mmol | 1.8 mg, 0.008 mmol |
| 5 | 4.7 mg, 0.02 mmol | 4.4 mg, 0.02 mmol | 5.7 mg, 0.022 mmol | 6.0 mg, 0.023 mmol | 6.5 mg, 0.025 mmol |
| 6 | 0.19 mL, 0.38 mmol | 0.16 mL, 0.32 mmol | 0.18 mL, 0.36 mmol | 0.18 mL, 0.36 mmol | 0.18 mL, 0.36 mmol |
| 7 | 0.2 | 0.17 | 0.2 | 0.2 | 0.2 |
| 8 | 0.7 | 0.6 | 0.7 | 0.7 | 0.7 |
| 9 | 105 | 90 | 112 | 101 | 115 |
| 10 | 1/3 | 1/3 | 1/1 | 1/2 | 1/1 |
| 11 | yellow oil products (91 mg, 0.21 mmol, 97%) | beige yellow solid products (66 mg, 0.15 mmol, 73%) | beige solid products (75 mg, mg, 0.17 mmol, 71%) | beige white solid products (72 mg, 0.16 mmol, 66%) | beige yellow solid products (88 mg, 0.20 mmol, 81%) |
| 12 | $C_{25}H_{25}ClFNO_2$ (91 mg, 0.21 mmol) | $C_{25}H_{25}Cl_2NO_2$ (66 mg, 0.15 mmol) | $C_{25}H_{25}FN_2O_4$ (56 mg, 0.13 mmol) | $C_{25}H_{25}ClN_2O_4$ (72 mg, 0.16 mmol) | $C_{26}H_{28}N_2O_5$ (72 mg, 0.16 mmol) |
| 13 | light yellow solid products (94 mg, 0.20 mmol) | beige solid products (72 mg, 0.15 mmol) | beige white solid products (61 mg, 0.13 mmol) | beige yellow solid products (81 mg, 0.17 mmol) | beige white solid products (80 mg, 0.16 mmol) |

TABLE 7

The analytical data of the compounds in this invention

| | |
|---|---|
| Compound number | 7 |
| Name | 6-Methoxy-2-propyl-1,2,3,4-tetrahydroisoquinolin-7-ol |
| $^1$H NMR (200 MHz, CDCl$_3$) | δ 0.84 (t, J = 7.3 Hz, 3H), 1.47-1.59 (m, 2H), 2.33-2.41 (m, 2H), 2.64 (d, J = 4.8 Hz, 2H), 2.71 (d, J = 4.8 Hz, 2H), 3.70 (s, 3H), 3.89 (s, 2H), 6.04 (s, 1H), 6.41 (s, 1H), 6.43 (s, 1H) |
| $^{13}$C NMR (50 MHz, CDCl$_3$) | δ 12.5, 20.4, 28.7, 51.5, 55.7, 56.2, 60.8, 111.2, 113.2, 125.4, 127.1, 144.5, 146.2 |
| ESI-MS | m/z 222 ([M + H]$^+$) |
| EIHR-MS | calcd for C$_{13}$H$_{19}$NO$_2$ [M]+, 221.1416; found, 221.1442 |
| Compound number | 8 |
| Name | 8-(2,4-Dimethoxyphenyl)-6-methoxy-2-propyl-1,2,3,4-tetrahydroisoquinolin-7-ol |
| $^1$H NMR (200 MHz, CDCl$_3$) | δ 0.85 (t, J = 7.3 Hz, 3H), 1.38-1.53 (m, 2H), 2.26-2.37 (m, 3H), 2.63-2.72 (m, 2H), 2.85-2.91 (m, 2H), 3.17 (s, 2H), 3.72 (s, 3H), 3.85 (s, 3H), 3.86 (s, 3H), 6.55-6.61 (m, 2H), 7.00-7.05 (m, 1H) |
| $^{13}$C NMR (50 MHz, CDCl$_3$) | δ 12.4, 20.6, 29.6, 50.9, 54.6, 55.8, 56.0, 56.3, 60.7, 99.4, 105.1, 110.5, 116.8, 122.9, 125.5, 127.1, 132.2, 141.7, 145.5, 158.5, 161.0 |
| EIHR-MS | calcd for C$_{21}$H$_{27}$NO$_4$ [M]$^+$, 357.1940; found, 357.1915. |
| Compound number | 10 |
| Name | 7-(Benzyloxy)-6-methoxy-1-methyl-3,4-dihydroisoquinoline |
| $^1$H NMR (200 MHz, CDCl$_3$) | δ 2.25 (s, 3H), 2.62 (t, J = 7.6 Hz, 2H), 3.57-3.61 (m, 2H), 3.91 (s, 3H), 5.15 (s, 2H), 6.69 (s, 1H), 7.01 (s, 1H), 7.34-7.48 (m, 5H) |
| $^{13}$C NMR (50 MHz, CDCl$_3$) | δ 23.8, 26.3, 47.4, 56.5, 72.2, 111.1, 113.0, 122.8, 128.0, 128.5, 129.1, 132.3, 137.5, 146.9, 152.2, 164.3. |
| Compound number | 11 |
| Name | 7-(Benzyloxy)-6-methoxy-1,2-dimethyl-1,2,3,4-tetrahydroisoquinoline |
| $^1$H NMR (200 MHz, CDCl$_3$) | δ 1.32 (d, J = 6.7 Hz, 3H), 2.48 (s, 3H), 2.65-2.74 (m, 1H), 2.78-2.84 (m, 2H), 3.00-3.11 (m, 1H), 3.56 (q, J = 6.5 Hz, 1H), 3.84 (s, 3H), 5.10 (s, 2H), 6.59 (s, 1H), 6.60 (s, 1H), 7.23-7.45 (m, 5H) |
| $^{13}$C NMR (50 MHz, CDCl$_3$) | δ 20.0, 27.5, 43.0, 49.1, 56.4, 59.1, 71.8, 112.1, 113.5, 126.6, 127.8, 128.2, 128.9, 131.1, 137.7, 146.8, 148.7. |
| Compound number | 12 |
| Name | 7-(Benzyloxy)-6-methoxy-1-methyl-2-propyl-1,2,3,4-tetrahydroisoquinoline |
| $^1$H NMR (200 MHz, CDCl$_3$) | δ 0.97 (t, J = 7.4 Hz, 3H), 1.68 (d, J = 6.8 Hz, 3H), 1.96-2.02 (m, 2H), 2.92-2.99 (m, 2H), 3.01-3.03 (m, 1H), 3.08-3.13 (m, 1H), 3.35-3.41 (m, 1H), 3.46-3.53 (m, 1H), 3.86 (s, 3H), 4.41 (d, J = 6.8 Hz, 1H), 5.08-5.15 (m, 2H), 6.62 (s, 1H), 6.66 (s, 1H), 7.29-7.45 (m, 5H) |
| $^{13}$C NMR (100 MHz, CDCl$_3$) | δ 11.2, 18.2, 20.1, 22.9, 43.5, 53.7, 55.9, 57.3, 71.2, 111.5, 112.5, 122.4, 124.7, 127.3, 127.8, 128.4, 136.4, 147.3, 149.5 |
| EIHR-MS | calcd for C$_{21}$H$_{27}$NO$_2$ [M]+, 325.2042; found, 325.2022. |
| Compound number | 13 |
| Name | 6-Methoxy-1,2-dimethyl-1,2,3,4-tetrahydroisoquinolin-7-ol |
| $^1$H NMR (200 MHz, CD$_3$OD) | δ 1.59 (d, J = 6.7 Hz, 3H), 2.87 (s, 3H), 3.00-3.07 (m, 2H), 3.34-3.38 (m, 1H), 3.49-3.63 (m, 1H), 3.84 (s, 3H), 4.34 (q, J = 6.7 Hz, 1H), 6.63 (s, 1H), 6.75 (s, 1H) |
| $^{13}$C NMR (50 MHz, CD$_3$OD) | δ 19.0, 24.5, 39.9, 47.8, 56.4, 60.1, 112.4, 114.2, 122.1, 126.5, 147.0, 149.1. |
| Compound number | 14 |
| Name | 6-Methoxy-1-methyl-2-propyl-1,2,3,4-tetrahydroisoquinolin-7-ol |
| $^1$H NMR (400 MHz, CDCl$_3$) | δ 0.88 (t, J = 7.3 Hz, 3H), 1.66 (d, J = 6.7 Hz, 3H), 1.86-1.98 (m, 2H), 2.94-3.03 (m, 2H), 3.04-3.09 (m, 2H), 3.39-3.41 (m, 1H), 3.45-3.50 (m, 1H), 3.76 (s, 3H), 4.41 (q, J = 6.6 Hz, 1H), 6.56 (s, 1H), 6.60 (s, 1H) |
| $^{13}$C NMR (100 MHz, CDCl$_3$) | δ 11.1, 17.7, 20.0, 22.5, 43.6, 53.4, 56.0, 57.5, 110.7, 112.4, 120.4, 124.2, 145.1, 146.8 |
| EIHR-MS | calcd for C$_{14}$H$_{21}$NO$_2$ [M]$^+$, 235.1572; found, 235.1601. |
| Compound number | 15 |
| Name | 8-(2,4-Dimethoxyphenyl)-6-methoxy-1,2-dimethyl-1,2,3,4-tetrahydroisoquinolin-7-ol |
| $^1$H NMR (400 MHz, CDCl$_3$) | δ 1.02 (d, J = 8.0 Hz, 3H), 2.56 (s, 3H), 2.77 (dd, J = 16.0, 4.0 Hz, 1H), 2.93-2.98 (m, 1H), 3.06-3.16 (m, 1H), 3.22-3.31 (m, 1H), 3.77 (s, 3H), 3.86 (s, 3H), 3.88 (s, 3H), 6.58-6.61 (m, 2H), 6.63 (s, 1H), 6.98 (dd, J = 6.1, 2.8 Hz, 1H) |
| $^{13}$C NMR (100 MHz, CDCl$_3$) | δ 16.1, 25.3, 41.4, 44.1, 55.5, 55.7, 55.9, 99.3, 105.1, 110.4, 116.1, 122.7, 123.2, 128.7, 131.5, 142.3, 145.5, 158.5, 160.0 |
| EIHR-MS | calcd for C$_{20}$H$_{25}$NO$_4$ [M]$^+$, 343.1784; found, 343.1791. |
| Compound number | 16 |
| Name | 8-(2,4-Dimethoxyphenyl)-6-methoxy-1-methyl-2-propyl-1,2,3,4-tetrahydroisoquinolin-7-ol |
| $^1$H NMR (400 MHz, CDCl$_3$) | δ 0.87 (t, J = 8.0 Hz, 3H), 0.98 (d, J = 4.0 Hz, 3H), 1.49 (q, J = 8.0 Hz, 2H), 2.44-2.54 (m, 3H), 2.85-2.88 (m, 1H), 2.90-3.05 (m, 1H), 3.19-3.30 (m, 1H), 3.55 (q, J = 8.0 Hz, 1H), 3.72 (s, 3H), 3.86 (s, 3H), 3.87 (s, 3H), 5.30 (s, 1H), 6.57-6.62 (m, 3H), 7.10 (d, J = 8.0 Hz, 1H) |
| $^{13}$C NMR (100 MHz, CDCl$_3$) | δ 12.1, 19.3, 21.3, 24.7, 42.8, 53.1, 55.46, 55.49, 55.6, 55.9, 99.2, 104.7, 110.6, 116.4, 122.9, 124.3, 132.6, 133.3, 141.4, 145.1, 157.5, 160.8 |
| ESI-MS | m/z 371.0 [M]$^+$ |
| Compound number | 21 |
| Name | 6-Methoxy-2-phenethyl-1,2,3,4-tetrahydroisoquinolin-7-ol |
| $^1$H NMR (200 MHz, CDCl$_3$) | δ 2.71-2.96 (m, 8H), 3.61 (s, 2H), 3.84 (s, 3H), 6.57 (s, 2H), 7.16-7.34 (m, 5H) |
| $^{13}$C NMR (50 MHz, CDCl$_3$) | δ 28.8, 34.1, 51.2, 55.6, 56.0, 60.4, 110.8, 112.4, 125.5, 126.2, 127.3, 128.5, 128.9, 140.5, 143.8, 145.4 |
| Compound number | 29 |
| Name | 6-Methoxy-8-(2-methoxyphenyl)-2-phenethyl-1,2,3,4-tetrahydroisoquinolin-7-ol |
| $^1$H NMR (200 MHz, CDCl$_3$) | δ 2.57-2.66 (m, 2H), 2.72-2.81 (m, 4H), 2.85-2.92 (m, 2H), 3.25 (s, 2H), 3.74 (s, 3H), 3.86 (s, 3H), 6.63 (s, 1H), 6.97-7.06 (m, 2H), 7.11-7.28 (m, 6H), 7.32-7.40 (m, 1H) |
| $^{13}$C NMR (50 MHz, CDCl$_3$) | δ 29.2, 34.0, 50.5, 54.2, 55.7, 56.0, 60.0, 110.2, 111.3, 120.9, 122.8, 124.1, 125.2, 126.0, 126.2, 128.4, 128.7, 129.3, 131.6, 140.5, 141.1, 145.2, 157.1 |
| ESI-MS | m/z 390 ([M + H]$^+$) |
| EIHR-MS | calcd for C$_{25}$H$_{28}$NO$_3$ [M + H]$^+$, 390.2069; found, 390.2054. |
| Compound number | 30 |
| Name | 6-Methoxy-8-(4-methoxyphenyl)-2-phenethyl-1,2,3,4-tetrahydroisoquinolin-7-ol |
| $^1$H NMR (200 MHz, CDCl$_3$) | δ 2.59-2.68 (m, 2H), 2.73-2.82 (m, 4H), 2.92, (t, J = 5.8 Hz, 2H), 3.29 (s, 2H), 3.83 (s, 3H), 3.87 (s, 3H), 6.62 (s, 1H), 6.93-6.94, (m, 1H), 6.98-6.99 (m, 1H), 7.12-7.24 (m, 7H) |
| $^{13}$C NMR (50 MHz, CDCl$_3$) | δ 29.4, 34.0, 50.6, 55.0, 55.3, 56.1, 60.2, 110.0, 114.1, 125.4, 125.9, 126.0, 127.6, 128.4, 128.7, 130.9, 140.4, 141.2, 145.4, 158.9 |
| ESI-MS | m/z 390 ([M + H]$^+$), 412 ([M + Na]$^+$) |
| EIHR-MS | calcd for C$_{25}$H$_{28}$NO$_3$ [M + H]$^+$, 390.2069; found, 390.2067 |
| Compound number | 31 |
| Name | 6-Methoxy-8-(3-methoxyphenyl)-2-phenethyl-1,2,3,4-tetrahydroisoquinolin-7-ol |
| $^1$H NMR (200 MHz, CDCl$_3$) | δ 2.59-2.68 (m, 2H), 2.74-2.80 (m, 4H), 2.89-2.95 (m, 2H), 3.31 (s, 2H), 3.78 (s, 3H), 3.86 (s, 3H), 6.63 (s, 1H), 6.78-6.83, (m, 2H), 6.86-6.94 (m, 1H), 7.11-7.24 (m, 5H), 7.30-7.40 (m. 1H) |
| $^{13}$C NMR (50 MHz, CDCl$_3$) | δ 29.2, 33.8, 50.4, 54.7, 55.2, 56.0, 60.0, 110.1, 113.3, 115.2, 122.1, 125.3, 125.4, 126.1, 126.2, 128.4, 128.7, 129.6, 136.9, 140.3, 141.0, 145.4, 159.7 |
| ESI-MS | m/z 390.2 ([M + H]$^+$), 412.2 ([M + Na]$^+$) |
| EIHR-MS | calcd for C$_{25}$H$_{28}$NO$_3$ [M + H]$^+$, 390.2069; found, 390.2064 |
| Compound number | 32 |
| Name | 6-Methoxy-8-(3,4,5-trimethoxyphenyl)-2-phenethyl-1,2,3,4-tetrahydroisoquinolin-7-ol |

TABLE 7-continued

The analytical data of the compounds in this invention

| | |
|---|---|
| ¹H NMR (200 MHz, CDCl₃) | δ 2.62-2.71 (m, 2H), 2.78-2.85 (m, 4H), 2.91-2.96 (m, 2H), 3.32 (s, 2H), 3.90 (s, 6H), 3.91 (s, 3H), 3.92 (s, 3H), 5.41 (s, 1H), 6.46 (s, 2H), 6.65 (s, 1H), 7.13-7.30 (m, 5H) |
| ¹³C NMR (50 MHz, CDCl₃) | δ 29.5, 34.1, 50.5, 54.5, 56.2, 60.3, 61.0, 106.6, 110.3, 125.7, 126.2, 126.3, 128.5, 128.8, 131.0, 137.1, 140.3, 140.9, 145.4, 153.5 |
| ESI-MS | m/z 449 ([M]⁺) |
| EIHR-MS | calcd for $C_{27}H_{32}NO_5$ [M + H]⁺, 450.2280; found, 450.2268 |
| Compound number | 33 |
| Name | 6-Methoxy-2-phenethyl-8-phenyl-1,2,3,4-tetrahydroisoquinolin-7-ol |
| ¹H NMR (200 MHz, CDCl₃) | δ 2.57-2.66 (m, 2H), 2.72-2.79 (m, 4H), 2.89-2.94 (m, 2H), 3.28 (s, 2H), 3.85 (s, 3H), 6.63 (s, 1H), 7.10-7.14 (m, 2H), 7.19-7.25 (m, 5H), 7.32-7.48 (m, 3H) |
| ¹³C NMR (50 MHz, CDCl₃) | δ 29.3, 33.9, 50.5, 54.9, 56.1, 60.1, 110.6, 125.4, 126.1, 126.4, 127.5, 128.4, 128.6, 128.7, 129.8, 135.7, 140.3, 141.0, 145.4 |
| ESI-MS | m/z 360 ([M + H]⁺) |
| EIHR-MS | calcd for $C_{24}H_{26}NO_2$ [M + H]⁺, 360.1964; found, 360.1956 |
| Compound number | 34 |
| Name | 6-Methoxy-8-(2-methylthiophenyl)-2-phenethyl-1,2,3,4-tetrahydroisoquinolin-7-ol |
| ¹H NMR (200 MHz, CDCl₃) | δ 2.37 (s, 3H), 2.57-2.66 (m, 2H), 2.72-2.81 (m, 4H), 2.89-2.92 (m, 2H), 3.22 (s, 2H), 3.88 (s, 3H), 6.67 (s, 1H), 7.12-7.22 (m, 8H), 7.25-7.29 (m, 1H) |
| ¹³C NMR (50 MHz, CDCl₃) | δ 15.2, 29.2, 34.0, 50.5, 53.8, 56.0, 60.0, 110.6, 124.1, 124.7, 125.0, 125.6, 125.9, 126.1, 128.4, 128.6, 128.8, 130.1, 133.9, 138.6, 140.5, 141.0, 145.2 |
| ESI-MS | m/z 406 ([M + H]⁺) |
| EIHR-MS | calcd for $C_{25}H_{28}NO_2S$ [M + H]⁺, 406.1841; found, 406.1836 |
| Compound number | 35 |
| Name | 6-Methoxy-8-(4-methylthiophenyl)-2-phenethyl-1,2,3,4-tetrahydroisoquinolin-7-ol |
| ¹H NMR (200 MHz, CDCl₃) | δ 2.51 (s, 3H), 2.63-2.68 (m, 2H), 2.74-2.81 (m, 4H), 2.89-2.95 (m, 2H), 3.29 (s, 2H), 3.88 (s, 3H), 6.63 (s, 1H), 7.14-7.21 (m, 6H), 7.25-7.33 (m, 3H) |
| ¹³C NMR (50 MHz, CDCl₃) | δ 15.7, 29.4, 33.9, 50.5, 55.0, 56.1, 60.2, 110.1, 125.5, 125.6, 126.1, 126.5, 128.4, 128.8, 130.3, 137.6, 140.4, 141.1, 145.4 |
| ESI-MS | 406 ([M + H]⁺) |
| EIHR-MS | calcd for $C_{25}H_{28}NO_2S$ [M + H]⁺, 406.1841; found, 406.1839 |
| Compound number | 36 |
| Name | 8-(Benzo[1,3]dioxol-5-yl)-6-methoxy-2-phenethyl-1,2,3,4-tetrahydroisoquinolin-7-ol |
| ¹H NMR (200 MHz, CDCl₃) | δ 2.61-2.70 (m, 2H), 2.73-2.84 (m, 4H), 2.89-2.94 (m, 2H), 3.30 (s, 2H), 3.88 (s, 3H), 5.43 (bs, 1H), 6.00 (bs, 2H), 6.63 (s, 1H), 6.68-6.73 (m, 2H), 6.86-6.90 (m, 1H), 7.16-7.26 (m, 5H) |
| ¹³C NMR (50 MHz, CDCl₃) | δ 29.5, 34.1, 50.6, 55.0, 56.2, 60.3, 101.2, 108.7, 110.1, 110.4, 123.1, 125.5, 125.9, 126.1, 128.5, 128.8, 129.0, 140.4, 141.2, 145.3, 147.0, 147.8 |
| ESI-MS | m/z 404 ([M + H]⁺) |
| EIHR-MS | calcd for $C_{25}H_{26}NO_4$ [M + H]⁺, 404.1862; found, 404.1849 |
| Compound number | 37 |
| Name | 8-(2-Cyanophenyl)-6methoxy-2-phenethyl-1,2,3,4-tetrahydroisoquinolin-7-ol |
| ¹H NMR (200 MHz, CDCl₃) | δ 2.61-2.80 (m, 6H), 2.87-2.94 (m, 2H), 3.12 (d, J = 14.8 Hz, 1H), 3.32 (d, J = 14.9 Hz, 1H), 3.90 (s, 3H), 6.68 (s, 1H), 7.12-7.29 (m, 5H), 7.35 (ddd, J = 7.7, 1.3, 0.6 Hz, 1H), 7.46 (td, J = 7.6, 1.3 Hz, 1H), 7.65 (td, J = 7.6, 1.5 Hz, 1H), 7.77 (ddd, J = 7.7, 1.4, 0.5 Hz, 1H) |
| ¹³C NMR (50 MHz, CDCl₃) | δ 29.2, 34.0, 50.3, 54.3, 56.1, 60.0, 111.2, 114.0, 118.2, 122.2, 125.1, 126.0, 126.2, 128.1, 128.5, 128.8, 131.0, 132.8, 133.2, 140.3, 141.3, 145.3 |
| ESI-MS | m/z 385 ([M + H]⁺) |
| EIHR-MS | calcd for $C_{25}H_{25}N_2O_2$ [M + H]⁺, 385.1916; found, 385.1910 |
| Compound number | 38 |
| Name | 6-Methoxy-8-(2-nitrophenyl)-2-phenethyl-1,2,3,4-tetrahydroisoquinolin-7-ol |
| ¹H NMR (200 MHz, CDCl₃) | δ 2.63-2.82 (m, 6H), 2.87-2.91 (m. 2H), 3.14 (d, J = 15.0 Hz, 1H), 3.40 (d, J = 14.9 Hz, 1H), 3.87 (s, 3H), 6.65 (s, 1H), 7.12-7.26 (m, 5H), 7.30-7.36 (m, 1H), 7.48-7.58 (m, 1H), 7.60-7.70 (m, 1H), 8.01-8.08 (m, 1H) |
| ¹³C NMR (50 MHz, CDCl₃) | δ 28.9, 33.9, 50.3, 54.0, 56.1, 59.7, 110.6, 121.9, 124.6, 124.8, 125.8, 126.2, 128.5, 128.8, 131.0, 132.6, 133.1, 140.3, 140.7, 145.0, 149.6 |
| ESI-MS | m/z 405 ([M + H]⁺) |
| EIHR-MS | calcd for $C_{24}H_{25}N_2O_4$ [M + H]⁺, 405.1814; found, 405.1800 |
| Compound number | 39 |
| Name | 8-(2-Chlorophenyl)-6-methoxy-2-phenethyl-1,2,3,4-tetrahydroisoquinolin-7-ol |
| ¹H NMR (200 MHz, CDCl₃) | δ 2.59-2.69 (m, 2H), 2.72-2.82 (m, 4H), 2.88-2.91 (m, 2H), 3.21 (d, J = 3.7 Hz, 2H), 3.85 (s, 3H), 6.65 (s, 1H), 7.11-7.22 (m, 6H), 7.28-7.33 (m 2H), 7.43-7.52 (m, 1H) |
| ¹³C NMR (50 MHz, CDCl₃) | δ 29.1, 33.9, 50.4, 53.9, 56.0, 59.9, 110.5, 123.6, 125.4, 125.6, 126.0, 127.0, 128.4, 128.7, 129.1, 129.7, 131.5, 134.1, 134.9, 140.4, 141.1, 145.2 |
| ESI-MS | m/z 394 ([M + H]⁺) |
| EIHR-MS | calcd for $C_{24}H_{25}ClNO_2$ [M + H]⁺, 394.1574; found, 394.1571 |
| Compound number | 40 |
| Name | 8-(2-Acetylphenyl)-6methoxy-2-phenethyl-1,2,3,4-tetrahydroisoquinolin-7-ol |
| ¹H NMR (200 MHz, CDCl₃) | δ 2.15 (s, 3H), 2.53-3.00 (m. 8H), 3.05 (d, J = 15.4 Hz, 1H), 3.28 (d, J = 15.1 Hz, 1H), 3.87 (s, 3H), 5.59 (bs, 1H), 6.65 (s, 1H), 7.06-7.61 (m, 8H), 7.76 (dd, J = 7.5, 1.6 Hz, 1H) |
| ESI-MS | m/z 402 ([M + H]⁺) |
| EIHR-MS | calcd for $C_{26}H_{28}NO_3$ [M + H]⁺, 402.2069; found, 402.2061 |
| Compound number | 41 |
| Name | 8-(2-Fluorophenyl)-6-methoxy-2-phenethyl-1,2,3,4-tetrahydroisoquinolin-7-ol |
| ¹H NMR (200 MHz, CDCl₃) | δ 2.61-2.68 (m, 2H), 2.72-2.84 (m, 4H), 2.88-2.92 (m, 2H), 3.23 (d, J = 15.0 Hz, 1H), 3.37 (d, J = 15.0 Hz, 1H), 3.89 (s, 3H), 5.52 (s, 1H), 6.67 (s, 1H), 7.12-7.35 (m, 9H) |
| ¹³C NMR (50 MHz, CDCl₃) | δ 29.3, 34.0, 50.5, 54.3, 56.1, 60.1, 110.7, 115.9 (d, J = 22.3 Hz), 119.7, 123.1 (d, J = 17.7 Hz), 124.2, 125.6, 126.1, 128.4, 128.8, 129.7 (d, J = 7.9 Hz), 132.0, 140.1, 141.5, 145.2, 160.1 (d, J = 244 Hz) |
| ESI-MS | m/z 378.2 ([M + H]⁺) |
| Compound number | 42 |
| Name | (2-Methylphenyl)-6-methoxy-2-phenethyl-1,2,3,4-tetrahydroisoquinolin-7-ol |
| ¹H NMR (200 MHz, CDCl₃) | δ 2.09 (s, 3H), 2.57-2.65 (m, 2H), 2.71-2.81 (m, 4H), 2.90-2.92 (m, 2H), 3.02 (d, J = 15.3 Hz, 1H), 3.25 (d, J = 15.2 Hz, 1H), 3.89 (s, 3H), 5.33 (s, 1H), 6.64 (s, 1H), 7.09-7.31 (m, 9H) |
| ¹³C NMR (50 MHz, CDCl₃) | δ 19.7, 29.4, 33.9, 50.6, 54.6, 56.1, 60.2, 110.0, 125.5, 125.6, 126.1, 128.0, 128.4, 128.8, 129.8, 130.3, 135.0, 137.0, 140.4, 140.7, 145.3 |
| ESI-MS | m/z 374.2 ([M + H]⁺) |
| Compound number | 43 |
| Name | 8-(2-Isopropylphenyl)-6-methoxy-2-phenethyl-1,2,3,4-tetrahydroisoquinolin-7-ol |
| ¹H NMR (200 MHz, CDCl₃) | δ 1.12-1.17 (m, 3H), 1.26-1.30 (m, 3H), 2.65-2.94 (m, 8H), 3.12-3.20 (m, 2H), 3.63-3.65 (m, 1H), 3.91 (s, 3H), 5.30 (s, 1H), 6.67 (s, 1H), 7.06-7.42 (m, 9H) |
| ¹³C NMR (50 MHz, CDCl₃) | δ 24.0, 24.5, 29.3, 30.3, 33.9, 50.7, 54.7, 56.0, 60.2, 110.0, 125.5, 125.8, 126.1, 128.4, 128.7, 128.9, 129.9, 133.5, 140.3, 141.0, 145.2, 147.7 |
| ESI-MS | m/z 402.2 ([M + H]⁺) |
| Compound number | 44 |
| Name | 8-(3,5-Dimethoxyphenyl)-6-methoxy-2-phenethyl-1,2,3,4-tetrahydroisoquinolin-7-ol |
| ¹H NMR (200 MHz, CDCl₃) | δ 2.58-2.72 (m, 2H), 2.73-2.82 (m, 4H), 2.93 (t, J = 3.0 Hz, 2H), 3.33 (s, 2H), 3.79 (s, 6H), 3.90 (s, 3H), 5.36 (s, 1H), 6.40 (s, 1H), 6.41 (s, 1H), 6.64 (s, 1H) |

TABLE 7-continued

The analytical data of the compounds in this invention

| | |
|---|---|
| | 6.46-6.50 (m, 1H), 7.11-7.23 (m, 4H), 7.27-7.32 (m, 1H) |
| $^{13}$C NMR (50 MHz, CDCl$_3$) | δ 29.5, 34.1, 50.6, 54.8, 55.5, 56.2, 60.2, 100.0, 107.6, 110.3, 125.6, 126.1, 126.3, 128.5, 128.8, 137.5, 140.4, 140.8, 145.4, 161.0 |
| ESI-MS | m/z 420 ([M + H]$^+$) |
| EIHR-MS | calcd for C$_{26}$H$_{30}$NO$_4$ [M + H]$^+$, 420.2175; found, 420.2167 |
| Compound number | 45 |
| Name | 8-(2,3-Dimethoxyphenyl)-6-methoxy-2-phenethyl-1,2,3,4-tetrahydroisoquinolin-7-ol |
| $^1$H NMR (200 MHz, CDCl$_3$) | δ 2.54-2.86 (m, 6H), 2.87-3.00 (m, 2H), 3.28 (s, 2H), 3.62 (s, 3H), 3.89 (s, 3H), 3.90 (s, 3H), 5.46 (s, 1H), 6.65 (s, 1H), 6.73 (dd, J = 7.6, 1.5 Hz, 1H), 6.95 (dd, J = 8.2, 1.4 Hz, 1H), 7.07-7.29 (m, 6H) |
| $^{13}$C NMR (50 MHz, CDCl$_3$) | δ 29.3, 33.9, 50.6, 54.2, 55.8, 56.0, 60.0, 60.8, 110.2, 112.0, 122.6, 123.1, 124.3, 125.3, 126.0, 126.2, 128.4, 128.8, 129.7, 140.5, 140.9, 145.1, 147.0, 153.1 |
| ESI-MS | m/z 420 ([M + H]$^+$) |
| EIHR-MS | calcd for C$_{26}$H$_{30}$NO$_4$ [M + H]$^+$, 420.2175; found, 420.2159 |
| Compound number | 60 |
| Name | 8-Bromo-6-methoxy-2-phenethyl-1,2,3,4-tetrahydroisoquinolin-7-ol |
| $^1$H NMR (200 MHz, CDCl$_3$) | δ 2.70-3.01 (m, 8H), 3.64 (s, 2H), 3.86 (s, 3H), 6.58 (s, 1H), 7.17-7.37 (m, 5H) |
| $^{13}$C NMR (50 MHz, CDCl$_3$) | δ 29.3, 34.0, 50.4, 56.2, 56.4, 60.2, 109.0, 110.1, 126.2, 126.5, 127.3, 128.6, 128.9, 140.3, 141.2, 145.6 |
| ESI-MS | calcd for C$_{18}$H$_{21}$BrNO$_2$ m/z 362.1 |
| EIHR-MS | calcd for C$_{18}$H$_{21}$BrNO$_2$ [M + H]$^+$, 362.0755; found, 362.0782 |
| Compound number | 61 |
| Name | 6-Methoxy-2-(2-(1-naphthyl)ethyl)-1,2,3,4-tetrahydroisoquinolin-7-ol |
| $^1$H NMR (200 MHz, CDCl$_3$) | δ 2.68-2.97 (m, 6H), 3.23-3.47 (m, 2H), 3.68 (s, 2H), 3.83 (s, 3H), 6.58 (s, 1H), 6.60 (s, 1H), 7.28-7.58 (m, 4H), 7.64-7.91 (m, 2H), 8.00-8.17 (m, 1H) |
| $^{13}$C NMR (50 MHz, CDCl$_3$) | δ 28.8, 31.1, 51.3, 55.6, 56.0, 59.4, 110.8, 112.6, 123.9, 125.4, 125.6, 125.7, 126.1, 126.7, 127.0, 127.1, 128.9, 132.0, 134.0, 136.5, 144.0, 145.6 |
| EIHR-MS | calcd for C$_{22}$H$_{23}$NO$_2$ [M]$^+$, 333.1729; found, 333.1721 |
| Compound number | 62 |
| Name | 2-(2-(3-indolyl)ethyl)-6-methoxy-1,2,3,4-tetrahydroisoquinolin-7-ol |
| $^1$H NMR (200 MHz, CDCl$_3$) | δ 2.76-2.94 (m, 6H), 3.00-3.15 (m, 2H), 3.66 (s, 2H), 3.85 (s, 3H), 6.59 (s, 1H), 6.61 (s, 1H), 7.02-7.24 (m, 3H), 7.32-7.40 (m, 1H), 7.61-7.69 (m, 1H), 8.03 (s, 1H) |
| $^{13}$C NMR (50 MHz, CDCl$_3$) | δ 23.2, 28.7, 51.1, 55.5, 55.9, 58.9, 110.7, 111.1, 112.3, 114.4, 118.8, 119.2, 121.5, 121.9, 125.5, 127.3, 127.5, 136.2, 143.7, 145.3 |
| EIHR-MS | calcd for C$_{20}$H$_{22}$N$_2$O$_2$ [M]$^+$, 322.1681; found, 322.1675 |
| Compound number | 63 |
| Name | 6-Methoxy-2-(2-nitrophenethyl)-1,2,3,4-tetrahydroisoquinolin-7-ol |
| $^1$H NMR (200 MHz, CDCl$_3$) | δ 2.78-2.86 (m, 6H), 3.16-3.23 (m, 2H), 3.63 (s, 2H), 3.85 (s, 3H), 6.58 (s, 1H), 6.59 (s, 1H), 7.36-7.44 (m, 2H), 7.49-7.53 (m, 1H), 7.92 (dd, J = 8.1, 1.3 Hz, 1H) |
| $^{13}$C NMR (50 MHz, CDCl$_3$) | δ 28.9, 31.0, 50.9, 55.5, 56.1, 58.8, 110.8, 112.4, 125.6, 127.4, 132.7, 133.2, 135.5, 143.8, 145.4, 149.6 |
| ESI-MS | m/z 329.2 ([M + H]$^+$), 351.1 ([M + Na]$^+$) |
| Compound number | 64 |
| Name | 6-Methoxy-2-(3-nitrophenethyl)-1,2,3,4-tetrahydroisoquinolin-7-ol |
| $^1$H NMR (200 MHz, CDCl$_3$) | δ 2.73-2.89 (m, 6H), 2.95-3.03 (m, 2H), 3.58 (s, 2H), 3.82 (s, 1H), 5.73 (s, 1H), 6.55 (s, 2H), 7.42 (t, J = 7.8 Hz, 1H), 7.52, (d, J = 7.6 Hz, 1H), 8.03-809 (m, 2H) |
| $^{13}$C NMR (50 MHz, CDCl$_3$) | δ 28.8, 33.6, 51.2, 55.6, 56.1, 59.4, 110.8, 112.4, 121.4, 123.7, 125.5, 127.0, 129.4, 135.3, 142.5, 143.9, 145.5, 148.4 |
| ESI-MS | m/z 329.2 ([M + H]$^+$), 351.1 ([M + Na]$^+$) |
| Compound number | 65 |
| Name | 6-Methoxy-2-(4-nitrophenethyl)-1,2,3,4-tetrahydroisoquinolin-7-ol |
| $^1$H NMR (200 MHz, CDCl$_3$) | δ 2.74-2.86 (m, 6H), 2.97-3.04 (m, 2H), 3.60 (s, 2H), 3.85 (s, 3H), 6.57 (s, 2H), 7.36-7.43 (m, 2H), 8.11-8.18 (m, 2H) |
| $^{13}$C NMR (50 MHz, CDCl$_3$) | δ 28.8, 33.9, 51.2, 55.6, 56.1, 59.3, 110.8, 112.4, 123.8, 125.5, 127.0, 129.7, 143.9, 145.5, 146.6, 148.5 |
| ESI-MS | ESIMS m/z 329.1 ([M + H]$^+$) |
| Compound number | 66 |
| Name | 2-(4-Chlorophenethyl)-6-methoxy-1,2,3,4-tetrahydroisoquinolin-7-ol |
| $^1$H NMR (200 MHz, CDCl$_3$) | δ 2.66-2.93 (m, 8H), 3.58 (s, 2H), 3.83 (s, 3H), 6.54 (s, 1H), 6.56 (s, 1H), 7.11-7.19 (m, 2H), 7.21-7.28 (m, 2H) |
| $^{13}$C NMR (50 MHz, CDCl$_3$) | δ 28.7, 33.3, 51.2, 55.5, 56.0, 60.0, 110.8, 112.5, 125.4, 127.0, 128.6, 130.2, 131.9, 138.9, 143.9, 145.5 |
| EIHR-MS | calcd for C$_{18}$H$_{20}$ClNO$_2$ [M]$^+$, 317.1183; found, 317.1180 |
| Compound number | 67 |
| Name | 2-(2,4-Dichlorophenethyl)-6-methoxy-1,2,3,4-tetrahydroisoquinolin-7-ol |
| $^1$H NMR (200 MHz, CDCl$_3$) | δ 2.63-2.91 (m, 8H), 3.61 (s, 2H), 3.83 (s, 3H), 6.56 (s, 2H), 7.15-7.24 (m, 2H), 7.33-7.43 (m, 1H) |
| $^{13}$C NMR (50 MHz, CDCl$_3$) | δ 28.8, 31.0, 51.0, 55.5, 56.0, 57.8, 110.8, 112.5, 125.5, 127.1, 127.2, 129.3, 131.7, 132.6, 134.8, 136.6, 143.9, 145.4 |
| EIHR-MS | calcd for C$_{18}$H$_{19}$Cl$_2$NO$_2$ [M]$^+$, 351.0793; found, 351.0799 |
| Compound number | 68 |
| Name | 2-(4-Bromophenethyl)-6-methoxy-1,2,3,4-tetrahydroisoquinolin-7-ol |
| $^1$H NMR (200 MHz, CDCl$_3$) | δ 2.67-2.92 (m, 8H), 3.59 (s, 2H), 3.84 (s, 3H), 6.57 (s, 2H), 7.07-7.15 (m, 2H), 7.37-7.44 (m, 2H) |
| $^{13}$C NMR (50 MHz, CDCl$_3$) | δ 28.8, 33.5, 51.2, 55.6, 56.1, 60.0, 110.8, 112.4, 120.0, 125.5, 127.2, 130.6, 130.6, 139.5, 143.9, 145.4 |
| EIHR-MS | calcd for C$_{18}$H$_{20}$BrNO$_2$ [M]$^+$, 313.0677; found, 313.0676 |
| Compound number | 69 |
| Name | 2-(3-Bromophenethyl)-6-methoxy-1,2,3,4-tetrahydroisoquinolin-7-ol |
| $^1$H NMR (200 MHz, CDCl$_3$) | δ 2.67-2.93 (m, 8H), 3.59 (s, 2H), 3.84 (s, 3H), 6.57 (s, 2H), 7.13-7.19 (m, 2H), 7.28-7.40 (m, 2H) |
| $^{13}$C NMR (50 MHz, CDCl$_3$) | δ 28.8, 33.7, 51.2, 55.6, 56.1, 60.0, 110.8, 112.4, 122.5, 125.5, 127.2, 127.6, 129.3, 130.1, 131.9, 142.9, 143.9, 145.4 |
| EIHR-MS | calcd for C$_{18}$H$_{20}$BrNO$_2$ [M]$^+$, 313.0677; found, 313.0665 |
| Compound number | 70 |
| Name | 6-Methoxy-2-(3-Methoxyphenethyl)-1,2,3,4-tetrahydroisoquinolin-7-ol |
| $^1$H NMR (200 MHz, CDCl$_3$) | δ 2.69-2.96 (m, 8H), 3.60 (s, 2H), 3.80 (s, 3H), 3.84 (s, 3H), 6.57 (s, 2H), 6.72-6.88 (m, 3H), 7.16-7.28 (m, 1H) |
| $^{13}$C NMR (50 MHz, CDCl$_3$) | δ 28.8, 34.1, 51.2, 55.3, 55.6, 56.1, 60.3, 110.8, 111.5, 112.1, 112.4, 114.6, 121.2, 125.5, 127.2, 129.5, 142.1, 143.8, 145.4, 159.7 |
| EIHR-MS | calcd for C$_{19}$H$_{23}$NO$_3$ [M]$^+$, 313.1678; found, 313.1678 |
| Compound number | 71 |
| Name | 2-Heptyl-6-methoxy-1,2,3,4-tetrahydroisoquinolin-7-ol |
| $^1$H NMR (200 MHz, CDCl$_3$) | δ 0.85-0.88 (m, 3H), 1.18-1.50 (m, 8H), 1.50-1.70 (m, 2H), 2.43-2.51 (m, 2H), 2.66-2.71 (m, 2H), 2.78-2.81 (m, 2H), 3.50 (s, 2H), 3.83 (s, 3H), 6.55 (s, 2H) |
| $^{13}$C NMR (50 MHz, CDCl$_3$) | δ 14.2, 22.8, 27.3, 27.8, 28.8, 29.4, 32.0, 51.2, 55.7, 56.0, 58.7, 110.8, 112.5, 125.6, 127.6, 143.8, 145.4 |
| ESI-MS | m/z 278.2 ([M + H]$^+$) |
| Compound number | 72 |
| Name | 6-Methoxy-2-octyl-1,2,3,4-tetrahydroisoquinolin-7-ol |

TABLE 7-continued

The analytical data of the compounds in this invention

| | |
|---|---|
| $^1$H NMR (200 MHz, CDCl$_3$) | δ 0.88 (s, 3H), 1.18-1.50 (m, 10H), 1.50-1.70 (m, 2H), 2.43-2.51 (m, 2H), 2.66-2.71 (m, 2H), 2.78-2.81 (m, 2H), 3.50 (s, 2H), 3.84 (s, 3H), 6.56 (s, 2H) |
| $^{13}$C NMR (50 MHz, CDCl$_3$) | δ 14.3, 22.8, 27.3, 27.8, 28.8, 29.4, 29.7, 32.0, 51.2, 55.8, 56.1, 58.7, 110.8, 112.5, 125.6, 127.5, 143.8, 145.4 |
| ESI-MS | m/z 292.2 ([M + H]$^+$) |
| Compound number | 73 |
| Name | 6-Methoxy-2-nonyl-1,2,3,4-tetrahydroisoquinolin-7-ol |
| $^1$H NMR (200 MHz, CDCl$_3$) | δ 0.88 (s, 3H), 1.28 (bs, 12H), 1.50-1.70 (m, 2H), 2.43-2.51 (m, 2H), 2.69-2.72 (m, 2H), 2.79-2.81 (m, 2H), 3.50 (s, 2H), 3.83 (s, 3H), 6.55 (s, 2H) |
| $^{13}$C NMR (50 MHz, CDCl$_3$) | δ 14.3, 22.8, 27.3, 27.8, 28.8, 29.4, 29.7, 32.0, 51.2, 55.7, 56.1, 58.7, 110.8, 112.5, 125.7, 127.5, 143.8, 145.4 |
| ESI-MS | m/z 306.2 ([M + H]$^+$) |
| Compound number | 74 |
| Name | 2-(3,4-Dimethoxyphenethyl)-6-methoxy-1,2,3,4-tetrahydroisoquinolin-7-ol |
| $^1$H NMR (200 MHz, CDCl$_3$) | δ 2.68-2.93 (m, 8H), 3.60 (s, 2H), 3.84 (s, 3H), 3.86 (s, 3H), 3.87 (s, 3H), 6.57 (s, 2H), 6.73-6.84 (m, 3H) |
| $^{13}$C NMR (50 MHz, CDCl$_3$) | δ 28.8, 33.6, 51.3, 55.6, 56.0, 60.5, 110.8, 111.3, 112.1, 112.4, 120.6, 125.5, 127.2, 133.0, 143.8, 145.4, 147.4, 148.9 |
| EIHR-MS | calcd for C$_{20}$H$_{25}$NO$_4$ [M]$^+$, 343.1784; found, 343.1788 |
| Compound number | 75 |
| Name | 2-(2-Chlorophenethyl)-6-methoxy-1,2,3,4-tetrahydroisoquinolin-7-ol |
| $^1$H NMR (200 MHz, CDCl$_3$) | δ 2.68-2.90 (m, 6H), 2.98-3.11 (m, 2H), 3.63 (s, 2H), 3.83 (s, 3H), 6.57 (s, 2H), 7.09-7.24 (m, 2H), 7.24-7.39 (m, 2H) |
| $^{13}$C NMR (50 MHz, CDCl$_3$) | δ 28.8, 31.6, 55.5, 56.0, 58.1, 110.8, 112.5, 125.5, 127.0, 127.2, 127.7, 129.6, 131.0, 134.1, 138.0, 143.8, 145.4 |
| ESI-MS | m/z 318 ([M + H]$^+$), 340 ([M + Na]$^+$) |
| EIHR-MS | calcd for C$_{18}$H$_{21}$ClNO$_2$ [M + H]$^+$, 318.1261; found, 318.1253 |
| Compound number | 76 |
| Name | 2-(2-Fluorophenethyl)-6-methoxy-1,2,3,4-tetrahydroisoquinolin-7-ol |
| $^1$H NMR (200 MHz, CDCl$_3$) | δ 2.68-2.89 (m, 6H), 2.89-3.01 (m, 2H), 3.61 (s, 2H), 3.83 (s, 3H), 6.56 (s, 2H), 6.94-7.11 (m, 2H), 7.12-7.30 (m, 2H) |
| $^{13}$C NMR (50 MHz, CDCl$_3$) | δ 27.2, 28.8, 51.1, 55.5, 56.0, 58.6, 110.8, 112.5, 115.4 (J = 22.1 Hz), 124.1 (J = 3.1 Hz), 125.5, 127.2 (J = 15.9 Hz), 127.3, 127.9 (J = 7.9 Hz), 131.1 (J = 4.8 Hz), 143.8, 145.4, 161.3 (J = 243 Hz) |
| ESI-MS | m/z 302 ([M + H]$^+$) |
| EIHR-MS | calcd for C$_{18}$H$_{21}$FNO$_2$ [M + H]$^+$, 302.1556; found, 302.1554 |
| Compound number | 77 |
| Name | 6-Methoxy-2-(3-(4-nitrophenyl)propyl)-1,2,3,4-tetrahydroisoquinolin-7-ol |
| $^1$H NMR (200 MHz, CDCl$_3$) | δ 1.84-2.05 (m, 2H), 2.44-2.56 (m, 2H), 2.63-2.74 (m, 2H), 2.74-2.88 (m, 4H), 3.50 (s, 2H), 3.83 (s, 3H), 6.54 (s, 1H), 6.56 (s, 1H), 7.30-7.42 (m, 2H), 8.09-8.20 (m, 2H) |
| $^{13}$C NMR (50 MHz, CDCl$_3$) | δ 28.4, 28.8, 33.6, 51.2, 55.6, 56.0, 57.3, 110.8, 112.4, 123.7, 125.5, 127.2, 129.4, 143.8, 145.4, 146.4, 150.3 |
| EIHR-MS | calcd for C$_{19}$H$_{23}$N$_2$O$_4$ [M + H]$^+$, 343.1658; found, 343.1661 |
| Compound number | 78 |
| Name | 6-Methoxy-2-(3-(2-nitrophenyl)propyl)-1,2,3,4-tetrahydroisoquinolin-7-ol |
| $^1$H NMR (200 MHz, CDCl$_3$) | δ 1.80-2.09 (m, 2H), 2.44-2.63 (m, 2H), 2.64-2.75 (m, 2H), 2.76-2.88 (m, 2H), 2.88-3.07 (m, 2H), 3.51 (s, 2H), 3.83 (s, 3H), 6.55 (s, 1H), 6.56 (s, 1H), 7.28-7.43 (m, 2H), 7.45-7.58 (m, 1H), 7.83-7.95 (m, 1H) |
| $^{13}$C NMR (50 MHz, CDCl$_3$) | δ 28.2, 28.8, 31.0, 51.0, 55.7, 56.0, 57.7, 110.8, 112.4, 124.8, 126.1, 127.1, 127.4, 132.2, 133.0, 137.4, 143.8, 145.4, 149.5 |
| EIHR-MS | calcd for C$_{19}$H$_{23}$N$_2$O$_4$ [M + H]$^+$, 343.1658; found, 343.1661 |
| Compound number | 85 |
| Name | 8-Bromo-6-methoxy-2-(4-nitrophenethyl)-1,2,3,4-tetrahydroisoquinolin-7-ol |
| $^1$H NMR (200 MHz, CDCl$_3$) | δ 2.71-2.93 (m, 6H), 2.97-3.10 (m, 2H), 3.62 (s, 2H), 3.87 (s, 3H), 6.59 (s, 1H), 7.37-7.46 (m, 2H), 8.12-8.20 (m, 2H) |
| $^{13}$C NMR (50 MHz, CDCl$_3$) | δ 29.3, 33.9, 50.4, 56.1, 56.4, 59.1, 108.8, 110.1, 123.8, 126.2, 127.1, 129.7, 141.3, 145.6, 146.6, 148.4 |
| ESI-MS | m/z 407 ([M + H]$^+$), 429 ([M + Na]$^+$) |
| EIHR-MS | calcd for C$_{18}$H$_{20}$BrN$_2$O$_4$ [M + H]$^+$, 407.0606; found, 407.0585 |
| Compound number | 95 |
| Name | 8-Bromo-2-(2-chlorophenethyl)-6-methoxy-1,2,3,4-tetrahydroisoquinolin-7-ol |
| $^1$H NMR (200 MHz, CDCl$_3$) | δ 2.72-2.93 (m, 6H), 2.98-3.15 (m, 2H), 3.66 (s, 2H), 3.86 (s, 3H), 6.11 (bs, 1H), 6.58 (s, 1H), 7.10-7.25 (m, 2H), 7.25-7.41 (m, 2H) |
| $^{13}$C NMR (50 MHz, CDCl$_3$) | δ 29.4, 31.6, 50.2, 56.2, 56.4, 58.0, 108.9, 110.2, 126.6, 127.0, 127.3, 127.8, 129.7, 131.0, 134.2, 138.0, 141.2, 145.5 |
| ESI-MS | m/z 396 ([M + H]$^+$) |
| EIHR-MS | calcd for C$_{18}$H$_{20}$BrClNO$_2$ [M + H]$^+$, 396.0366; found, 396.0355 |
| Compound number | 96 |
| Name | 8-Bromo-2-(2-fluorophenethyl)-6-methoxy-1,2,3,4-tetrahydroisoquinolin-7-ol |
| $^1$H NMR (200 MHz, CDCl$_3$) | δ 2.69-2.91 (m, 6H), 2.91-3.05 (m, 2H), 3.63 (s, 2H), 3.85 (s, 3H), 6.57 (s, 1H), 6.94-7.12 (m, 2H), 7.12-7.33 (m, 2H) |
| $^{13}$C NMR (50 MHz, CDCl$_3$) | δ 27.2, 29.3, 50.2, 56.2, 56.4, 58.4, 109.1, 110.2, 115.4 (J = 21.9 Hz), 124.1 (J = 3.2 Hz), 126.5, 127.0, 127.2, 128.0 (J = 8.1 Hz), 131.1 (J = 5.0 Hz), 141.2, 145.6, 161.3 (J = 243 Hz) |
| ESI-MS | m/z 380 ([M + H]$^+$) |
| EIHR-MS | calcd for C$_{18}$H$_{20}$BrFNO$_2$ [M + H]$^+$, 380.0661; found, 380.0662 |
| Compound number | 97 |
| Name | 8-Bromo-6-methoxy-2-(3-(4-nitrophenyl)propyl)-1,2,3,4-tetrahydroisoquinolin-7-ol |
| $^1$H NMR (200 MHz, CDCl$_3$) | δ 1.87-2.06 (m, 2H), 2.49-2.74 (m, 4H), 2.74-2.90 (m, 4H), 3.53 (s, 2H), 3.85 (s, 3H), 6.57 (s, 1H), 7.31-7.43 (m, 2H), 8.07-8.21 (m, 2H) |
| $^{13}$C NMR (50 MHz, CDCl$_3$) | δ 28.4, 29.3, 33.6, 50.4, 56.2, 56.4, 57.2, 109.0, 110.1, 123.8, 126.4, 127.2, 129.4, 141.3, 145.6, 146.4, 150.2 |
| ESI-MS | m/z 421 ([M + H]$^+$) |
| EIHR-MS | calcd for C$_{19}$H$_{22}$BrN$_2$O$_4$ [M + H]$^+$, 421.0763; found, 421.0757 |
| Compound number | 98 |
| Name | 8-Bromo-6-methoxy-2-(3-(2-nitrophenyl)propyl)-1,2,3,4-tetrahydroisoquinolin-7-ol |
| $^1$H NMR (200 MHz, CDCl$_3$) | δ 1.86-2.11 (m, 2H), 2.51-2.75 (m, 4H), 2.75-2.90 (m, 2H), 2.90-3.06 (m, 2H), 3.53 (s, 2H), 3.83 (s, 3H), 6.55 (s, 1H), 7.31-7.43 (m, 2H), 7.45-7.58 (m, 1H), 7.82-7.94 (m, 1H) |
| $^{13}$C NMR (50 MHz, CDCl$_3$) | δ 28.1, 29.2, 30.9, 50.1, 56.3, 57.5, 109.1, 110.1, 124.8, 126.5, 127.1, 127.3, 132.1, 133.0, 137.3, 141.2, 145.7, 149.4 |
| ESI-MS | m/z 421 ([M + H]$^+$) |
| Compound number | 101 |
| Name | 8-(2,4-Dimethoxyphenyl)-6-methoxy-2-(2-(1-naphthyl)ethyl)-1,2,3,4-tetrahydroisoquinolin-7-ol |
| $^1$H NMR (200 MHz, CDCl$_3$) | δ 2.69-3.02 (m, 6H), 3.19-3.37 (m, 4H), 3.73 (s, 3H), 3.82-3.93 (m, 6H), 6.54-6.63 (m, 1H), 6.63-6.72 (m, 1H), 7.03-7.12 (m, 1H), 7.25-7.29 (m, 1H), 7.29-7.35 (m, 1H), 7.35-7.43 (m, 1H), 7.43-7.55 (m, 1H), 7.65-7.76 (m, 1H), 7.79-7.89 (m, 1H), 7.95-8.04 (m, 1H) |
| $^{13}$C NMR (50 MHz, CDCl$_3$) | δ 29.2, 31.1, 50.7, 54.3, 55.5, 55.8, 56.1, 59.2, 99.2, 104.9, 110.3, 116.3, 122.6, 123.9 (×2), 125.1, 125.6, 125.7, 126.0, 126.7, 127.0, 128.9, 132.0 (×2), 134.0, 136.6, 141.5, 145.4, 158.2, 160.9 |

TABLE 7-continued

The analytical data of the compounds in this invention

| | |
|---|---|
| Compound number | 102 |
| Name | 8-(2,4-Dimethoxyphenyl)-2-(2-(3-indolyl)ethyl)-6-methoxy-1,2,3,4-tetrahydroisoquinolin-7-ol |
| $^1$H NMR (200 MHz, CDCl$_3$) | δ 2.72-3.42 (m, 10H), 3.70 (s, 3H), 3.85 (s, 3H), 3.88 (s, 3H), 6.53-6.70 (m, 2H), 6.73-6.87 (m, 1H), 6.94-7.23 (m, 5H), 7.28-7.40 (m, 1H), 7.51-7.69 (m, 1H) |
| Compound number | 105 |
| Name | 8-(2,4-Διμετηοξψπηενψλ)-6-μετηοξψ-2-(4-νιτροπηενετηψλ)-1,2,3,4-τετραηψδροισοθυινολιν-7-ολ |
| $^1$H NMR (200 MHz, CDCl$_3$) | δ 2.61-2.81 (m, 4H), 2.82-2.95 (m, 4H), 3.23 (s, 2H), 3.72 (s, 3H), 3.85 (s, 3H), 3.88 (s, 3H), 6.53-6.61 (m, 2H), 6.63 (s, 1H), 6.91-7.17 (m, 1H), 7.25-7.35 (m, 2H), 8.05-8.13 (m, 2H) |
| $^{13}$C NMR (50 MHz, CDCl$_3$) | δ 29.3, 33.7, 50.7, 54.2, 55.5, 55.7, 56.0, 59.1, 99.2, 104.8, 110.2, 116.3, 122.4, 123.7, 125.0, 126.4, 129.6, 131.9, 141.4, 145.2, 146.5, 148.6, 158.1, 160.8 |
| EIHR-MS | calcd for C$_{26}$H$_{29}$N$_2$O$_6$ [M + H]$^+$, 465.2025; found, 465.2055 |
| Compound number | 106 |
| Name | 2-(4-Chlorophenethyl)-8-(2,4-dimethoxyphenyl)-6-methoxy-1,2,3,4-tetrahydroisoquinolin-7-ol |
| $^1$H NMR (200 MHz, CDCl$_3$) | δ 2.47-2.77 (m, 6H), 2.77-2.88 (m, 2H), 3.16 (s, 2H), 3.65 (s, 3H), 3.78 (s, 3H), 3.80 (s, 3H), 6.47-6.54 (m, 2H), 6.55 (s, 1H), 6.93-7.05 (m, 3H), 7.09-7.20 (m, 2H) |
| $^{13}$C NMR (50 MHz, CDCl$_3$) | δ 29.3, 33.3, 50.6, 54.2, 55.4, 55.7, 56.0, 59.8, 99.2, 104.8, 110.2, 116.3, 122.5, 125.1, 126.6, 128.5, 130.1, 131.7, 131.9, 139.0, 141.4, 145.2, 158.1, 160.7 |
| ESI-MS | m/z 452 ([M − H]$^+$), 476 ([M + Na]$^+$) |
| EIHR-MS | calcd for C$_{26}$H$_{27}$ClNO$_4$ [M − H$^+$], 452.1629; found, 452.1623 |
| Compound number | 107 |
| Name | 2-(2,4-Dichlorophenethyl)-8-(2,4-dimethoxyphenyl)-6-methoxy-1,2,3,4-tetrahydroisoquinolin-7-ol |
| $^1$H NMR (200 MHz, CDCl$_3$) | δ 2.54-2.65 (m, 2H), 2.69-2.95 (m, 6H), 3.26 (s, 2H), 3.73 (s, 3H), 3.85 (s, 3H), 3.88 (s, 3H), 6.54-6.61 (m, 2H), 6.63 (s, 1H), 7.02-7.07 (m, 1H), 7.12 (s, 1H), 7.12 (s, 1H), 7.30-7.33 (m, 1H) |
| ESI-MS | m/z 488 ([M + H]$^+$) |
| EIHR-MS | calcd for C$_{26}$H$_{26}$Cl$_2$NO$_4$ [M − H]$^+$, 486.1239; found, 486.1233 |
| Compound number | 108 |
| Name | 2-(4-Bromophenethyl)-8-(2,4-dimethoxyphenyl)-6-methoxy-1,2,3,4-tetrahydroisoquinolin-7-ol |
| $^1$H NMR (200 MHz, CDCl$_3$) | δ 2.53-2.83 (m, 6H), 2.84-2.96 (m, 2H), 3.23 (bd, 2H), 3.72 (s, 3H), 3.85 (s, 3H), 3.87 (s, 3H), 6.53-6.62 (m, 2H), 6.62 (s, 1H), 6.98-7.07 (m, 3H), 7.28-7.42 (m, 2H) |
| $^{13}$C NMR (50 MHz, CDCl$_3$) | δ 29.3, 33.4, 50.6, 54.2, 55.5, 55.7, 56.0, 59.7, 99.2, 104.8, 110.2, 116.3, 119.8, 122.5, 125.1, 126.6, 130.6, 131.4, 131.9, 139.6, 141.4, 145.3, 158.2, 160.8 |
| ESI-MS | m/z 496 ([M − H]$^+$) |
| EIHR-MS | calcd for C$_{26}$H$_{27}$BrNO$_4$ [M − H]$^+$, 496.1123; found, 496.1118 |
| Compound number | 109 |
| Name | 2-(3-Bromophenethyl)-8-(2,4-dimethoxyphenyl)-6-methoxy-1,2,3,4-tetrahydroisoquinolin-7-ol |
| $^1$H NMR (200 MHz, CDCl$_3$) | δ 2.54-2.83 (m, 6H), 2.83-2.96 (m, 2H), 3.13-3.33 (m, 2H), 3.72 (s, 3H), 3.85 (s, 3H), 3.87 (s, 3H), 6.54-6.61 (m, 2H), 6.62 (s, 1H), 6.99-7.15 (m, 3H), 7.24-7.35 (m, 1H) |
| $^{13}$C NMR (50 MHz, CDCl$_3$) | δ 29.2, 33.6, 50.6, 54.2, 55.4, 55.7, 56.0, 59.6, 99.2, 110.2, 116.3, 122.4, 122.5, 125.0, 126.5, 127.5, 129.1, 130.7, 131.7, 131.9, 141.4, 142.9, 145.2, 158.1, 160.8 |
| ESI-MS | m/z 498 ([M + H]$^+$) |
| EIHR-MS | calcd for C$_{26}$H$_{27}$BrNO$_4$ [M − H]$^+$, 496.1123; found, 496.1118 |
| Compound number | 110 |
| Name | 8-(2,4-Dimethoxyphenyl)-6-methoxy-2-(3-methoxyphenethyl)-1,2,3,4-tetrahydroisoquinolin-7-ol |
| $^1$H NMR (200 MHz, CDCl$_3$) | δ 2.51-2.85 (m, 6H), 2.86-2.98 (m, 2H), 3.25 (s, 2H), 3.71 (s, 3H), 3.76 (s, 3H), 3.84 (s, 3H), 3.86 (s, 3H), 6.53-6.60 (m, 2H), 6.62 (s, 1H), 6.67-6.79 (m, 3H), 7.00-7.07 (m, 1H), 7.10-7.21 (m, 1H) |
| $^{13}$C NMR (50 MHz, CDCl$_3$) | δ 29.2, 33.9, 50.5, 54.1, 55.2, 55.4, 55.6, 55.9, 59.9, 99.1, 104.8, 110.1, 111.3, 114.4, 116.3, 121.1, 122.4, 125.0, 126.5, 129.3, 131.8, 141.3, 142.0, 145.2, 158.0, 159.6, 160.7 |
| ESI-MS | m/z 448 ([M − H]$^+$), 472 ([M + Na]$^+$) |
| EIHR-MS | calcd for C$_{27}$H$_{31}$NO$_5$ [M]$^+$, 449.2202; found, 449.2197 |
| Compound number | 111 |
| Name | 8-(2,4-Dimethoxyphenyl)-2-heptyl-6-methoxy-1,2,3,4-tetrahydroisoquinolin-7-ol |
| $^1$H NMR (200 MHz, CDCl$_3$) | δ 0.83-0.89 (m, 3H), 1.10-1.39 (m, 8H), 1.40-1.45 (m, 2H), 2.31-2.38 (m, 2H), 2.63-2.71 (m, 2H), 2.85-2.91 (m, 2H), 3.16 (s, 2H), 3.73 (s, 3H), 3.86 (s, 3H), 3.87 (s, 3H), 5.30 (s, 1H), 6.46-6.61 (m, 2H), 6.67 (d, J = 8.4 Hz, 1H), 7.02-7.06 (m, 1H) |
| $^{13}$C NMR (50 MHz, CDCl$_3$) | δ 14.2, 22.8, 27.3, 27.7, 29.4, 32.0, 50.5, 54.5, 55.5, 55.7, 56.0, 58.5, 99.2, 104.8, 110.2, 125.3, 132.0, 141.3, 145.1, 158.2, 160.8 |
| ESI-MS | m/z 414.3 ([M + H]$^+$) |
| Compound number | 112 |
| Name | 8-(2,4-Dimethoxyphenyl)-6-methoxy-2-octyl-1,2,3,4-tetrahydroisoquinolin-7-ol |
| $^1$H NMR (200 MHz, CDCl$_3$) | δ 0.83-0.89 (m, 3H), 1.10-1.38 (m, 10H), 1.40-1.55 (m, 2H), 2.31-2.38 (m, 2H), 2.63-2.71 (m, 2H), 2.85-2.91 (m, 2H), 3.16 (s, 2H), 3.73 (s, 3H), 3.86 (s, 3H), 3.87 (s, 3H), 5.30 (s, 1H), 6.55-6.61 (m, 2H), 6.67 (d, J = 8.4 Hz, 1H), 7.02-7.06 (m, 1H) |
| $^{13}$C NMR (50 MHz, CDCl$_3$) | δ 14.2, 22.8, 27.3, 27.7, 29.4 (×2), 29.6, 31.9, 50.5, 54.4, 55.5, 55.7, 56.0, 58.4, 99.2, 104.8, 110.2, 125.3, 126.9, 132.0, 141.4, 145.2, 158.2 |
| ESI-MS | m/s 428.3 ([M + H]$^+$) |
| Compound number | 113 |
| Name | 8-(2,4-Dimethoxyphenyl)-6-methoxy-2-nonyl-1,2,3,4-tetrahydroisoquinolin-7-ol |
| $^1$H NMR (200 MHz, CDCl$_3$) | δ 0.84-0.90 (m, 3H), 1.24 (bs, 12H), 1.40-1.55 (m, 2H), 2.31-2.38 (m, 2H), 2.61-2.71 (m, 2H), 2.85-2.91 (m, 2H), 3.16 (s, 2H), 3.73 (s, 3H), 3.86 (s, 3H), 3.87 (s, 3H), 5.29 (s, 1H), 6.55-6.61 (m, 2H), 6.67 (d, J = 8.4 Hz, 1H), 7.02-7.06 (m, 1H) |
| $^{13}$C NMR (50 MHz, CDCl$_3$) | δ 14.2, 22.8, 27.3, 27.7, 29.4, 29.7, 32.0, 50.5, 54.5, 55.5, 55.7, 56.0, 58.4, 99.2, 104.8, 110.2, 122.5, 125.3, 127.0, 131.9, 141.4, 145.2, 158.2, 160.7 |
| ESI-MS | m/z 442.3 ([M + H]$^+$) |
| Compound number | 114 |
| Name | 2-(3,4-Dimethoxyphenethyl)-8-(2,4-dimethoxyphenyl)-6-methoxy-1,2,3,4-tetrahydroisoquinolin-7-ol |
| $^1$H NMR (200 MHz, CDCl$_3$) | δ 2.54-2.84 (m, 6H), 2.85-2.97 (m, 2H), 3.26 (bd, 2H), 3.71 (s, 3H), 3.83 (s, 3H), 3.83 (s, 6H), 3.86 (s, 3H), 6.53-6.60 (m, 2H), 6.62 (s, 1H), 6.65-6.79 (m, 3H), 7.00-7.07 (m, 1H) |
| $^{13}$C NMR (50 MHz, CDCl$_3$) | δ 29.2, 33.5, 50.5, 54.1, 55.3, 55.6, 55.8, 55.9, 60.1, 99.0, 104.7, 110.1, 111.1, 111.9, 116.3, 120.5, 122.4, 125.0, 126.5, 131.8, 133.0, 141.3, 145.1, 147.2, 148.7, 158.0, 160.6 |
| ESI-MS | m/z 478 ([M − H]$^+$), 502 ([M + Na]$^+$) |
| EIHR-MS | calcd for C$_{28}$H$_{33}$NO$_6$ [M]$^+$, 479.2308; found, 479.2302 |
| Compound number | 115 |
| Name | 2-(2-Chlorophenethyl)-8-(2,4-dimethoxyphenyl)-6-methoxy-1,2,3,4-tetrahydroisoquinolin-7-ol |
| $^1$H NMR (200 MHz, CDCl$_3$) | δ 2.48-2.60 (m, 2H), 2.63-2.93 (m, 6H), 3.20 (s, 2H), 3.63 (s, 3H), 3.75 (s, 3H), 3.77 (s, 3H), 6.44-6.52 (m, 2H), 6.54 (s, 1H), 6.92-7.14 (m, 4H), 7.15-7.25 (m, 1H) |
| $^{13}$C NMR (50 MHz, CDCl$_3$) | δ 29.2, 31.5, 50.4, 54.2, 55.4, 55.6, 55.9, 57.9, 99.1, 104.7, 110.1, 116.3, 122.5, 125.0, 126.7, 126.8, 127.5, 129.4, 130.8, 131.9, 134.0, 138.0, 141.4, 145.2, 158.1, 160.7 |

TABLE 7-continued

The analytical data of the compounds in this invention

| | |
|---|---|
| EIHR-MS | calcd for $C_{26}H_{29}ClNO_4$ [M + H]$^+$, 454.1785; found, 454.1799 |
| Compound number | 116 |
| Name | 8-(2,4-Dimethoxyphenyl)-2-(2-fluorophenethyl)-6-methoxy-1,2,3,4-tetrahydroisoquinolin-7-ol |
| $^1$H NMR (200 MHz, CDCl$_3$) | δ 2.55-2.95 (m, 8H), 3.26 (s, 2H), 3.72 (s, 3H), 3.84 (s, 3H), 3.87 (s, 3H), 6.53-6.61 (m, 2H), 6.62 (s, 1H), 6.89-7.22 (m, 5H) |
| $^{13}$C NMR (50 MHz, CDCl$_3$) | δ 27.1, 29.2, 50.4, 54.2, 55.4, 55.7, 56.0, 58.3, 99.2, 104.8, 110.2, 115.2 (J = 22.0 Hz), 116.3, 122.5, 124.0 (J = 3.0 Hz), 125.1, 126.7, 127.3 (J = 16.0 Hz), 127.8 (J = 7.9 Hz), 131.0 (J = 4.9 Hz), 131.9, 141.3, 145.2, 158.1, 160.8, 161.2 (J = 243 Hz) |
| EIHR-MS | calcd for $C_{26}H_{29}FNO_4$ [M + H]$^+$, 438.2081; found, 438.2099 |
| Compound number | 119 |
| Name | 8-(2,4-Dimethoxyphenyl)-2-(4-fluorophenethyl)-6-methoxy-1,2,3,4-tetrahydroisoquinolin-7-ol |
| $^1$H NMR (200 MHz, CDCl$_3$) | δ 2.54-2.82 (m, 6H), 2.85-2.96 (m, 2H), 3.24 (d, J = 2.1 Hz, 2H), 3.71 (s, 3H), 3.84 (s, 3H), 3.86 (s, 3H), 6.53-6.60 (m, 2H), 6.62 (s, 1H), 6.84-6.97 (m, 2H), 7.00-7.14 (m, 3H) |
| $^{13}$C NMR (50 MHz, CDCl$_3$) | δ 29.3, 33.3, 50.7, 54.3, 55.5, 55.8, 56.1, 60.1, 99.3, 104.9, 110.2, 115.0, 115.4, 116.4, 122.7, 125.1, 126.6, 130.1, 130.3, 132.0, 136.2, 141.6, 145.4, 158.2, 160.9, 161.5 (d, J = 242 Hz) |
| Compound number | 120 |
| Name | 8-(2,4-Dimethoxyphenyl)-6-methoxy-2-(4-methoxyphenethyl)-1,2,3,4-tetrahydroisoquinolin-7-ol |
| $^1$H NMR (200 MHz, CDCl$_3$) | δ 2.54-2.80 (m, 6H), 2.84-2.93 (m, 2H), 3.25 (s, 2H), 3.71 (s, 3H), 3.76 (s, 3H), 3.84 (s, 3H), 3.87 (s, 3H), 6.54-6.60 (m, 2H), 6.62 (s, 1H), 6.75-6.83 (m, 2H), 7.01-7.11 (m, 3H) |
| $^{13}$C NMR (50 MHz, CDCl$_3$) | δ 29.3, 33.1, 50.6, 54.2, 55.3, 55.4, 55.7, 56.0, 60.4, 99.1, 104.8, 110.2, 113.8, 116.4, 122.5, 125.1, 126.7, 129.6, 131.9, 132.6, 141.4, 145.2, 157.9, 158.1, 160.7 |
| ESI-MS | m/z 448 ([M − H]$^+$), 472 ([M + Na]$^+$) |
| EIHR-MS | calcd for $C_{27}H_{31}NO_5$ [M]$^+$, 448.2124; found, 448.2118 |
| Compound number | 121 |
| Name | 8-(2,4-Dimethoxyphenyl)-6-methoxy-2-(4-methylphenethyl)-1,2,3,4-tetrahydroisoquinolin-7-ol |
| $^1$H NMR (200 MHz, CDCl$_3$) | δ 2.29 (s, 3H), 2.55-2.84 (m, 6H), 2.84-2.96 (m, 2H), 3.25 (bd, 2H), 3.71 (s, 3H), 3.84 (s, 3H), 3.86 (s, 3H), 6.54-6.60 (m, 2H), 6.62 (s, 1H), 7.01 (s, 1H), 7.02-7.07 (m, 4H) |
| $^{13}$C NMR (50 MHz, CDCl$_3$) | δ 21.1, 29.3, 33.5, 50.6, 54.2, 55.4, 55.7, 56.0, 60.2, 99.1, 104.8, 110.2, 116.4, 122.5, 125.1, 126.7, 128.6, 129.0, 131.9, 135.5, 137.4, 141.4, 145.2, 158.1, 160.7 |
| EIHR-MS | calcd for $C_{27}H_{32}NO_4$ [M + H]$^+$, 434.2331; found, 434.2348 |
| Compound number | 122 |
| Name | 2-(3-Chlorophenethyl)-8-(2,4-dimethoxyphenyl)-6-methoxy-1,2,3,4-tetrahydroisoquinolin-7-ol |
| $^1$H NMR (200 MHz, CDCl$_3$) | δ 2.58-2.99 (m, 8H), 3.12 (d, J = 15.4 Hz, 1H), 3.20 (d, J = 15.3 Hz, 1H), 3.65 (s, 3H), 3.78 (s, 3H), 3.80 (s, 3H), 6.46-6.54 (m, 2H), 6.55 (s, 1H), 6.91-7.01 (m, 2H), 7.03-7.14 (m, 3H) |
| $^{13}$C NMR (50 MHz, CDCl$_3$) | δ 29.2, 33.7, 50.6, 54.2, 55.4, 55.7, 56.0, 59.6, 99.2, 104.8, 110.1, 116.3, 122.5, 125.0, 126.2, 126.5, 127.0, 128.8, 129.6, 131.9, 134.1, 141.4, 142.5, 145.2, 158.1, 160.8 |
| EIHR-MS | calcd for $C_{26}H_{29}ClNO_4$ [M + H]$^+$, 454.1785; found, 454.1798 |
| Compound number | 123 |
| Name | 8-(2,4-Dimethoxyphenyl)-6-methoxy-2-(2-methoxyphenethyl)-1,2,3,4-tetrahydroisoquinolin-7-ol |
| $^1$H NMR (200 MHz, CDCl$_3$) | δ 2.52-2.86 (m, 6H), 2.87-2.98 (m, 2H), 3.27 (s, 2H), 3.71 (s, 3H), 3.75 (s, 3H), 3.83 (s, 3H), 3.86 (s, 3H), 6.53-6.61 (m, 2H), 6.62 (s, 1H), 6.76-6.89 (m, 2H), 7.01-7.19 (m, 3H) |
| $^{13}$C NMR (50 MHz, CDCl$_3$) | δ 28.1, 29.3, 50.3, 54.2, 55.2, 55.4, 55.6, 58.3, 99.1, 104.7, 104.7, 110.1, 110.3, 116.4, 120.4, 122.5, 125.2, 126.9, 127.3, 128.2, 130.2, 131.9, 141.3, 145.1, 157.5, 158.1, 160.7 |
| EIHR-MS | calcd for $C_{27}H_{32}NO_5$ [M + H]$^+$, 450.2280; found, 450.2297 |
| Compound number | 125 |
| Name | 8-(2,4-Dimethoxyphenyl)-6-methoxy-2-(3-phenylpropyl)-1,2,3,4-tetrahydroisoquinolin-7-ol |
| $^1$H NMR (200 MHz, CDCl$_3$) | δ 1.70-1.88 (m, 2H), 2.35-2.47 (m, 2H), 2.53-2.74 (m, 4H), 2.83-2.93 (m, 2H), 3.14 (d, J = 15.2 Hz, 1H), 3.23 (d, J = 15.2 Hz, 1H), 3.71 (s, 3H), 3.85 (s, 3H), 3.86 (s, 3H), 5.33 (s, 1H), 6.54-6.60 (m, 2H), 6.61 (s, 1H), 7.00-7.06 (m, 1H), 7.10-7.20 (m, 3H), 7.21-7.31 (m, 2H) |
| $^{13}$C NMR (50 MHz, CDCl$_3$) | δ 28.7, 29.2, 33.7, 50.5, 54.2, 55.4, 55.7, 56.0, 57.5, 99.1, 104.7, 110.3, 116.3, 122.5, 125.3, 127.0, 128.2, 129.3, 132.0, 138.6, 141.4, 145.2, 158.1, 160.8 |
| EIHR-MS | calcd for $C_{27}H_{32}NO_4$ [M + H]$^+$, 434.2331; found, 434.2356 |
| Compound number | 141 |
| Name | 6-Methoxy-8-(2-methoxyphenyl)-2-(3-(4-nitrophenyl)propyl)-1,2,3,4-tetrahydroisoquinolin-7-ol |
| $^1$H NMR (200 MHz, CDCl$_3$) | δ 1.69-1.90 (m, 2H), 2.29-2.45 (m, 2H), 2.60-2.78 (m, 4H), 2.83-2.96 (m. 2H), 3.11 (d, J = 15.2 Hz, 1H), 3.19 (d, J = 15.2 Hz, 1H), 3.75 (s, 3H), 3.88 (s, 3H), 5.37 (bs, 1H), 6.64 (s, 1H), 6.96-7.09 (m, 2H), 7.14 (dd, J = 7.3, 1.9 Hz, 1H), 7.22-7.32 (m, 2H), 7.32-7.43 (m, 1H), 8.05-8.16 (m, 2H) |
| $^{13}$C NMR (50 MHz, CDCl$_3$) | δ 28.4, 29.4, 33.5, 50.6, 54.2, 55.8, 56.0, 57.0, 110.3, 111.4, 121.0, 122.7, 123.7, 124.2, 125.2, 126.2, 129.3, 131.6, 141.2, 145.2, 146.4, 150.4, 157.1 |
| ESI-MS | m/z 449 ([M + H]$^+$) |
| EIHR-MS | calcd for $C_{26}H_{29}N_2O_5$ [M + H]$^+$, 449.2076; found, 449.2087 |
| Compound number | 142 |
| Name | 6-Methoxy-8-(2-methoxyphenyl)-2-(3-(2-nitrophenyl)propyl)-1,2,3,4-tetrahydroisoquinolin-7-ol |
| $^1$H NMR (200 MHz, CDCl$_3$) | δ 1.69-1.90 (m, 2H), 2.34-2.51 (m, 2H), 2.60-2.78 (m, 2H), 2.78-2.99 (m. 4H), 3.13 (d, J = 15.2 Hz, 1H), 3.23 (d, J = 15.2 Hz, 1H), 3.76 (s, 3H), 3.88 (s, 3H), 6.64 (s, 1H), 6.96-7.10 (m, 2H), 7.15 (dd, J = 7.3, 1.9 Hz, 1H), 7.24-7.29 (m, 1H), 7.32-7.40 (m, 1H), 7.61-7.76 (m, 1H), 7.82-7.92 (m, 1H) |
| $^{13}$C NMR (50 MHz, CDCl$_3$) | δ 28.1, 29.3, 30.8, 50.2, 54.3, 55.7, 56.0, 57.3, 110.3, 111.4, 120.9, 122.8, 124.1, 124.7, 125.4, 126.3, 127.0, 129.4, 131.6, 132.1, 132.9, 137.4, 141.1, 145.2, 149.4, 157.1 |
| ESI-MS | m/z 449 ([M + H]$^+$) |
| EIHR-MS | calcd for $C_{26}H_{29}N_2O_5$ [M + H]$^+$, 449.2076; found, 449.2098 |
| Compound number | 150 |
| Name | 8-Bromo-6,7-dimethoxy-2-phenethyl-1,2,3,4-tetrahydroisoquinoline |
| $^1$H NMR (200 MHz, CDCl$_3$) | δ 2.71-2.94 (m, 8H), 3.63 (s, 2H), 3.82 (s, 3H), 3.83 (s, 3H), 6.63 (s, 1H), 7.20-7.31 (m, 5H) |
| $^{13}$C NMR (50 MHz, CDCl$_3$) | δ 29.7, 34.1, 50.2, 56.1, 56.4, 60.2, 60.6, 111.7, 118.2, 126.2, 126.8, 128.5, 128.8, 131.9, 140.4, 144.6, 151.7 |
| ESI-MS | m/z 376 ([M + H]$^+$), 398 ([M + Na]$^+$) |
| EIHR-MS | calcd for $C_{19}H_{23}BrNO_2$ [M + H]$^+$, 376.0912; found, 376.0905 |
| Compound number | 152 |
| Name | 8-Bromo-6,7-dimethoxy-2-(4-nitrophenethyl)-1,2,3,4-tetrahydroisoquinoline |
| $^1$H NMR (200 MHz, CDCl$_3$) | δ 2.69-2.80 (m, 2H), 2.80-2.93 (m, 4H), 2.96-3.10 (m, 2H), 3.61 (s, 2H), 3.82 (s, 3H), 3.84 (s, 3H), 6.64 (s, 1H), 7.36-7.46 (m, 2H), 8.10-8.19 (m, 2H) |
| $^{13}$C NMR (50 MHz, CDCl$_3$) | δ 29.6, 33.9, 50.2, 56.2, 56.3, 59.1, 60.6, 111.7, 118.2, 123.8, 126.5, 129.7, 131.8, 144.7, 146.6, 148.4, 151.8 |
| ESI-MS | m/z 421 ([M + H]$^+$), 443 ([M + Na]$^+$) |
| EIHR-MS | calcd for $C_{19}H_{22}BrN_2O_4$ [M + H]$^+$, 421.0763; found, 421.0730 |
| Compound number | 153 |
| Name | 8-Bromo-2-(2-chlorophenethyl)-6,7-dimethoxy-1,2,3,4-tetrahydroisoquinoline |
| $^1$H NMR (200 MHz, CDCl$_3$) | δ 2.73-2.95 (m, 6H), 2.99-3.13 (m, 2H), 3.66 (s, 2H), 3.82 (s, 3H), 3.84 (s, 3H), 6.64 (s, 1H), 7.10-7.25 (m, 2H), 7.29-7.39 (m, 2H) |

TABLE 7-continued

The analytical data of the compounds in this invention

| | |
|---|---|
| $^{13}$C NMR (50 MHz, CDCl$_3$) | δ 29.7, 31.7, 50.0, 56.2, 56.4, 58.0, 60.6, 111.8, 118.3, 126.9, 127.0, 127.8, 129.6, 131.0, 131.9, 134.2, 138.0, 144.6, 151.7 |
| ESI-MS | m/z 410 ([M + H]$^+$) |
| EIHR-MS | calcd for C$_{19}$H$_{22}$BrClNO$_2$ [M + H]$^+$, 410.0522; found, 410.0494 |
| Compound number | 154 |
| Name | 8-Bromo-2-(2-fluorophenethyl)-6,7-dimethoxy-1,2,3,4-tetrahydroisoquinoline |
| $^1$H NMR (200 MHz, CDCl$_3$) | δ 2.69-2.90 (m, 6H), 2.90-3.04 (m, 2H), 3.63 (s, 2H), 3.82 (s, 3H), 3.84 (s, 3H), 6.63 (s, 1H), 6.95-7.12 (m, 2H), 7.12-7.33 (m, 2H) |
| $^{13}$C NMR (50 MHz, CDCl$_3$) | δ 27.3, 29.7, 50.0, 56.2, 56.4, 58.4, 60.6, 111.7, 115.3 (J = 22.0 Hz), 118.2, 124.2, 126.8, 127.1 (J = 16.1 Hz), 127.9 (J = 8.0 Hz), 131.1 (J = 4.8 Hz), 131.9, 144.6, 151.6, 161.3 (J = 243 Hz) |
| ESI-MS | m/z 394 ([M + H]$^+$) |
| EIHR-MS | calcd for C$_{19}$H$_{22}$BrFNO$_2$ [M + H]$^+$, 394.0818; found, 394.0806 |
| Compound number | 157 |
| Name | 8-(2-Fluorophenyl)-6,7-dimethoxy-2-phenethyl-1,2,3,4-tetrahydroisoquinoline |
| $^1$H NMR (200 MHz, CDCl$_3$) | δ 2.54-2.88 (m, 6H), 2.88-3.05 (m, 2H), 3.19 (d, J = 15.0 Hz, 1H), 3.30 (d, J = 15.0 Hz, 1H), 3.56 (s, 3H), 3.86 (s, 3H), 6.73 (s, 1H), 7.03-7.41 (m, 9H) |
| $^{13}$C NMR (50 MHz, CDCl$_3$) | δ 29.5, 34.0, 50.3, 54.2, 55.9, 60.0, 60.8, 112.5, 115.6 (J = 22.2 Hz), 123.6, 124.0 (J = 3.2 Hz), 126.1, 128.1, 128.4, 128.7, 129.4, 130.1, 131.8 (J = 3.5 Hz), 140.4, 145.2, 151.0, 159.9 (J = 234 Hz) |
| ESI-MS | m/z 392 ([M + H]$^+$) |
| EIHR-MS | calcd for C$_{25}$H$_{27}$FNO$_2$ [M + H]$^+$, 390.2026; found, 390.2014 |
| Compound number | 158 |
| Name | 8-(2-Chlorophenyl)-6,7-dimethoxy-2-phenethyl-1,2,3,4-tetrahydroisoquinoline |
| $^1$H NMR (200 MHz, CDCl$_3$) | δ 2.55-2.68 (m, 2H), 2.68-2.89 (m, 4H), 2.89-3.00 (m, 2H), 3.17 (s, 2H), 3.58 (s, 3H), 3.87 (s, 3H), 6.73 (s, 1H), 7.10-7.27 (m, 6H), 7.27-7.36 (m, 2H), 7.43-7.53 (m, 1H) |
| $^{13}$C NMR (50 MHz, CDCl$_3$) | δ 29.5, 34.0, 50.4, 53.9, 55.9, 60.0, 60.7, 112.3, 125.7, 126.1, 126.8, 128.4, 128.8, 129.0, 129.5, 130.1, 131.3, 131.8, 133.8, 135.6, 140.4, 144.6, 151.0 |
| ESI-MS | m/z 408 ([M + H]$^+$) |
| EIHR-MS | calcd for C$_{25}$H$_{27}$ClNO$_2$ [M + H]$^+$, 408.1730; found, 408.1730 |
| Compound number | 159 |
| Name | 6,7-Dimethoxy-8-(2-methoxyphenyl)-2-phenethyl-1,2,3,4-tetrahydroisoquinoline |
| $^1$H NMR (200 MHz, CDCl$_3$) | δ 2.54-2.87 (m, 6H), 2.87-3.00 (m, 2H), 3.15 (d, J = 15.1 Hz, 1H), 3.26 (d, J = 15.1 Hz, 1H), 3.52 (s, 3H), 3.74 (s, 3H), 3.86 (s, 3H), 6.69 (s, 1H), 6.92-7.05 (m, 2H), 7.06-7.15 (m, 2H), 7.15-7.29 (m, 4H), 7.29-7.40 (m, 1H) |
| $^{13}$C NMR (50 MHz, CDCl$_3$) | δ 29.6, 34.0, 50.4, 54.1, 55.5, 55.8, 60.1, 60.6, 110.8, 111.8, 120.6, 125.2, 126.1, 126.3, 128.4, 128.8, 128.9, 129.6, 131.2, 140.5, 145.0, 151.0, 156.9 |
| ESI-MS | m/z 404 ([M + H]$^+$) |
| EIHR-MS | calcd for C$_{26}$H$_{30}$NO$_3$ [M + H]$^+$, 404.2226; found, 404.2217 |
| Compound number | 165 |
| Name | 2-(2-Fluorophenethyl)-8-(2-fluorophenyl)-6,7-dimethoxy-1,2,3,4-tetrahydroisoquinoline |
| $^1$H NMR (200 MHz, CDCl$_3$) | δ 2.56-2.68 (m, 2H), 2.68-2.88 (m, 4H), 2.88-3.01 (m, 2H), 3.20 (d, J = 15.1 Hz, 1H), 3.31 (d, J = 15.1 Hz, 1H), 3.56 (s, 3H), 3.86 (s, 3H), 6.73 (s, 1H), 6.89-7.06 (m, 2H), 7.09-7.24 (m, 5H), 7.28-7.42 (m, 1H) |
| $^{13}$C NMR (50 MHz, CDCl$_3$) | δ 27.2, 29.5, 50.1, 54.2, 55.9, 58.2, 60.8, 112.6, 115.3 (J = 21.7 Hz), 115.6 (J = 22.0 Hz), 123.6, 124.0 (J = 3.2 Hz), 126.1, 127.2 (J = 15.9 Hz), 127.8 (J = 7.9 Hz), 128.1, 129.5 (J = 7.9 Hz), 130.2, 131.0 (J = 4.9 Hz), 131.8 (J = 3.0 Hz), 145.2, 151.1, 159.9 (J = 244 Hz), 161.2 (J = 243 Hz) |
| ESI-MS | m/z 410 ([M + H]$^+$) |
| EIHR-MS | calcd for C$_{25}$H$_{26}$F$_2$NO$_2$ [M + H]$^+$, 410.1932; found, 410.1927 |
| Compound number | 166 |
| Name | 8-(2-Chlorophenyl)-2-(2-fluorophenethyl)-6,7-dimethoxy-1,2,3,4-tetrahydroisoquinoline |
| $^1$H NMR (200 MHz, CDCl$_3$) | δ 2.55-2.68 (m, 2H), 2.68-2.88 (m, 4H), 2.88-3.00 (m, 2H), 3.18 (s, 2H), 3.57 (s, 3H), 3.87 (s, 3H), 6.73 (s, 1H), 6.88-7.05 (m, 2H), 7.06-7.24 (m, 3H), 7.26-7.36 (m, 2H), 7.42-7.52 (m, 1H) |
| $^{13}$C NMR (50 MHz, CDCl$_3$) | δ 27.2, 29.4, 50.1, 53.9, 55.9, 58.1, 60.7, 112.4, 115.3 (J = 22.0 Hz), 124.0 (J = 3.2 Hz), 125.6, 126.8, 127.2 (J = 16.0 Hz), 127.8 (J = 7.9 Hz), 129.0, 129.5, 130.1, 131.0 (J = 4.9 Hz), 131.3, 131.8, 133.8, 135.6, 144.7, 151.0, 161.2 (J = 243 Hz) |
| ESI-MS | m/z 426 ([M + H]$^+$) |
| EIHR-MS | calcd for C$_{25}$H$_{26}$ClFNO$_2$ [M + H]$^+$, 426.1636; found, 426.1634 |
| Compound number | 167 |
| Name | 2-(2-Chlorophenethyl)-8-(2-fluorophenyl)-6,7-dimethoxy-1,2,3,4-tetrahydroisoquinoline |
| $^1$H NMR (200 MHz, CDCl$_3$) | δ 2.55-2.70 (m, 2H), 2.70-3.02 (m, 6H), 3.22 (d, J = 15.1 Hz, 1H), 3.32 (d, J = 15.1 Hz, 1H), 3.56 (s, 3H), 3.87 (s, 3H), 6.73 (s, 1H), 7.04-7.24 (m, 6H), 7.24-7.42 (m, 2H) |
| $^{13}$C NMR (50 MHz, CDCl$_3$) | δ 29.5, 31.5, 50.1, 54.3, 55.9, 57.9, 60.8, 112.5, 115.6 (J = 22.1 Hz), 123.6, 124.1, 126.1, 126.9, 127.6, 128.1, 129.4 (J = 7.1 Hz), 129.5, 130.1, 130.9, 131.9, 134.0, 137.9, 145.2, 151.1, 159.9 (J = 243 Hz) |
| ESI-MS | m/z 426 ([M + H]$^+$) |
| EIHR-MS | calcd for C$_{25}$H$_{26}$ClFNO$_2$ [M + H]$^+$, 426.1636; found, 426.1640 |
| Compound number | 168 |
| Name | 2-(2-Chlorophenethyl)-8-(2-chlorophenyl)-6,7-dimethoxy-1,2,3,4-tetrahydroisoquinoline |
| $^1$H NMR (200 MHz, CDCl$_3$) | δ 2.53-2.69 (m, 2H), 2.69-3.03 (m, 6H), 3.20 (s, 2H), 3.57 (s, 3H), 3.87 (s, 3H), 6.73 (s, 1H), 7.02-7.23 (m, 4H), 7.23-7.38 (m, 3H), 7.42-7.54 (m, 1H) |
| $^{13}$C NMR (50 MHz, CDCl$_3$) | δ 29.5, 31.6, 50.2, 54.0, 55.9, 57.9, 60.7, 112.4, 125.7, 126.8, 127.6, 129.0, 129.5, 130.1, 130.9, 131.3, 131.8, 133.8, 134.1, 135.7, 138.0, 144.7, 151.0 |
| ESI-MS | m/z 442 ([M + H]$^+$) |
| EIHR-MS | calcd for C$_{25}$H$_{26}$Cl$_2$NO$_2$ [M + H]$^+$, 442.1341; found, 442.1335 |
| Compound number | 171 |
| Name | 8-(2-Fluorophenyl)-6,7-dimethoxy-2-(4-nitrophenethyl)-1,2,3,4-tetrahydroisoquinoline |
| $^1$H NMR (200 MHz, CDCl$_3$) | δ 2.62-3.00 (m, 8H), 3.20 (dd, J = 17.9, 15.1 Hz, 2H), 3.55 (s, 3H), 3.87 (s, 3H), 6.73 (s, 1H), 7.07-7.24 (m, 3H), 7.25-7.42 (m, 3H), 8.04-8.15 (m, 2H) |
| $^{13}$C NMR (50 MHz, CDCl$_3$) | δ 29.6, 34.1, 50.5, 54.2, 55.9, 59.0, 60.8, 112.5, 115.7 (J = 22.3 Hz), 123.5, 123.7 (J = 17.4 Hz), 124.0, 125.8, 128.1, 129.5 (J = 7.3 Hz), 129.6, 130.0, 131.8 (J = 3.1 Hz), 145.3, 151.0, 161.2 (J = 243 Hz |
| ESI-MS | m/z 437 ([M + H]$^+$) |
| EIHR-MS | calcd for C$_{25}$H$_{26}$FN$_2$O$_4$ [M + H]$^+$, 437.1877; found, 437.1874 |
| Compound number | 172 |
| Name | 8-(2-Chlorophenyl)-6,7-dimethoxy-2-(4-nitrophenethyl)-1,2,3,4-tetrahydroisoquinolineε |
| $^1$H NMR (200 MHz, CDCl$_3$) | δ 2.61-2.99 (m, 8H), 3.13 (dd, J = 16.6, 15.2 Hz, 2H), 3.57 (s, 3H), 3.87 (s, 3H), 6.73 (s, 1H), 7.11-7.22 (m, 2H), 7.24-7.37 (m, 4H), 7.47-7.52 (m, 1H), 8.03-8.14 (m, 2H) |
| $^{13}$C NMR (50 MHz, CDCl$_3$) | δ 29.5, 34.0, 50.6, 53.9, 58.9, 60.7, 112.3, 123.7, 125.3, 126.9, 129.0, 129.6, 130.0, 131.3, 131.8, 133.7, 135.6, 144.7, 146.5, 148.6, 151.1 |
| ESI-MS | m/z 453 ([M + H]$^+$) |
| EIHR-MS | calcd for C$_{25}$H$_{26}$ClN$_2$O$_4$ [M + H]$^+$, 453.1581; found, 453.1571 |
| Compound number | 173 |
| Name | 6,7-Dimethoxy-8-(2-methoxyphenyl)-2-(4-nitrophenethyl)-1,2,3,4-tetrahydroisoquinoline |
| $^1$H NMR (200 MHz, CDCl$_3$) | δ 2.59-3.00 (m, 8H), 3.17 (dd, J = 19.8, 15.0 Hz, 2H), 3.52 (s, 3H), 3.73 (s, 3H), 3.86 (s, 3H), 6.69 (s, |

TABLE 7-continued

The analytical data of the compounds in this invention

| | |
|---|---|
| | 1H), 6.92-7.04 (m, 2H), 7.07 (dd, J = 7.4, 2.2 Hz, 1H), 7.26-7.41 (m, 3H), 8.03-8.14 (m, 2H) |
| $^{13}$C NMR (50 MHz, CDCl$_3$) | δ 29.6, 34.0, 50.6, 54.1, 55.5, 55.9, 59.0, 60.6, 110.8, 111.8, 120.6, 123.6, 125.1, 126.0, 129.0, 129.6, 131.1, 145.1, 146.5, 148.7, 151.1, 156.9 |
| ESI-MS | m/z 449 ([M + H]$^+$) |
| EIHR-MS | calcd for C$_{26}$H$_{29}$N$_2$O$_5$ [M + H]$^+$, 449.2076; found, 449.2071 |

The 5-HT$_{2A}$ Receptor Binding Affinity of Compounds 116, 157 and 167.

The 5-HT$_{2A}$ receptor binding affinity data are represented by K$_i$ values. As shown in Table 8, the 5-HT$_{2A}$ receptor binding affinity of compounds 116, 157 and 167 are higher than those of the well-known 5-HT$_{2A}$ receptor antagonists, sarpogrelate and ketanserin.

TABLE 8

The 5-HT$_{2A}$ receptor binding affinity data

| | Prior-art | | The present invention (compound number) | | |
|---|---|---|---|---|---|
| | sarpogrelate | ketanserin | 116 | 157 | 167 |
| K$_i$ (nM) | 8.39 | 3.5 | 3.47 | 2.21 | 0.119 |

Figure 7:
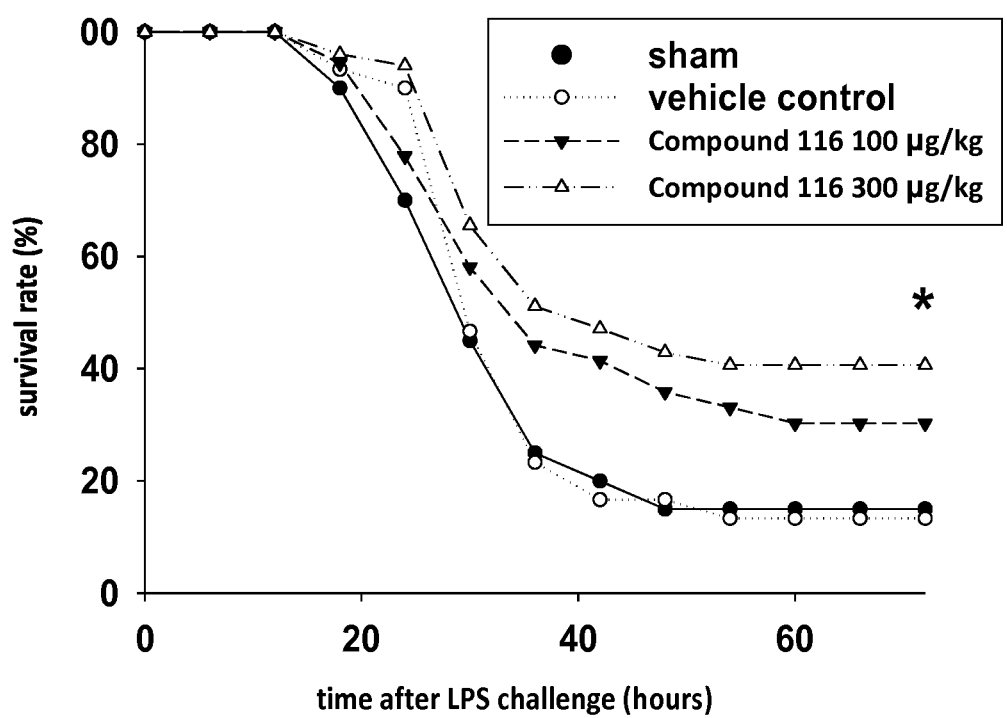
FIG. 7 shows the protective effects of post-treatment of multiple doses of compound 116 on LPS induced endotoxaemia in the mice model.

Protective Effects of Post-Treatment of Multiple Doses of Compound 116 on LPS Induced Endotoxaemia in Mice Model:

12 hours after intraperitoneal injection of lipopolysaccharide (LPS) 100 mg/kg, compound 116 100 μg/kg or 300 μg/kg were administrated intraperitoneally or subcutaneously every 6 hour till 48 hours after LPS insults. FIG. 7 shows the result. Both 100 μg/kg and 300 μg/kg treatment of compound 116 shifted the survive curve rightward significantly compared to the vehicle control group (p<0.01.). Survival curves were compared by the Log rank test, and 3 days survival rate was compared by the chi square test.

Figure 8:
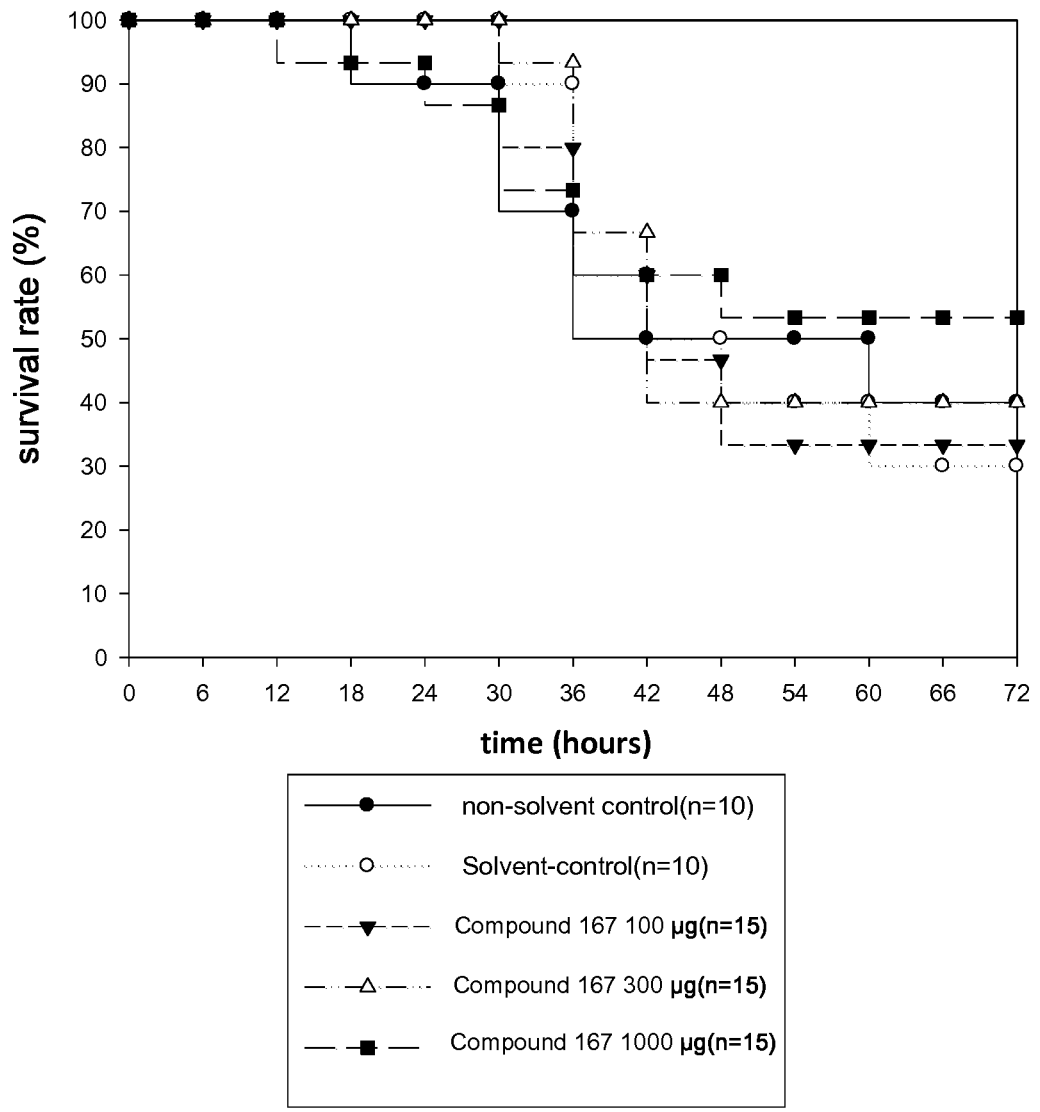
FIG. 8 shows the protective effects of post-treatment of multiple doses of compound 167 on LPS induced endotoxaemia in the mice model.

Protective Effects of Post-Treatment of Multiple Doses of Compound 167 on LPS Induced Endotoxaemia in Mice Model:

The experiment method is the same as described above and FIG. 8 shows the result.

Figures 9A, 9B, 9C, 9D:
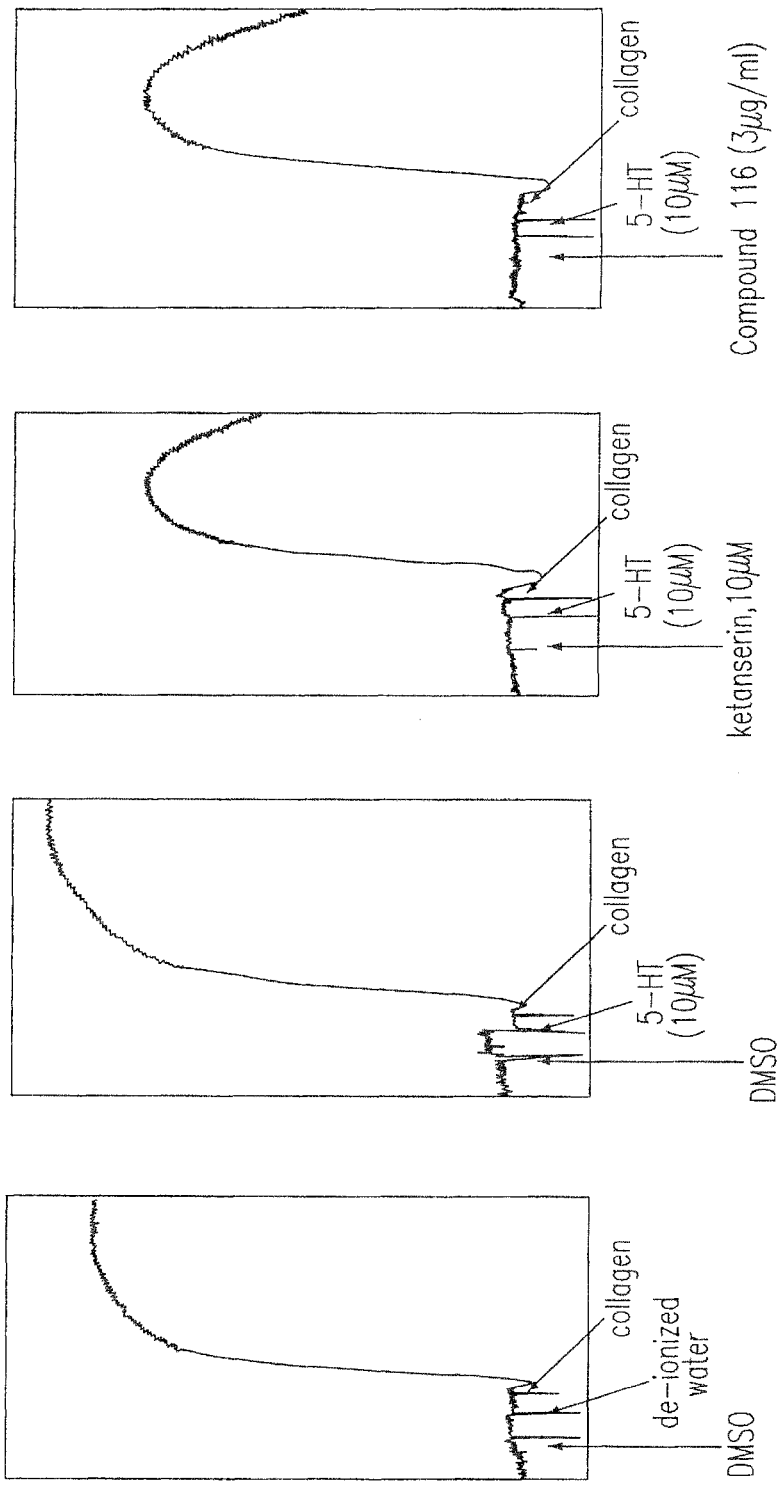
FIGS. 9a-9d show that compound 116 did not exert platelet activation, but inhibited 5-HT induced amplification of platelet aggregation.

Compound 116 Did not Exert Platelet Activation, but Inhibited 5-HT Induced Amplification of Platelet Aggregation:

Blood samples were collected from male adult Spraque-Dawley rats, and platelet rich plasma (PRP) and platelet poor plasma (PPP) were obtained by centrifugation. Aggregation was elicited by adding collagen 3 μg/mL in PRP, and the aggregation response was recorded as the change of light transmission of PRP with Lumi-aggregometer. In FIG. 9a, collagen induced platelet aggregation, and the aggregation response was amplified by adding 10 μM serotonin in 30 seconds before adding collagen, as shown in FIG. 9b. The amplifying effects of serotonin was blocked by adding 10 μM ketanserin or 3 μg/mL compound 116 in 30 seconds before adding serotonin, as shown in FIG. 9c and FIG. 9d.

Figure 10:
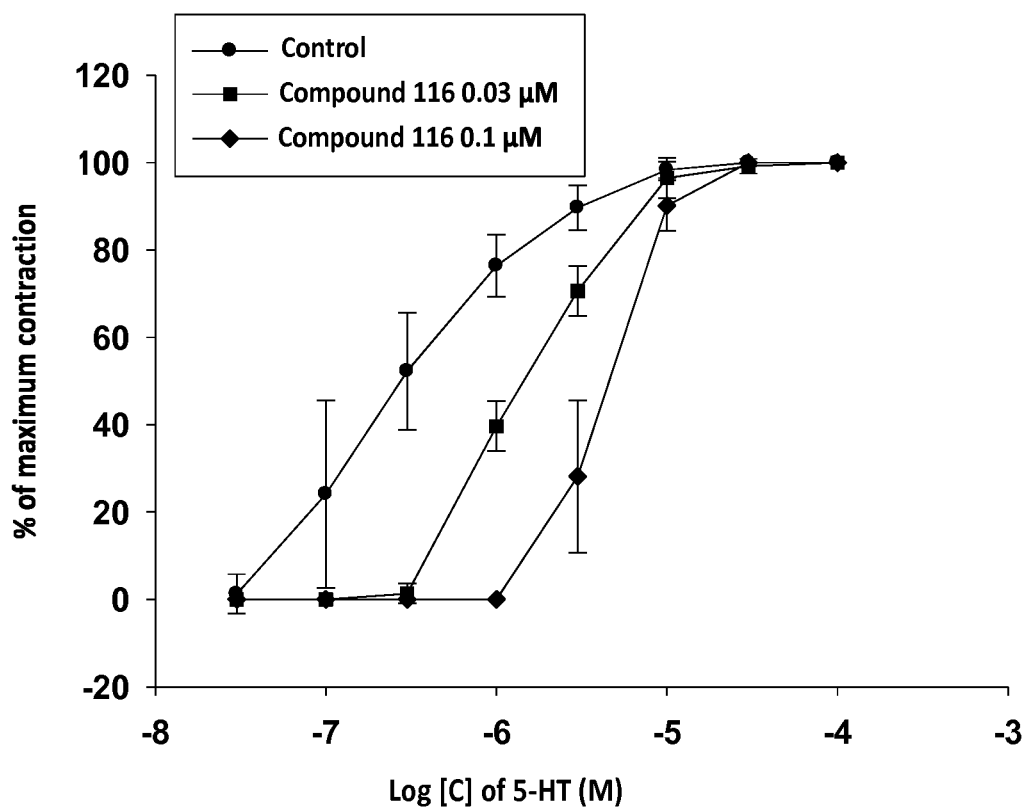
FIG. 10 shows that compound 116 inhibits serotonin induced rat de-endothelial thoracic descending aorta contraction.

Compound 116 Inhibits Serotonin Induced Rat De-Endothelial Thoracic Descending Aorta Contraction:

Thoracic aortae were obtained from adult male Sprague Dawley rats. The aortae were cleared of adhering periadventitial fat and cut into strips 3-4 mm in length. Later, the relaxation in response to acetylcholine (1 μM) following PE (0.1 μM) was considered as evidence that the endothelium was intact. The tissue was incubated with warmed (37° C.), oxygenated (95% O$_2$/5% CO$_2$) Krebs-Henseleit solution (KBS, pH7.4) consisting of NaCl 118.2 mM, KCl 4.7 mM, KH$_2$PO$_4$ 1.2 mM, MgSO$_4$ 1.2 mM, CaCl$_2$·2H$_2$O 1.9 mM, NaHCO$_3$ 25 mM and glucose 11.7 mM. Indomethacin (10 μM) was added to prevent the production of prostanoids. One end of the segment was fixed to the organ bath chamber, and the other to a force transducer (Type BG 25; Gould, Oxnard, Calif., USA) in which tension is recorded (model RS 3400 recorder, Gould). The preparations were allowed to equilibrate for at least 60 min under a passive tension of 1.5±0.2 g. Cumulative responses to serotonin (30 nM-0.1 mM) were examined for 20 min after addition of 0.03 or 0.1 μM compound 116 to the organ bath. Contraction responses were expressed as the percentage of maximum contraction. As shown in FIG. 10, compound 116 inhibits serotonin induced smooth muscle contraction in a dose dependent manner.

EMBODIMENTS

1. A compound, comprising a formula of:

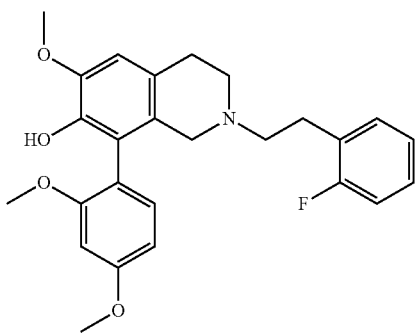 [SMILES: COc1ccc(-c2c(O)c(OC)cc3c2CN(CCc2ccccc2F)CC3)c(OC)c1]

2. A compound as claimed in claim 1, providing an antagonism to a 5-HT$_{2A}$ receptor.
3. A compound as claimed in claim 1, inhibiting an aorta contraction.
4. A compound as claimed in claim 3, wherein the aorta contraction is induced by a serotonin
5. A compound as claimed in claim 1, inhibiting a platelet aggregation.
6. A compound as claimed in claim 5, wherein the platelet aggregation is induced by a serotonin.
7. A compound or a pharmaceutically acceptable salt thereof, comprising a formula of:

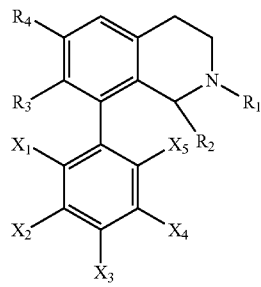

wherein R$_1$ is one selected from a group consisting of C$_{3-12}$ linear chain alkyl group, C$_{1-12}$ branched chain alkyl group, (CH$_2$)$_n$(Hete)R$_{10}$R$_{11}$R$_{12}$ and (CH$_2$)$_n$ ArR$_{10}$R$_{11}$R$_{12}$, wherein the n is an integer from 2 to 6, Hete is a heterocyclic group, and R$_{10}$, R$_{11}$ and R$_{12}$ are independently selected from a group consisting of hydrogen, halo group, nitro group, amino group, cyano group, acetyl group, C$_{1-6}$ linear chain saturated alkyl group, C$_{1-6}$ linear chain saturated alkoxy group and C$_{1-6}$ linear chain saturated haloalkyl group;

Ar is an aryl group;

R$_2$ is one of a hydrogen and a C$_{1-6}$ linear chain saturated alkyl group;

R$_3$ is one of a hydroxyl group and a C$_{1-6}$ linear chain saturated alkoxy group;

R$_4$ is one of a hydroxyl group and a C$_{1-6}$ linear chain saturated alkoxy group; and X$_1$, X$_2$, X$_3$, X$_4$ and X$_5$ are independently selected from a group consisting of hydrogen, halo group, nitro group, amino group, cyano group, acetyl group, C$_{1-6}$ linear chain saturated alkyl group, C$_{1-6}$ branched chain saturated alkyl group, C$_{1-6}$ linear chain saturated alkoxy group, C$_{1-6}$ branched chain saturated alkoxy group, C$_{1-6}$ linear chain saturated alkylthio group, C$_{1-6}$ branched chain saturated alkylthio group, C$_{1-6}$ linear chain saturated haloalkyl group and C$_{1-6}$ branched chain saturated haloalkyl group.

8. A compound as claimed in claim 7, wherein when any of R$_{10}$, R$_{11}$ and R$_{12}$ contains the halo group, the halo group is one selected from a group consisting of fluorine, chlorine, bromine and iodine.

9. A compound as claimed in claim 7, wherein the heterocyclic group is one selected from a group consisting of indolyl group, isoindolyl group, indazolyl group, benzofuranyl group, isobenzofuranyl group, benzothiophenyl group, benzimidazolyl group, benzoxazolyl group and benzothiazolyl group, and the aryl group comprises a naphthyl group.

10. A pharmaceutical composition, comprising:
a pharmaceutically acceptable carrier; and
a therapeutically effective amount of a compound having a formula of:

wherein R$_1$ is one selected from a group consisting of C$_{3-12}$ linear chain alkyl group, C$_{3-12}$ branched chain alkyl group, (CH$_2$)$_n$(Hete)R$_{10}$R$_{11}$R$_{12}$ and (CH$_2$)$_n$ArR$_{10}$R$_{11}$R$_{12}$, wherein the n is an integer from 2 to 6, Hete is a heterocyclic group, the Ar is an aryl group, and R$_{10}$, R$_{11}$ and R$_{12}$ are independently selected from a group consisting of hydrogen, halo group, nitro group, amino group, cyano group, acetyl group, C$_{1-6}$ linear chain saturated alkyl group, C$_{1-6}$ linear chain saturated alkoxy group and C$_{1-6}$ linear chain saturated haloalkyl group;

R$_2$ is one of a hydrogen and a C$_{1-6}$ linear chain saturated alkyl group;

R$_3$ is one of a hydroxyl group and a C$_{1-6}$ linear chain saturated alkoxy group;

R$_4$ is one of a hydroxyl group and a C$_{1-6}$ linear chain saturated alkoxy group; and X$_1$, X$_2$, X$_3$, X$_4$ and X$_5$ are independently selected from a group consisting of hydrogen, halo group, nitro group, amino group, cyano group, acetyl group, C$_{1-6}$ linear chain saturated alkyl group, C$_{1-6}$ branched chain saturated alkyl group, C$_{1-6}$ linear chain saturated alkoxy group, C$_{1-6}$ branched chain saturated alkoxy group, C$_{1-6}$ linear chain saturated alkylthio group, C$_{1-6}$ branched chain saturated alkylthio group, C$_{1-6}$ linear chain saturated haloalkyl group and C$_{1-6}$ branched chain saturated haloalkyl group.

11. A pharmaceutical composition as claimed in claim 10, wherein when any of R$_{10}$, R$_{11}$ and R$_{12}$ contains the halo group, the halo group is one selected from a group consisting of fluorine, chlorine, bromine and iodine.

12. A pharmaceutical composition as claimed in claim 10, wherein the heterocyclic group is one selected from a group consisting of indolyl group, isoindolyl group, indazolyl group, benzofuranyl group, isobenzofuranyl group, benzothiophenyl group, benzimidazolyl group, benzoxazolyl group and benzothiazolyl group and the aryl group comprises naphthyl group.

13. A method of treating a sepsis, comprising a step of administering to a subject in need thereof an effective amount of the pharmaceutical composition of claim 10.

What is claimed is:

1. A compound, comprising a formula of:

2. A compound as claimed in claim 1, providing an antagonism to a 5-HT2A receptor.

3. A compound as claimed in claim 1, inhibiting an aorta contraction.

4. A compound as claimed in claim 3, wherein the aorta contraction is induced by a serotonin.

5. A compound as claimed in claim 1, inhibiting a platelet aggregation.

6. A compound as claimed in claim 5, wherein the platelet aggregation is induced by a serotonin.

7. A compound or a pharmaceutically acceptable salt thereof, comprising a formula of:

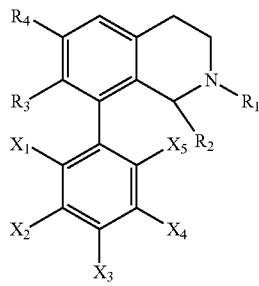

wherein $R_1$ is one selected from a group consisting of $C_{3-12}$ linear chain alkyl group, $C_{3-12}$ branched chain alkyl group, $(CH_2)_n(Hete)R_{10}R_{11}R_{12}$ and $(CH_2)_n ArR_{10}R_{11}R_{12}$, wherein the n is an integer from 2 to 6, Hete is a heterocyclic group, and $R_{10}$, $R_{11}$ and $R_{12}$ are independently selected from a group consisting of hydrogen, halo group, nitro group, amino group, cyano group, acetyl group, $C_{1-6}$ linear chain saturated alkyl group, $C_{1-6}$ linear chain saturated alkoxy group and $C_{1-6}$ linear chain saturated haloalkyl group; Ar is an aryl group;

$R_2$ is one of a hydrogen and a $C_{1-6}$ linear chain saturated alkyl group;

$R_3$ is one of a hydroxyl group and a $C_{1-6}$ linear chain saturated alkoxy group;

$R_4$ is one of a hydroxyl group and a $C_{1-6}$ linear chain saturated alkoxy group; and $X_1$, $X_2$, $X_3$, $X_4$ and $X_5$ are independently selected from a group consisting of hydrogen, halo group, nitro group, amino group, cyano group, acetyl group, $C_{1-6}$ linear chain saturated alkyl group, $C_{1-6}$ branched chain saturated alkyl group, $C_{1-6}$ linear chain saturated alkoxy group, $C_{1-6}$ branched chain saturated alkoxy group, $C_{1-6}$ linear chain saturated alkylthio group, $C_{1-6}$ branched chain saturated alkylthio group, $C_{1-6}$ linear chain saturated haloalkyl group and $C_{1-6}$ branched chain saturated haloalkyl group.

8. A compound as claimed in claim 7, wherein when any of $R_{10}$, $R_{11}$ and $R_{12}$ contains the halo group, the halo group is one selected from a group consisting of fluorine, chlorine, bromine and iodine.

9. A compound as claimed in claim 7, wherein the heterocyclic group is one selected from a group consisting of indolyl group, isoindolyl group, indazolyl group, benzofuranyl group, isobenzofuranyl group, benzothiophenyl group, benzimidazolyl group, benzoxazolyl group and benzothiazolyl group, and the Ar is an aryl group comprising a naphthyl group.

10. A pharmaceutical composition, comprising:
a pharmaceutically acceptable carrier; and
a therapeutically effective amount of a compound having a formula of:

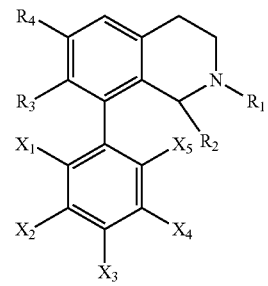

wherein $R_1$ is one selected from a group consisting of $C_{3-12}$ linear chain alkyl group, $C_{3-12}$ branched chain alkyl group, $(CH_2)_n(Hete)R_{10}R_{11}R_{12}$ and $(CH_2)_n ArR_{10}R_{11}R_{12}$, wherein the n is an integer from 2 to 6, Hete is a heterocyclic group, and $R_{10}$, $R_{11}$ and $R_{12}$ are independently selected from a group consisting of hydrogen, halo group, nitro group, amino group, cyano group, acetyl group, $C_{1-6}$ linear chain saturated alkyl group, $C_{1-6}$ linear chain saturated alkoxy group and $C_{1-6}$ linear chain saturated haloalkyl group; Ar is an aryl group;

$R_2$ is one of a hydrogen and a $C_{1-6}$ linear chain saturated alkyl group;

$R_3$ is one of a hydroxyl group and a $C_{1-6}$ linear chain saturated alkoxy group;

$R_4$ is one of a hydroxyl group and a $C_{1-6}$ linear chain saturated alkoxy group; and $X_1$, $X_2$, $X_3$, $X_4$ and $X_5$ are independently selected from a group consisting of hydrogen, halo group, nitro group, amino group, cyano group, acetyl group, $C_{1-6}$ linear chain saturated alkyl group, $C_{1-6}$ branched chain saturated alkyl group, $C_{1-6}$ linear chain saturated alkoxy group, $C_{1-6}$ branched chain saturated alkoxy group, $C_{1-6}$ linear chain saturated alkylthio group, $C_{1-6}$ branched chain saturated alkylthio group, $C_{1-6}$ linear chain saturated haloalkyl group and $C_{1-6}$ branched chain saturated haloalkyl group.

11. A pharmaceutical composition as claimed in claim 10, wherein when any of $R_{10}$, $R_{11}$ and $R_{12}$ contains the halo group, the halo group is one selected from a group consisting of fluorine, chlorine, bromine and iodine.

12. A pharmaceutical composition as claimed in claim 10, wherein the heterocyclic group is one selected from a group consisting of indolyl group, isoindolyl group, indazolyl group, benzofuranyl group, isobenzofuranyl group, benzothiophenyl group, benzimidazolyl group, benzoxazolyl group and benzothiazolyl group and the Ar is aryl group comprising naphthyl group.

13. A method of treating a sepsis, comprising a step of administering to a subject in need thereof an effective amount of the pharmaceutical composition of claim 10.

* * * * *